US009730941B2

(12) United States Patent
Lu et al.

(10) Patent No.: US 9,730,941 B2
(45) Date of Patent: Aug. 15, 2017

(54) METHODS AND COMPOSITIONS FOR THE INHIBITION OF PIN1

(71) Applicants: Beth Israel Deaconess Medical Center, Inc., Boston, MA (US); The United States of America, as represented by the Secretary, Department of Health and Human Services, Washington, DC (US)

(72) Inventors: Kun Ping Lu, Newton, MA (US); Matthew Brian Boxer, Rockville, MD (US); Mindy Irene Emily Davis, Rockville, MD (US); Rajan Pragani, Rockville, MD (US); Min Shen, Rockville, MD (US); Anton Momtchilov Simeonov, Rockville, MD (US); Shuo Wei, Chestnut Hill, MA (US); Xiao Zhen Zhou, Newton, MA (US)

(73) Assignees: Beth Israel Deaconess Medical Center, Inc., Boston, MA (US); The United States of America as represented by the Secretary, Department of Health and Human Services, Washington, DC (US)

( * ) Notice: Subject to any disclaimer, the term of this patent is extended or adjusted under 35 U.S.C. 154(b) by 149 days.

(21) Appl. No.: 14/406,401

(22) PCT Filed: Jun. 7, 2013

(86) PCT No.: PCT/US2013/044747
§ 371 (c)(1),
(2) Date: Dec. 8, 2014

(87) PCT Pub. No.: WO2013/185055
PCT Pub. Date: Dec. 12, 2013

(65) Prior Publication Data
US 2015/0133442 A1 May 14, 2015

Related U.S. Application Data

(60) Provisional application No. 61/656,806, filed on Jun. 7, 2012.

(51) Int. Cl.
| A61K 31/5377 | (2006.01) |
| A61K 31/473 | (2006.01) |
| A61K 45/06 | (2006.01) |
| A61K 31/185 | (2006.01) |
| A61K 31/341 | (2006.01) |
| A61K 31/357 | (2006.01) |
| A61K 31/365 | (2006.01) |
| A61K 31/381 | (2006.01) |
| A61K 31/382 | (2006.01) |
| A61K 31/402 | (2006.01) |
| A61K 31/4025 | (2006.01) |
| A61K 31/404 | (2006.01) |
| A61K 31/405 | (2006.01) |
| A61K 31/4245 | (2006.01) |
| A61K 31/427 | (2006.01) |
| A61K 31/428 | (2006.01) |
| A61K 31/4704 | (2006.01) |
| A61K 31/496 | (2006.01) |

(52) U.S. Cl.
CPC ........ *A61K 31/5377* (2013.01); *A61K 31/185* (2013.01); *A61K 31/341* (2013.01); *A61K 31/357* (2013.01); *A61K 31/365* (2013.01); *A61K 31/381* (2013.01); *A61K 31/382* (2013.01); *A61K 31/402* (2013.01); *A61K 31/404* (2013.01); *A61K 31/405* (2013.01); *A61K 31/4025* (2013.01); *A61K 31/427* (2013.01); *A61K 31/428* (2013.01); *A61K 31/4245* (2013.01); *A61K 31/473* (2013.01); *A61K 31/4704* (2013.01); *A61K 31/496* (2013.01); *A61K 45/06* (2013.01)

(58) Field of Classification Search
None
See application file for complete search history.

(56) References Cited

U.S. PATENT DOCUMENTS

| 4,683,195 A | 7/1987 | Mullis et al. |
| 4,683,202 A | 7/1987 | Mullis |
| 5,223,409 A | 6/1993 | Ladner et al. |
| 5,283,317 A | 2/1994 | Saifer et al. |
| 5,459,039 A | 10/1995 | Modrich et al. |
| 5,498,531 A | 3/1996 | Jarrell |
| 5,952,467 A | 9/1999 | Hunter et al. |
| 5,972,697 A | 10/1999 | Hunter et al. |

(Continued)

FOREIGN PATENT DOCUMENTS

| JP | 2004-532390 A | 10/2004 |
| WO | WO-94/10300 A1 | 5/1994 |

(Continued)

OTHER PUBLICATIONS

Wulf et al, The EMBO Journal, vol. 20(3), pp. 3459-3472, 2001.*

(Continued)

*Primary Examiner* — Svetlana M Ivanova
(74) *Attorney, Agent, or Firm* — Clark & Elbing LLP; Kristina Bieker-Brady

(57) ABSTRACT

The invention features compositions and methods for inhibiting the Pin1 protein, and the treatment of disorders characterized by elevated Pin1 levels.

3 Claims, 15 Drawing Sheets

(56) References Cited

U.S. PATENT DOCUMENTS

| | | |
|---|---|---|
| 6,462,173 B1 | 10/2002 | Lu et al. |
| 6,495,376 B1 | 12/2002 | Lu et al. |
| 6,596,848 B1 | 7/2003 | Hunter et al. |
| 6,649,611 B2 | 11/2003 | Blumberg et al. |
| 6,764,698 B1 | 7/2004 | Byun et al. |
| 7,125,677 B2 | 10/2006 | Hunter et al. |
| 7,125,955 B2 | 10/2006 | Hunter et al. |
| 7,148,003 B2 | 12/2006 | Hunter et al. |
| 7,161,060 B1 | 1/2007 | Duff et al. |
| 7,164,012 B2 | 1/2007 | Hunter et al. |
| 7,175,830 B2 | 2/2007 | Collins et al. |
| 7,592,145 B2 | 9/2009 | Bao et al. |
| 8,129,131 B2 | 3/2012 | Lu et al. |
| 8,258,099 B2 | 9/2012 | Lu et al. |
| 8,771,693 B2 | 7/2014 | Lu et al. |
| 2002/0002552 A1 | 1/2002 | Schultz et al. |
| 2002/0025521 A1 | 2/2002 | Lu et al. |
| 2002/0106348 A1 | 8/2002 | Huang et al. |
| 2004/0176912 A1 | 9/2004 | Sowadski et al. |
| 2005/0159485 A1 | 7/2005 | Jost-Price et al. |
| 2005/0239095 A1 | 10/2005 | Lu et al. |
| 2005/0250742 A1 | 11/2005 | Dagostino et al. |
| 2006/0018899 A1 | 1/2006 | Kao et al. |
| 2006/0074222 A1 | 4/2006 | Lu et al. |
| 2007/0072875 A1 | 3/2007 | McMaster |
| 2007/0203236 A1 | 8/2007 | Smith et al. |
| 2008/0118505 A1 | 5/2008 | Tedder |
| 2008/0214470 A1 | 9/2008 | Lu et al. |
| 2008/0248043 A1 | 10/2008 | Babcook et al. |
| 2009/0053209 A1 | 2/2009 | Malter et al. |
| 2009/0105249 A1 | 4/2009 | Benjamin et al. |
| 2009/0258352 A1 | 10/2009 | Lu et al. |
| 2010/0010084 A1 | 1/2010 | Yu |
| 2010/0278832 A1 | 11/2010 | Kamogawa et al. |
| 2011/0034554 A1 | 2/2011 | Washington |
| 2011/0065704 A1 | 3/2011 | Ryder |
| 2011/0077250 A1 | 3/2011 | Ryder |
| 2011/0104756 A1 | 5/2011 | Rodriguez et al. |
| 2012/0183560 A1 | 7/2012 | Akassoglou |
| 2013/0028900 A1 | 1/2013 | Lu et al. |
| 2014/0086909 A1 | 3/2014 | Lu et al. |
| 2014/0219957 A1 | 8/2014 | Lu et al. |
| 2014/0242100 A1 | 8/2014 | Lu et al. |
| 2015/0044278 A1 | 2/2015 | Lu et al. |

FOREIGN PATENT DOCUMENTS

| | | |
|---|---|---|
| WO | WO-94/16101 A2 | 7/1994 |
| WO | WO-97/17986 A1 | 5/1997 |
| WO | WO-99/09969 A1 | 3/1999 |
| WO | WO-02/064015 A2 | 8/2002 |
| WO | WO-02/065091 A2 | 8/2002 |
| WO | WO-02/092765 A2 | 11/2002 |
| WO | WO-03/073999 A2 | 9/2003 |
| WO | WO-2004/016751 A2 | 2/2004 |
| WO | WO-2004/101745 A2 | 11/2004 |
| WO | WO-2005/027727 A2 | 3/2005 |
| WO | WO-2006/002097 A2 | 1/2006 |
| WO | WO-2006/028576 A2 | 3/2006 |
| WO | WO-2007/133702 A2 | 11/2007 |
| WO | WO-2008/137488 A1 | 11/2008 |
| WO | WO-2009/146218 A2 | 12/2009 |
| WO | WO-2010/081488 A1 | 7/2010 |
| WO | WO-2010/141738 A2 | 12/2010 |
| WO | WO-2011/056561 A1 | 5/2011 |
| WO | WO-2011/104671 A1 | 9/2011 |
| WO | WO-2012/125724 A1 | 9/2012 |
| WO | WO-2012/149334 A2 | 11/2012 |
| WO | WO-2012/162698 A1 | 11/2012 |
| WO | WO-2013/185055 A1 | 12/2013 |
| WO | WO-2014/152157 A2 | 9/2014 |
| WO | WO-2015/143190 A1 | 9/2015 |
| WO | WO-2016/011265 A2 | 1/2016 |
| WO | WO-2016/145186 A1 | 9/2016 |

OTHER PUBLICATIONS

U.S. Appl. No. 61/490,338, Lu et al.
U.S. Appl. No. 61/968,862, Lu et al.
Abravaya et al., "Detection of point mutations with a modified ligase chain reaction (Gap-LCR)," Nucleic Acids Res. 23(4):675-82 (1995).
Barany, "Genetic disease detection and DNA amplification using cloned thermostable ligase," Proc Natl Acad Sci. U.S.A. 88:189-193 (1991).
Carell et al., "A novel procedure for the synthesis of libraries containing small organic molecules," Angew Chem Int Ed Engl. 33(20):2059-2061 (1994).
Cho et al., "An unnatural biopolymer," Science. 261(5126):1303-1305 (1993).
Cotton et al., "Reactivity of cytosine and thymine in single-base-pair mismatches with hydroxylamine and osmium tetroxide and its application to the study of mutations," Proc Natl Acad Sci U.S.A. 85(12):4397-401 (1988).
Cull et al., "Screening for receptor ligands using large libraries of peptides linked to the C terminus of the lac repressor," Proc Natl Acad Sci U S A. 89(5): 1865-1869 (1992).
Cwirla et al., "Peptides on phage: a vast library of peptides for identifying ligands," Proc Natl Acad Sci U.S.A. 87(16):6378-82 (1990).
DeWitt et al., "'Diversomers': an approach to nonpeptide, nonoligomeric chemical diversity," Proc Natl Acad Sci U S A. 90(15):6909-6913 (1993).
Erb et al., "Recursive deconvolution of combinatorial chemical libraries," Proc Natl Acad Sci U S A. 91(24):11422-11426 (1994).
Esnault et al., "Pin1 modulates the type 1 immune response," PLoS One. 2(2):e226 (2007).
Fodor et al., "Multiplexed biochemical assays with biological chips," Nature. 364(6437):555-556 (1993).
Gallop et al., "Applications of combinatorial technologies to drug discovery. 1. Background and peptide combinatorial libraries," J Med Chem. 37(9):1233-1251 (1994).
Gianni et al., "Inhibition of the peptidyl-prolyl-isomerase Pin1 enhances the responses of acute myeloid leukemia cells to retinoic acid via stabilization of RARalpha and PML-RARalpha," Cancer Res. 69(3):1016-26 (2009).
Gibbs et al., "Detection of single DNA base differences by competitive oligonucleotide priming," Nucleic Acids Res. 17(7):2437-48 (1989).
Guatelli et al., "Isothermal, in vitro amplification of nucleic acids by a multienzyme reaction modeled after retroviral replication," Proc Natl Acad Sci U S A. 87(5):1874-8 (1990).
Houghten et al., "The use of synthetic peptide combinatorial libraries for the identification of bioactive peptides," Biotechniques. 13(3):412-21 (1992).
International Search Report and Written Opinion for International Application No. PCT/US13/44747, mailed Nov. 12, 2013 (18 pages).
International Search Report and Written Opinion for International Application No. PCT/US14/027017, mailed Oct. 28, 2014 (19 pages).
International Search Report and Written Opinion for International Application No. PCT/US2012/029077, mailed Jul. 18, 2012 (8 pages).
International Search Report for International Application No. PCT/US2012/039850, mailed Oct. 3, 2012 (3 pages).
Jeong et al., "Novel role of Pin1 induction in type II collagen-mediated rheumatoid arthritis," J Immunol. 183(10):6689-97 (2009).
Kwoh et al., "Transcription-based amplification system and detection of amplified human immunodeficiency virus type 1 with a bead-based sandwich hybridization format," Proc Natl Acad Sci U S A. 86(4):1173-7 (1989).
Lam et al., "A new type of synthetic peptide library for identifying ligand-binding activity," Nature. 354(6348):82-4 (1991).
Lam et al., "Prolyl isomerase Pin1 is highly expressed in Her2-positive breast cancer and regulates erbB2 protein stability," Mol Cancer 7(91):1-12 (2008).

(56) References Cited

OTHER PUBLICATIONS

Lam, "Application of combinatorial library methods in cancer research and drug discovery," Anticancer Drug Des. 12(3):145-67 (1997).
Linder et al., "Pharmacogenetics: a laboratory tool for optimizing therapeutic efficiency," Clin Chem. 43(2):254-66 (1997).
Madura et al., "N-recognin/Ubc2 interactions in the N-end rule pathway," J Biol Chem. 268(16):12046-54 (1993).
Nagaoka et al., "Possible involvement of peptidylprolyl isomerase Pin1 in rheumatoid arthritis," Pathol Int. 61(2):59-66 (2011) (Abstract only).
Nakamura, et al. "Proline isomer-specific antibodies reveal the early pathogenic tau conformation in Alzheimer's disease" Cell. 149(1):232-44 (2012).
Nakazawa et al., "UV and skin cancer: specific p53 gene mutation in normal skin as a biologically relevant exposure measurement," Proc Natl Acad Sci U.S.A. 91(1):360-4 (1994).
Office Action for U.S. Appl. No. 14/334,052, mailed Nov. 20, 2014 (21 pages).
Orita et al., "Detection of polymorphisms of human DNA by gel electrophoresis as single-strand conformation polymorphisms," Proc Natl Acad Sci U.S.A. 86(8):2766-70 (1989).
Saiki et al., "Genetic analysis of amplified DNA with immobilized sequence-specific oligonucleotide probes," Proc Natl Acad Sci U.S.A. 86(16):6230-4 (1989).
Sanger et al., "DNA sequencing with chain-terminating inhibitors," Proc Natl Acad Sci U.S.A. 74(12):5463-7 (1977).
Scott et al. "Searching for peptide ligands with an epitope library," Science. 249(4967):386-90 (1990).
Terzic et al., "Inflammation and colon cancer," Gastroenterology 138(6):2101-14 (2010).
Tun-Kyi et al., "Essential role for the prolyl isomerase Pin1 in Toll-like receptor signaling and type I interferon-mediated immunity," Nat Immunol. 12(8):733-41 (2011).
Written Opinion of the International Searching Authority for International Application No. PCT/US2012/039850, mailed Oct. 3, 2012 (5 pages).
Wulf et al., "Pin1 is overexpressed in breast cancer and cooperates with Ras signaling in increasing the transcriptional activity of c-Jun towards cyclin D1," EMBO J. 20(13):3459-72 (2001).
Zuckermann et al., "Discovery of nanomolar ligands for 7-transmembrane G-protein-coupled receptors from a diverse N-(substituted)glycine peptoid library," J Med Chem. 37(17):2678-85 (1994).
"The genomic and transcriptomic architecture of 2,000 breast tumours reveals novel subgroups," available in PMC Dec. 21, 2012, published in final edited form as: Nature 486(7403):346-52 (2012) (15 pages).
Al-Hajj et al., "Prospective identification of tumorigenic breast cancer cells," Proc Natl Acad Sci U.S.A. 100(7):3983-8 (2003).
Bild et al., "Oncogenic pathway signatures in human cancers as a guide to targeted therapies," Nature. 439(7074):353-7 (2006).
Cerami et al., "The cBio cancer genomics portal: an open platform for exploring multidimensional cancer genomics data," Cancer Discov. 2(5):401-4 (2012).
Davis et al., "RAC1P29S is a spontaneously activating cancer-associated GTPase," Proc Natl Acad Sci U.S.A. 110(3):912-7 (2013).
Dontu et al., "In vitro propagation and transcriptional profiling of human mammary stem/progenitor cells," Genes Dev. 17(10):1253-70 (2003).
Elenbaas et al., "Human breast cancer cells generated by oncogenic transformation of primary mammary epithelial cells," Genes Dev. 15(1):50-65 (2001).
Extended European Search Report for European Patent Application No. 13800857.8, dated Dec. 1, 2015 (7 pages).
Forbes et al., "COSMIC: mining complete cancer genomes in the Catalogue of Somatic Mutations in Cancer," Nucleic Acids Res. 39:D945-50 (2011).

Ginestier et al., "Distinct and complementary information provided by use of tissue and DNA microarrays in the study of breast tumor markers," Am J Pathol. 161(4):1223-33 (2002).
International Preliminary Report on Patentability for International Patent Application No. PCT/US2015/021522, issued Sep. 21, 2016 (8 pages).
International Search Report and Written Opinion for International Application No. PCT/US15/21522, mailed Aug. 10, 2015 (19 pages).
International Search Report and Written Opinion for International Application No. PCT/US16/21759, mailed Aug. 12, 2016 (18 pages).
Kao et al., "Correlation of microarray-based breast cancer molecular subtypes and clinical outcomes: implications for treatment optimization," BMC Cancer. 11:143 (2011) (15 pages).
Keller et al., "Defining the cellular precursors to human breast cancer," Proc Natl Acad Sci U.S.A. 109(8):2772-7 (2012).
Kunju et al., "EZH2 and ALDH-1 mark breast epithelium at risk for breast cancer development," Mod Pathol. 24(6):786-93 (2011).
Lee et al., "Death-associated protein kinase 1 phosphorylates Pin1 and inhibits its prolyl isomerase activity and cellular function," Mol Cell. 42(2):147-59 (2011).
Liou et al., "Loss of Pin1 function in the mouse causes phenotypes resembling cyclin D1-null phenotypes," Proc Natl Acad Sci U.S.A. 99(3)1 335-40 (2002).
Luo et al., "Amplification and overexpression of CTTN (EMS1) contribute to the metastasis of esophageal squamous cell carcinoma by promoting cell migration and anoikis resistance," Cancer Res. 66(24):11690-9 (2006).
Luo et al., "Prolyl isomerase Pin1 acts downstream of miR200c to promote cancer stem-like cell traits in breast cancer," Cancer Res. 74(13):3603-16 (2014).
Mani et al., "The epithelial-mesenchymal transition generates cells with properties of stem cells," *Cell* 133: 704-715 (2008).
Mori et al., "A dual inhibitor against prolyl isomerase Pin1 and cyclophilin discovered by a novel real-time fluorescence detection method," Biochem Biophys Res Commun. 406(3):439-43 (2011).
Parker et al., "Supervised risk predictor of breast cancer based on intrinsic subtypes," J. Clin. Oncol. 27(8)1160-7 (2009).
Parulekar et al., "A randomized controlled trial to evaluate inhibition of T-cell costimulation in allergen-induced airway inflammation," Am J Respir Crit Care Med. 187(5):494-501 (2013).
Petruk et al., "TrxG and PcG proteins but not methylated histones remain associated with DNA through replication," Cell. 150(5):922-33 (2012).
Ranganathan et al., "Structural and functional analysis of the mitotic rotamase Pin1 suggests substrate recognition is phosphorylation dependent," Cell. 89(6):875-86 (1997).
Ryo et al., "Pin1 regulates turnover and subcellular localization of beta-catenin by inhibiting its interaction with APC," Nat Cell Biol. 3(9):793-801 (2001).
Schmidt et al., "The humoral immune system has a key prognostic impact in node-negative breast cancer," Cancer Res. 68(13):5405-13 (2008).
Yu et al. "Let-7 regulates self renewal and tumorigenicity of breast cancer cells," Cell. 131(6)1109-23 (2007).
Zhang et al., "Identification of tumor-initiating cells in a p53-null mouse model of breast cancer," Cancer Res. 68(12):4674-82 (2008).
International Preliminary Report on Patentability for International Application No. PCT/US2015/040771, issued Jan. 17, 2017 (9 pages).
International Preliminary Report on Patentability for International Patent Application No. PCT/US2013/044747, issued Dec. 9, 2014 (8 pages).
International Search Report and Written Opinion for International Application No. PCT/US15/40771, mailed Jun. 30, 2016 (13 pages).
Jäger et al., "Sequence determinants of thermodynamic stability in a WW domain—an all-beta-sheet protein," Protein Sci. 18(8):1806-13 (2009).
Ma et al., "A functional polymorphism in PIN1 that prevents its suppression by AP4 is associated with delayed onset of Alzheimer's

(56) References Cited

OTHER PUBLICATIONS disease," available in PMC Apr. 1, 2013, published in final edited form as: Neurobiol Aging. 33(4):804-13 (2012) (18 pages).
Eswaran et al., "Crystal structures and inhibitor identification for PTPN5, PTPRR and PTPN7: a family of human MAPK-specific protein tyrosine phosphatases," Biochem J. 395(3):483-91 (2006).
Nagaoka et al., "Possible involvement of peptidylprolyl isomerase Pin1 in rheumatoid arthritis," Pathol Int. 61(2):59-66 (2011).
Notice of Reasons for Rejection and English Translation for Japanese Patent Application No. 2015-516246, mailed Mar. 28, 2017 (12 pages).

\* cited by examiner

METHODS AND COMPOSITIONS FOR THE INHIBITION OF PIN1

CROSS-REFERENCE TO RELATED APPLICATIONS

This application claims benefit of U.S. Provisional Application No. 61/656,806, filed Jun. 7, 2012, which is hereby incorporated by reference in its entirety.

STATEMENT AS TO FEDERALLY SPONSORED RESEARCH

This invention was made with government support under grants DA031663 and CA167677 awarded by NIH numbers NIH R03DA031663 and R01CA167677. The government has certain rights in the invention.

FIELD OF THE INVENTION

In general, the invention relates to compositions and methods for inhibiting Pin1 and the treatment of disorders characterized by elevated Pin1 levels (e.g., immune disorders and proliferative disorders) with compounds defined herein.

BACKGROUND OF THE INVENTION

Immune disorders are characterized by the inappropriate activation of the body's immune defenses. Rather than targeting infectious invaders, the immune response targets and damages the body's own tissues or transplanted tissues. The tissue targeted by the immune system varies with the disorder. For example, in multiple sclerosis, the immune response is directed against the neuronal tissue, while in Crohn's disease the digestive tract is targeted.

Immune disorders affect millions of individuals and include conditions such as asthma, allergic intraocular inflammatory diseases, arthritis, atopic dermatitis, atopic eczema, diabetes, hemolytic anaemia, inflammatory dermatoses, inflammatory bowel or gastrointestinal disorders (e.g., Crohn's disease and ulcerative colitis), multiple sclerosis, myasthenia gravis, pruritis/inflammation, psoriasis, rheumatoid arthritis, cirrhosis, and systemic lupus erythematosus.

Current treatment regimens for immune disorders typically rely on immunosuppressive agents. The effectiveness of these agents can vary and their use is often accompanied by adverse side effects. Thus, improved therapeutic agents and methods for the treatment of autoimmune disorders are needed.

Additionally, the increased number of cancer cases reported in the United States, and, indeed, around the world, is a major concern. Currently there are only a handful of detection and treatment methods available for some specific types of cancer, and these provide no absolute guarantee of success. In order to be most effective, these treatments require not only an early detection of the malignancy, but a reliable assessment of the severity of the malignancy.

It is apparent that the complex process of tumor development and growth must involve multiple gene products. It is therefore important to define the role of specific genes involved in tumor development and growth and identify those genes and gene products that can serve as targets for the diagnosis, prevention, and treatment of cancers.

We and others have shown that Pin1 is prevalently overexpressed in human cancers and that high Pin1 marker levels correlate with poor clinical outcome in many cancers. In contrast, the Pin1 polymorphism that reduces Pin1 expression is associated with reduced cancer risk in humans. Significantly, Pin1 activates at least 19 oncogenes/growth enhancers, including β-catenin, cyclin D1, NF-κB, c-Jun, c-fos, AKT, A1B1, HER2/Neu, MCl-1, Notch, Raf-1, Stat3, c-Myb, Hbx, Tax, and v-rel, and also inactivates at least 12 tumor suppressors/growth inhibitors, including PML, SMRT, FOXOs, RARa, and Smad. Whereas Pin1 overexpression causes cell transformation and tumorigenesis, Pin1 knockdown inhibits cancer cell growth in cell cultures and mice. Pin1-null mice are highly resistant to tumorigenesis induced either by oncogenes such as activated Ras or HER2/Neu, or tumor suppressors such as p53. Thus, there is a need in the art for Pin1 inhibitors to suppress numerous oncogenic pathways simultaneously for treating aggressive and/or drug-resistant cancers.

SUMMARY OF THE INVENTION

The current invention features compositions and methods for inhibiting Pin1 by contacting the Pin1 protein with a Table 1 Compound. The Pin1 protein can be within a cell, e.g., a human cell, such as a diseased human cell. Table 1 Compounds can be administered in a therapeutically effective amount for treating a subject, e.g., human subject, suffering from or at risk of an immune disorder or a proliferative disorder.

In one aspect of the invention, the expression level of Pin1 marker in a subject maybe determined prior to administering a Table 1 Compound. The expression level of Pin1 marker level can be determined by collecting a sample, e.g., a tissue sample, such as a blood or biopsy sample, from the subject and analyzing the expression of the Pin1 marker using methods known in the art. A Table 1 Compound can be administered if the expression level of the Pin1 marker is elevated in the subject. The subject can have elevated Pin1 expression levels and can be suffering from an immune disease or a proliferative disease.

In another aspect of the invention, the expression level of Pin1 marker can be determined after administration of a Table 1 Compound for determining efficacy of treatment and disease prognosis. Elevated Pin1 marker level can be due to an inherited trait or a somatic mutation. In one embodiment of the invention, the Pin1 marker is reduced Ser71 phosphorylation of the Pin1 protein The sample used for determining Pin1 expression can be selected from the group consisting of blood, urine, tissue biopsies, lymph, saliva, phlegm, cerebrospinal fluid, and pus. Furthermore, the sample can be derived from a diseased tissue, e.g., a tumor biopsy or fractionated blood.

In one embodiment, the method of the invention can be used for treating an immune disorder in a subject, e.g., a human subject, by administering a Table 1 Compound to the subject in a therapeutically effective amount. The immune disorder can be any one or more selected from the group consisting of acne vulgaris; acute respiratory distress syndrome; Addison's disease; adrenocortical insufficiency; adrenogenital ayndrome; allergic conjunctivitis; allergic rhinitis; allergic intraocular inflammatory diseases, ANCA-associated small-vessel vasculitis; angioedema; ankylosing spondylitis; aphthous stomatitis; arthritis, asthma; atherosclerosis; atopic dermatitis; autoimmune disease; autoimmune hemolytic anemia; autoimmune hepatitis; Behcet's disease; Bell's palsy; berylliosis; bronchial asthma; bullous herpetiformis dermatitis; bullous pemphigoid; carditis; celiac disease; cerebral ischaemia; chronic obstructive pulmonary disease; cirrhosis; Cogan's syndrome; contact dermatitis; COPD; Crohn's disease; Cushing's syndrome; dermatomyositis; diabetes mellitus; discoid lupus erythematosus; eosinophilic fasciitis; epicondylitis; erythema nodosum; exfoliative dermatitis; fibromyalgia; focal glomerulosclerosis; giant cell arteritis; gout; gouty arthritis; graft-versus-host disease; hand eczema; Henoch-Schonlein purpura; herpes gestationis; hirsutism; hypersensitivity drug reactions; idiopathic cerato-scleritis; idiopathic pulmonary fibrosis; idiopathic thrombocytopenic purpura; inflammatory bowel or gastrointestinal disorders, inflammatory dermatoses; juvenile rheumatoid arthritis; laryngeal edema; lichen planus; Loeffler's syndrome; lupus nephritis; lupus vulgaris; lymphomatous tracheobronchitis; macular edema; multiple sclerosis; musculoskeletal and connective tissue disorder; myasthenia gravis; myositis; obstructive pulmonary disease; ocular inflammation; organ transplant rejection; osteoarthritis; pancreatitis; pemphigoid gestationis; pemphigus vulgaris; polyarteritis nodosa; polymyalgia rheumatica; primary adrenocortical insufficiency; primary biliary cirrhosis; pruritus scroti; pruritis/inflammation, psoriasis; psoriatic arthritis; Reiter's disease; relapsing polychondritis; rheumatic carditis; rheumatic fever; rheumatoid arthritis; rosacea caused by sarcoidosis; rosacea caused by scleroderma; rosacea caused by Sweet's syndrome; rosacea caused by systemic lupus erythematosus; rosacea caused by urticaria; rosacea caused by zoster-associated pain; sarcoidosis; scleroderma; segmental glomerulosclerosis; septic shock syndrome; serum sickness; shoulder tendinitis or bursitis; Sjogren's syndrome; Still's disease; stroke-induced brain cell death; Sweet's disease; systemic dermatomyositis; systemic lupus erythematosus; systemic sclerosis; Takayasu's arteritis; temporal arteritis; thyroiditis; toxic epidermal necrolysis; tuberculosis; type-1 diabetes; ulcerative colitis; uveitis; vasculitis; and Wegener's granulomatosis.

In another embodiment, the method of the invention can be used for treating a proliferative disorder in a subject by administering a Table 1 Compound to the subject in a therapeutically effective amount. The proliferative disorder can be any one or more selected from the group consisting of acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemi), Hodgkin's disease, non-Hodgkin's disease, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodenroglioma, schwannoma, meningioma, melanoma, neuroblastoma, and retinoblastoma.

In one embodiment, the method of the invention may further include the administration of a low dosage of a second therapeutic compound, e.g., an anti-inflammatory compound, anti-microbial compound, anti-viral compound, or an anti-cancer compound. The second therapeutic compound can be selected from the group consisting of corticosteroids, NSAIDs, COX-2 inhibitors, biologics, small molecule immunomodulators, non-steroidal immunophilin-dependent immunosuppressants, 5-amino salicylic acid, DMARDs, hydroxychloroquine sulfate, and penicillamine. Alternatively, the second therapeutic compound can be selected from the group consisting of microtubule inhibitors, topoisomerase inhibitors, platins, alkylating agents, and anti-metabolites. The second therapeutic compound can also be selected from the group consisting of 1-D-ribofuranosyl-1,2,4-triazole-3 carboxamide, 9→2-hydroxy-ethoxy methylguanine, adamantanamine, 5-iodo-2'-deoxyuridine, trifluorothymidine, interferon, adenine arabinoside, protease inhibitors, thymidine kinase inhibitors, sugar or glycoprotein synthesis inhibitors, structural protein synthesis inhibitors, attachment and adsorption inhibitors, and nucleoside analogues such as acyclovir, penciclovir, valacyclovir, and ganciclovir.

In yet another embodiment, the second therapeutic compound can be selected from the group consisting of MK-2206, ON 013105, RTA 402, BI 2536, Sorafenib, ISIS-STAT3Rx, a microtubule inhibitor, a topoisomerase inhibitor, a platin, an alkylating agent, an anti-metabolite, paclitaxel, gemcitabine, doxorubicin, vinblastine, etoposide, 5-fluorouracil, carboplatin, altretamine, aminoglutethimide, amsacrine, anastrozole, azacitidine, bleomycin, busulfan, carmustine, chlorambucil, 2-chlorodeoxyadenosine, cisplatin, colchicine, cyclophosphamide, cytarabine, cytoxan, dacarbazine, dactinomycin, daunorubicin, docetaxel, estramustine phosphate, floxuridine, fludarabine, gentuzumab, hexamethylmelamine, hydroxyurea, ifosfamide, imatinib, interferon, irinotecan, lomustine, mechlorethamine, melphalen, 6-mercaptopurine, methotrexate, mitomycin, mitotane, mitoxantrone, pentostatin, procarbazine, rituximab, streptozocin, tamoxifen, temozolomide, teniposide, 6-thioguanine, topotecan, trastuzumab, vincristine, vindesine, and/or vinorelbine.

In one embodiment, the invention features a pharmaceutical composition of a Table 1 Compound. The pharmaceutical composition can be formulated as a pill, ointment, cream, foam, capsule, or a liquid for administering to a subject.

By "Table 1 Compound" is meant any of the compounds listed in Table 1, or any compound falling within the corresponding generic formula as set forth below.

TABLE 1

| No. | STRUCTURE | Formula |
|---|---|---|
| 1 | 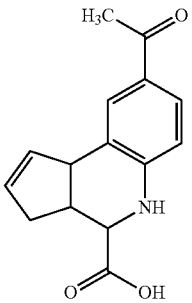 [SMILES: CC(=O)c1ccc2c(c1)C1C=CCC1C(C(=O)O)N2] | (I) |

TABLE 1-continued
| No. | STRUCTURE | Formula |
|---|---|---|
| 2 | 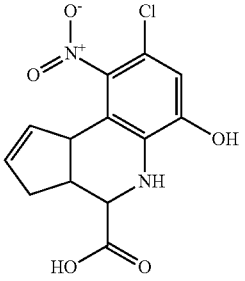 [SMILES: O=C(O)C1Nc2c(O)cc(Cl)c([N+](=O)[O-])c2C2C=CCC12] | (I) |
| 3 | 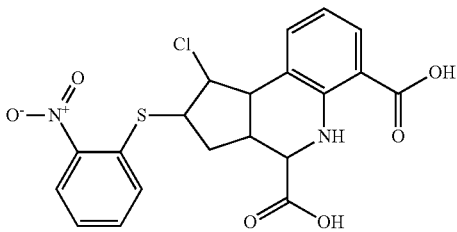 [SMILES: O=C(O)c1cccc2c1NC(C(=O)O)C1CC(Sc3ccccc3[N+](=O)[O-])C(Cl)C21] | (I) |
| 4 | 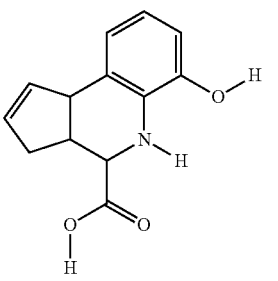 [SMILES: O=C(O)C1Nc2c(O)cccc2C2C=CCC12] | (I) |
| 5 | 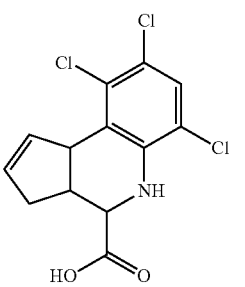 [SMILES: O=C(O)C1Nc2c(Cl)cc(Cl)c(Cl)c2C2C=CCC12] | (I) |
| 6 | 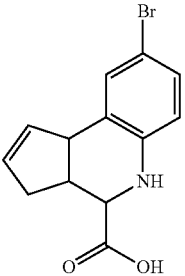 [SMILES: O=C(O)C1Nc2ccc(Br)cc2C2C=CCC12] | (I) |

TABLE 1-continued
| No. | STRUCTURE | Formula |
| --- | --- | --- |
| 7 | 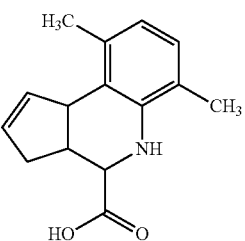 [SMILES: Cc1ccc(C)c2c1NC(C(=O)O)C1CC=CC21] | (I) |
| 8 | 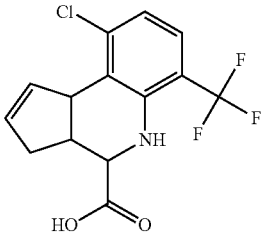 [SMILES: O=C(O)C1Nc2c(C(F)(F)F)ccc(Cl)c2C2C=CCC12] | (I) |
| 9 | 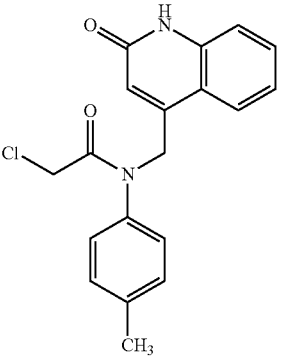 [SMILES: Cc1ccc(N(Cc2cc(=O)[nH]c3ccccc23)C(=O)CCl)cc1] | (II) |
| 10 | 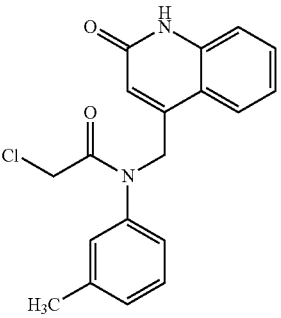 [SMILES: Cc1cccc(N(Cc2cc(=O)[nH]c3ccccc23)C(=O)CCl)c1] | (II) |
| 11 | 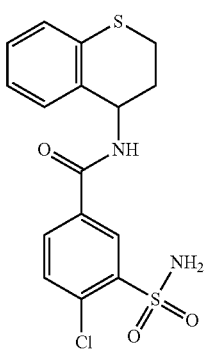 [SMILES: NS(=O)(=O)c1cc(C(=O)NC2CCSc3ccccc32)ccc1Cl] | |

TABLE 1-continued
| No. | STRUCTURE | Formula |
|---|---|---|
| 12 | 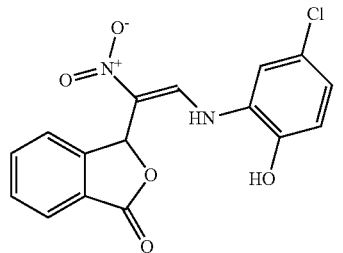 [SMILES: O=C1OC(/C(=C\Nc2cc(Cl)ccc2O)[N+](=O)[O-])c2ccccc21] | |
| 13 | 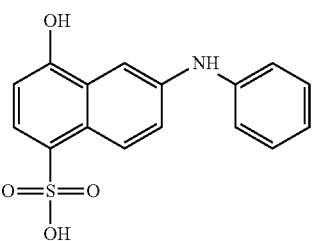 [SMILES: O=S(=O)(O)c1ccc(O)c2cc(Nc3ccccc3)ccc12] | (III) |
| 14 | 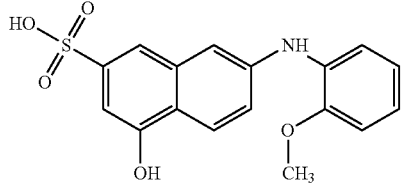 [SMILES: COc1ccccc1Nc1ccc2c(O)cc(S(=O)(=O)O)cc2c1] | (III) |
| 15 | 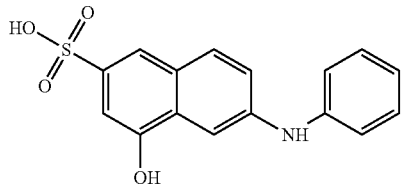 [SMILES: O=S(=O)(O)c1cc(O)c2cc(Nc3ccccc3)ccc2c1] | (III) |
| 16 | 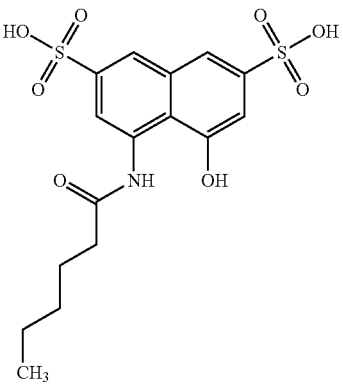 [SMILES: CCCCCC(=O)Nc1cc(S(=O)(=O)O)cc2cc(S(=O)(=O)O)cc(O)c12] | |
| 17 | 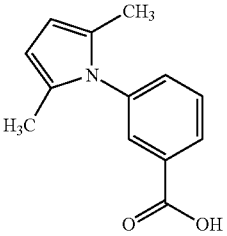 [SMILES: Cc1ccc(C)n1-c1cccc(C(=O)O)c1] | (IV) |

TABLE 1-continued

| No. | STRUCTURE | Formula |
|-----|-----------|---------|
| 18  | 2-(2,5-dimethyl-1H-pyrrol-1-yl)thiophene-3-carboxylic acid | (IV) |
| 19  | (E)-4-(3-(furan-2-yl)acrylamido)butanoic acid | |
| 20  | 5-(morpholine-4-carbonyl)-2H-pyran-2-one | |
| 21  | 2-(5-(2,3-dihydrobenzo[b][1,4]dioxin-6-yl)-2-methylfuran-3-carboxamido)-3-phenylpropanoic acid | |
| 22  | 7-nitro-1H-indole-2-carboxylic acid | |
| 23  | 2-(4-hydroxy-1H-indol-3-yl)acetic acid | |
| 24  | 2,5-dichloro-N-(4-(3-chlorothiophen-2-yl)thiazol-2-yl)benzenesulfonamide | |

TABLE 1-continued
| No. | STRUCTURE | Formula |
|---|---|---|
| 25 | 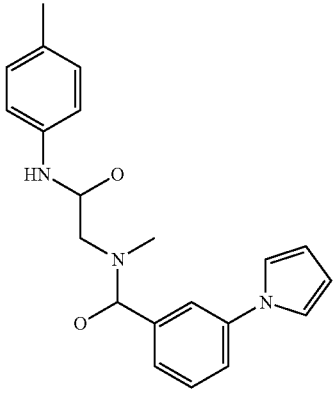 [SMILES: Cc1ccc(NC(O)CN(C)C(O)c2cccc(-n3cccc3)c2)cc1] | |
| 26 | 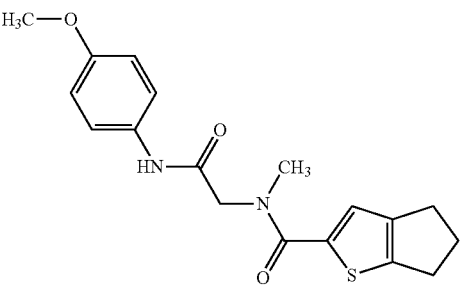 [SMILES: COc1ccc(NC(=O)CN(C)C(=O)c2cc3c(s2)CCC3)cc1] | |
| 27 | 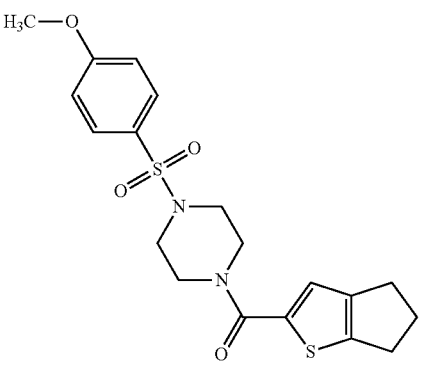 [SMILES: COc1ccc(S(=O)(=O)N2CCN(C(=O)c3cc4c(s3)CCC4)CC2)cc1] | |
| 28 | 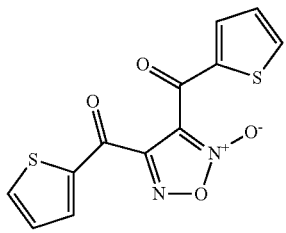 [SMILES: O=C(c1cccs1)c1no[n+]([O-])c1C(=O)c1cccs1] | (V) |

TABLE 1-continued

| No. | STRUCTURE | Formula |
|-----|-----------|---------|
| 29  | (structure: furazan N-oxide with two 4-methylphenyl ketone substituents) | (V) |
| 30  | (structure: furazan N-oxide with two (1,5-dimethyl-1H-pyrazol-4-yl)carbonyl substituents) | (V) |
| 31  | (structure: furazan N-oxide with thiophene-2-carbonyl and cyano substituents) | (V) |
| 32  | (structure: furazan N-oxide with two 4-methoxyphenyl ketone substituents) | (V) |

TABLE 1-continued
| No. | STRUCTURE | Formula |
|---|---|---|
| 33 | 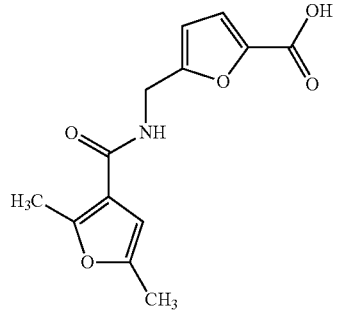 [SMILES: Cc1cc(C(=O)NCc2ccc(C(=O)O)o2)c(C)o1] | |
| 34 | 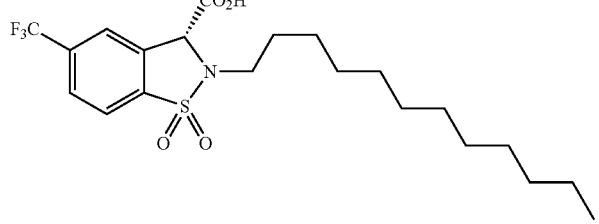 | |
| 35 | 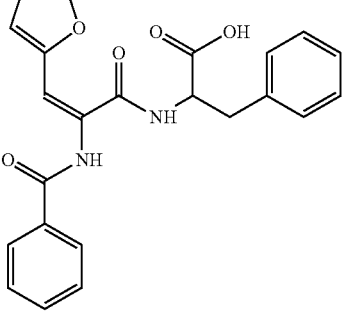 | |
| 36 | 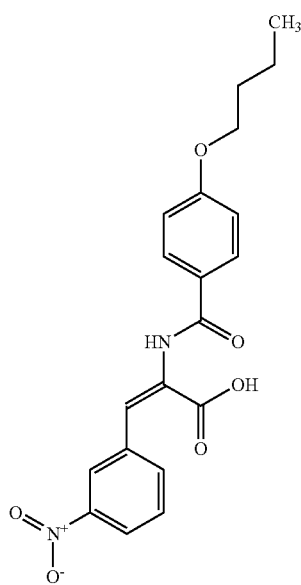 [SMILES: CCCCOc1ccc(C(=O)N/C(=C/c2cccc([N+](=O)[O-])c2)C(=O)O)cc1] | |

TABLE 1-continued
| No. | STRUCTURE | Formula |
|-----|-----------|---------|
| 37 | 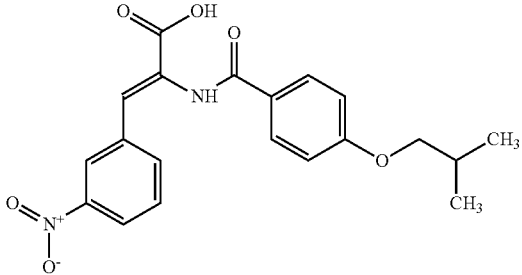 [SMILES: CC(C)COc1ccc(C(=O)N/C(=C\c2cccc([N+](=O)[O-])c2)C(=O)O)cc1] | |
| 38 | 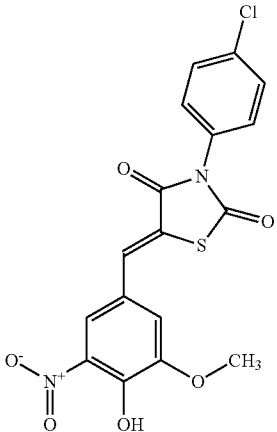 [SMILES: COc1cc(/C=C2\SC(=O)N(c3ccc(Cl)cc3)C2=O)cc([N+](=O)[O-])c1O] | |
| 39 | 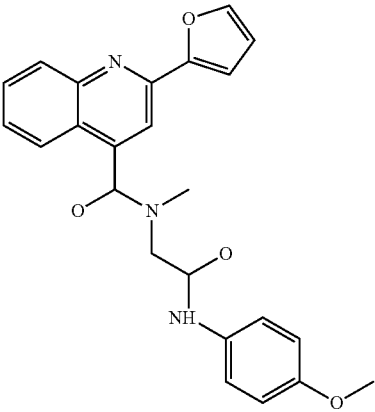 [SMILES: COc1ccc(NC(O)CN(C)C(O)c2cc(-c3ccco3)nc3ccccc23)cc1] | |

TABLE 1-continued
| No. | STRUCTURE | Formula |
|---|---|---|
| 40 | 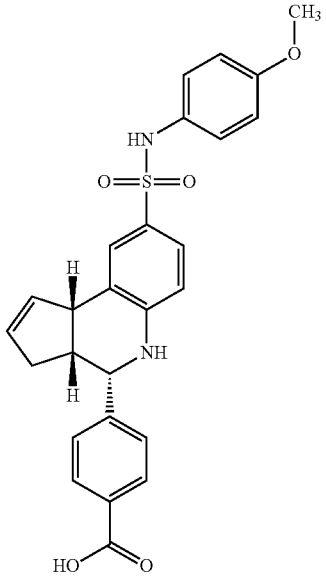 [SMILES: COc1ccc(NS(=O)(=O)c2ccc3c(c2)[C@H]2C=CC[C@H]2[C@@H](c2ccc(C(=O)O)cc2)N3)cc1] | |
| 41 | 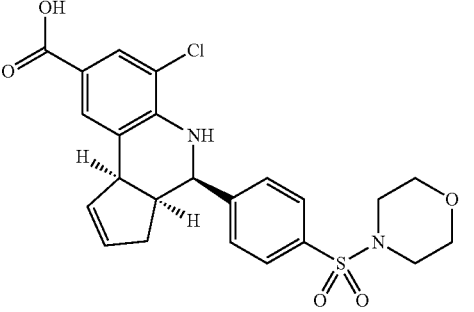 [SMILES: O=C(O)c1cc(Cl)c2c(c1)[C@@H]1C=CC[C@@H]1[C@H](c1ccc(S(=O)(=O)N3CCOCC3)cc1)N2] | |
| 42 | 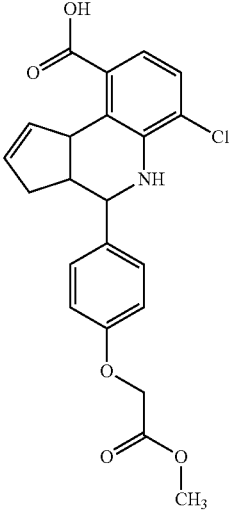 [SMILES: COC(=O)COc1ccc(C2Nc3c(Cl)ccc(C(=O)O)c3C3C=CCC32)cc1] | |

TABLE 1-continued
| No. | STRUCTURE | Formula |
|---|---|---|
| 43 | 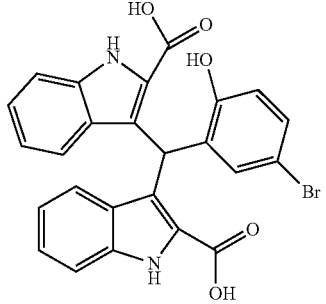 [SMILES: O=C(O)c1[nH]c2ccccc2c1C(c1cc(Br)ccc1O)c1c(C(=O)O)[nH]c2ccccc12] | |
| 44 | 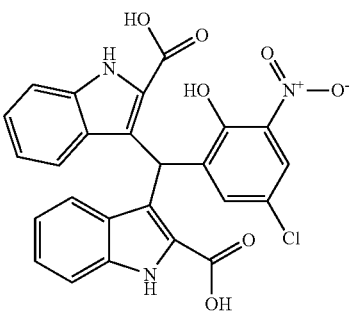 [SMILES: O=C(O)c1[nH]c2ccccc2c1C(c1cc(Cl)cc([N+](=O)[O-])c1O)c1c(C(=O)O)[nH]c2ccccc12] | |
| 45 | 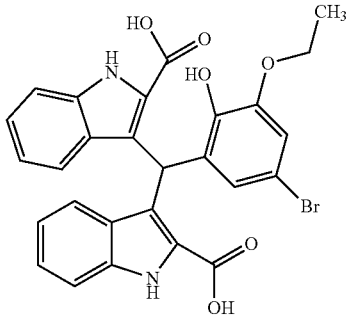 [SMILES: CCOc1cc(Br)cc(C(c2c(C(=O)O)[nH]c3ccccc23)c2c(C(=O)O)[nH]c3ccccc23)c1O] | |
| 46 | 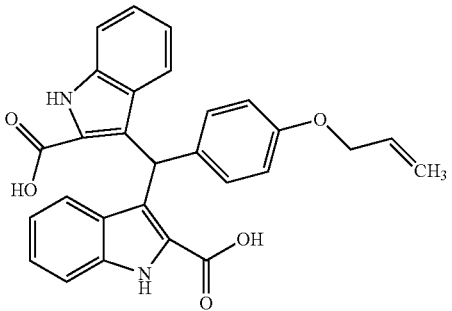 [SMILES: C=CCOc1ccc(C(c2c(C(=O)O)[nH]c3ccccc23)c2c(C(=O)O)[nH]c3ccccc23)cc1] | |
| 47 | 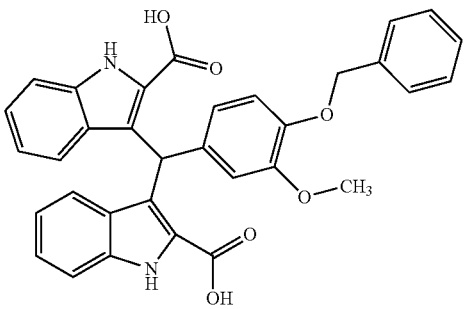 [SMILES: COc1cc(C(c2c(C(=O)O)[nH]c3ccccc23)c2c(C(=O)O)[nH]c3ccccc23)ccc1OCc1ccccc1] | |

TABLE 1-continued

| No. | STRUCTURE | Formula |
|---|---|---|
| 48 | 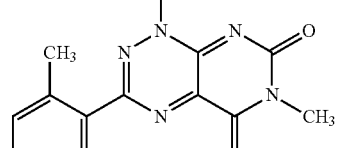 | |
| 49 | 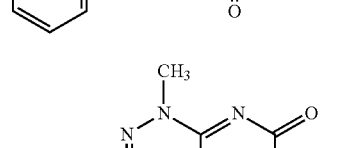 | |
| 50 | 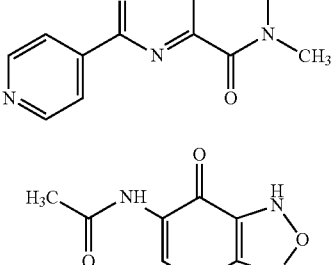 | |

In some embodiments, the compound has a structure according to the following formula,

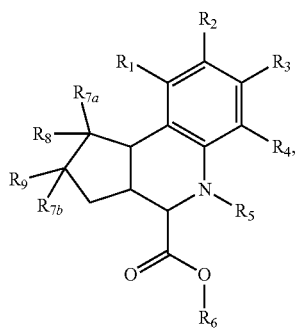

(I)

or a stereoisomer thereof, or a pharmaceutically acceptable salt thereof, where each of $R_1$, $R_2$, $R_3$, and $R_4$ is, independently, H, optionally substituted C1-C6 alkyl, OH, optionally substituted C1-C6 alkoxy, halogen, nitro, optionally substituted C1-C6 acyl, or $CO_2R_{10}$;

each of $R_5$, $R_6$, and $R_{10}$ is, independently, H or optionally substituted C1-C6 alkyl;

$R_{7a}$ and $R_{7b}$ are both H, or $R_{7a}$ and $R_{7b}$ combine to form a carbon-carbon double bond; and each of $R_8$ and $R_9$ is, independently, H, optionally substituted C1-C6 alkyl, OH, optionally substituted C1-C6 alkoxy, optionally substituted aryloxy, SH, optionally substituted thioaryloxy, halogen, optionally substituted C1-C6 acyl.

In some embodiments, not more than one of $R_1$-$R_4$ can be nitro.

In some embodiments, at least one of $R_1$-$R_4$ is OH, halogen (e.g., F, Cl, or Br), optionally substituted C1-C6 alkyl (e.g., $CH_3$ or $CF_3$), optionally substituted C1-C6 acyl (e.g., $CO_2Me$) or $CO_2R_{10}$ (e.g., $CO_2H$).

In some embodiments, 1, 2, or 3 of $R_1$-$R_4$ is halogen (e.g., F, Cl, or Br).

In some embodiments, $R_5$ and $R_6$ are both H.

In some embodiments, $R_{7a}$ and $R_{7b}$ combine to form a carbon-carbon double bond. In further embodiments, both $R_8$ and $R_9$ are H.

In some embodiments, $R_{7a}$ and $R_{7b}$ are both H.

In some embodiments, the compound is any of Compounds 1-8 of Table 1.

In some embodiments, the compound has a structure according to the following formula,

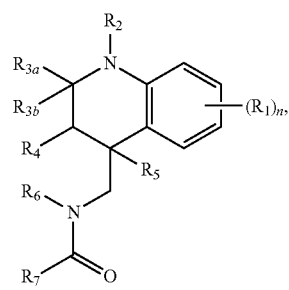

(II)

or a stereoisomer thereof, or a pharmaceutically acceptable salt thereof, wherein n is 0, 1, 2, 3, or 4;

each $R_1$, when present, is, independently, optionally substituted C1-C6 alkyl, OH, optionally substituted C1-C6 alkoxy, halogen, nitro, or optionally substituted C1-C6 acyl;

$R_2$ is H or optionally substituted C1-C6 alkyl; $R_{3a}$ and $R_{3b}$ are both H, or $R_{3a}$ and $R_{3b}$ combine to form a carbon-oxygen double bond;

$R_4$ and $R_5$ are both H, or $R_4$ and $R_5$ combine to form a carbon-carbon double bond;

$R_6$ is optionally substituted phenyl; and $R_7$ is optionally substituted C1-C6 alkyl.

In some embodiments, n is 0. In other embodiments, $R_{3a}$ and $R_{3b}$ combine to form a carbon-oxygen double bond. In still other embodiments, $R_2$ is H. In certain embodiments, $R_4$ and $R_5$ combine to form a carbon-carbon double bond. In other embodiments, $R_7$ is optionally substituted Cl alkyl (e.g., $CH_2Cl$). In other embodiments, $R_6$ is phenyl having 1, 2, 3, 4, or 5 substituents (e.g., $R_6$ is tolyl).

In some embodiments, the compound is any of compounds 9-10 in table 1.

In some embodiments, the compound has a structure according to the following formula,

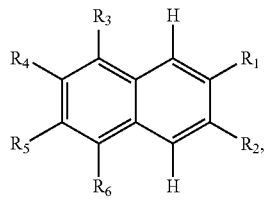

(III)

or a stereoisomer thereof, or a pharmaceutically acceptable salt thereof, where one of $R_1$ and $R_2$ is H, and the other is —NH(optionally substituted phenyl); and each of $R_3$, $R_4$, $R_5$, and $R_6$ is, independently, H, $OR_7$, or $SO_3R_8$;

each of $R_7$ and $R_8$ is, independently, H or optionally substituted C1-C6 alkyl; and wherein one and only one of $R_3$, $R_4$, $R_5$, and $R_6$ is $SO_3R_8$, and wherein one and only one of $R_3$, $R_4$, $R_5$, and $R_6$ is $OR_7$.

In some embodiments, the optionally substituted phenyl has 1, 2, 3, 4, or 5 substituents. In other embodiments, the phenyl is unsubstituted.

In some embodiments, one of $R_3$ or $R_6$ is OH, and one of $R_4$ or $R_5$ is $SO_3R_8$ (e.g., $SO_3H$).

In some embodiments, the compound is one of Compounds 13-15 of Table 1.

In some embodiments, the compound has a structure according to the following formula,

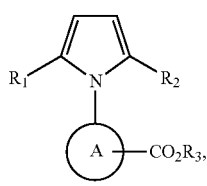

(IV)

or a stereoisomer thereof, or a pharmaceutically acceptable salt thereof, where each of $R_1$ and $R_2$ is, independently, optionally substituted C1-C6 alkyl; and A is a phenyl or 5-membered heteroaryl comprising a carboxyl substituent according to the substructure $CO_2R_3$, and where A comprises 0, 1, 2, or 3 substituent groups.

In some embodiments, each of $R_1$ and $R_2$ is, independently, unsubstituted C1-C6 alkyl (e.g., $CH_3$).

In other embodiments, the $CO_2R_3$ substituent is adjacent to the atom of substructure A that is covalently attached to the pyrrole nitrogen. In other embodiments, when A is phenyl, the $CO_2R_3$ substituent may be ortho, meta, or para to the pyrrole group.

In still other embodiments, $R_3$ is H.

In certain embodiments, A is phenyl or thienyl.

In some embodiments, the compound is any of compounds 17-19 of Table 1.

In still other embodiments, the compound has a structure according to the following formula,

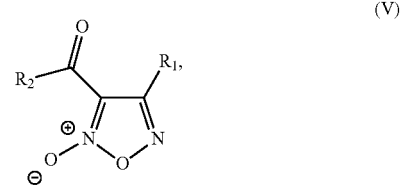

(V)

or a stereoisomer thereof, or a pharmaceutically acceptable salt thereof, where $R_1$ is CN or $C(\!\!=\!\!O)R_3$; and each $R_2$ and $R_3$ is, independently, optionally substituted phenyl or an optionally substituted 5-to-6-membered heteroaryl.

In some embodiments, $R_1$ is $C(\!\!=\!\!O)R_3$. In further embodiments, both $R_2$ and $R_3$ are the same group. In some embodiments, both $R_2$ and $R_3$ are phenyl having 0, 1, 2, or 3 substituents (e.g., methyl or methoxy). In other embodiments, both $R_2$ and $R_3$ are optionally substituted five-membered heteroaryls (e.g., optionally substituted pyrazolyl groups).

In some embodiments, $R_1$ is CN. In further embodiments, $R_3$ is an optionally substituted five-membered heteroaryl group (e.g., thienyl).

In some embodiments, the compound is any of compounds 28-32 of Table 1.

As used herein, the term "C1-C6 alkoxy" represents a chemical substituent of formula —OR, where R is an optionally substituted C1-C6 alkyl group, unless otherwise specified. In some embodiments, the alkyl group can be substituted, e.g., the alkoxy group can have 1, 2, 3, 4, 5 or 6 substituent groups as defined herein.

As used herein, the term "C1-C6 acyl" refers to a C1-C6 alkyl group that includes a $C(\!\!=\!\!O)$ moiety and which may be further substituted as described herein.

As used herein, the term "alkyl," "alkenyl" and "alkynyl" include straight-chain, branched-chain and cyclic monovalent substituents, as well as combinations of these, containing only C and H when unsubstituted. Examples include methyl, ethyl, isobutyl, cyclohexyl, cyclopentylethyl, 2-propenyl, 3-butynyl, and the like. The term "cycloalkyl," as used herein, represents a monovalent saturated or unsaturated non-aromatic cyclic alkyl group having between three to nine carbons (e.g., a C3-C9 cycloalkyl), unless otherwise specified, and is exemplified by cyclopropyl, cyclobutyl, cyclopentyl, cyclohexyl, cycloheptyl, bicyclo[2.2.1.]heptyl, and the like. When the cycloalkyl group includes one carbon-carbon double bond, the cycloalkyl group can be referred to as a "cycloalkenyl" group. Exemplary cycloalkenyl groups include cyclopentenyl, cyclohexenyl, and the like.

Typically, the alkyl, alkenyl and alkynyl groups contain 1-12 carbons (e.g., C1-C12 alkyl) or 2-12 carbons (e.g., C2-C12 alkenyl or C2-C12 alkynyl). In some embodiments, the alkyl groups are C1-C8, C1-C6, C1-C4, C1-C3, or C1-C2 alkyl groups; or C2-C8, C2-C6, C2-C4, or C2-C3 alkenyl or alkynyl groups. Further, any hydrogen atom on one of these groups can be replaced with a substituent as described herein.

"Aromatic" moiety or "aryl" moiety refers to any monocyclic or fused ring bicyclic system which has the characteristics of aromaticity in terms of electron distribution throughout the ring system and includes a monocyclic or fused bicyclic moiety such as phenyl or naphthyl; "heteroaromatic" or "heteroaryl" also refers to such monocyclic or fused bicyclic ring systems containing one or more heteroatoms selected from O, S and N. The inclusion of a heteroatom permits inclusion of 5-membered rings to be considered aromatic as well as 6-membered rings. Thus, typical aromatic/heteroaromatic systems include pyridyl, pyrimidyl, indolyl, benzimidazolyl, benzotriazolyl, isoquinolyl, quinolyl, benzothiazolyl, benzofuranyl, thienyl, furyl, pyrrolyl, thiazolyl, oxazolyl, isoxazolyl, benzoxazolyl, benzoisoxazolyl, imidazolyl and the like. Because tautomers are theoretically possible, phthalimido is also considered aromatic. Typically, the ring systems contain 5-12 ring member atoms or 6-10 ring member atoms. In some embodiments, the aromatic or heteroaromatic moiety is a 6-membered aromatic rings system optionally containing 1-2 nitrogen atoms. More particularly, the moiety is an optionally substituted phenyl, pyridyl, indolyl, pyrimidyl, pyridazinyl, benzothiazolyl or benzimidazolyl, pyrazolyl, imidazolyl, isoxazolyl, thiazolyl, benzothiazolyl, indolyl. Even more particularly, such moiety is phenyl, pyridyl, or pyrimidyl and even more particularly, it is phenyl.

As used herein, the term "aryloxy" refers to aromatic or heteroaromatic systems which are coupled to another residue through an oxygen atom. A typical example of an O-aryl is phenoxy. Similarly, "thioaryloxy" refers to aromatic or heteroaromatic systems which are coupled to another residue through a sulfur atom.

As used herein, a halogen is selected from F, Cl, Br, and I, and more particularly it is fluoro or chloro.

In general, a substituent group (e.g., alkyl, alkenyl, alkynyl, or aryl (including all heteroforms defined above) may itself optionally be substituted by additional substituents. The nature of these substituents is similar to those recited with regard to the substituents on the basic structures above. Thus, where an embodiment of a substituent is alkyl, this alkyl may optionally be substituted by the remaining substituents listed as substituents where this makes chemical sense, and where this does not undermine the size limit of alkyl per se; e.g., alkyl substituted by alkyl or by alkenyl would simply extend the upper limit of carbon atoms for these embodiments, and is not included. For example, where a group is substituted, the group may be substituted with 1, 2, 3, 4, 5, or 6 substituents. Optional substituents include, but are not limited to: C1-C6 alkyl or heteroaryl, C2-C6 alkenyl or heteroalkenyl, C2-C6 alkynyl or heteroalkynyl, halogen; aryl, heteroaryl, azido(—N$_3$), nitro (—NO$_2$), cyano (—CN), acyloxy(—OC(=O)R'), acyl (—C(=O)R'), alkoxy (—OR'), amido (—NR'C(=O)R" or —C(=O)NRR'), amino (—NRR'), carboxylic acid (—CO$_2$H), carboxylic ester (—CO$_2$R'), carbamoyl (—OC(=O)NR'R" or —NRC(=O)OR'), hydroxy (—OH), isocyano (—NC), sulfonate (—S(=O)$_2$OR), sulfonamide (—S(=O)$_2$NRR' or —NRS(=O)$_2$R'), or sulfonyl (—S(=O)$_2$R), where each R or R' is selected, independently, from H, C1-C6 alkyl or heteroaryl, C2-C6 alkenyl or heteroalkenyl, 2C-6C alkynyl or heteroalkynyl, aryl, or heteroaryl. A substituted group may have, for example, 1, 2, 3, 4, 5, 6, 7, 8, or 9 substituents.

Typical optional substituents on aromatic or heteroaromatic groups include independently halo, CN, NO$_2$, CF$_3$, OCF$_3$, COOR', CONR'$_2$, OR', SR', SOR', SO$_2$R', NR'$_2$, NR'(CO)R',NR'C(O)OR', NR'C(O)NR'$_2$, NR'SO$_2$NR'$_2$, or NR'SO$_2$R', wherein each R' is independently H or an optionally substituted group selected from alkyl, alkenyl, alkynyl, heteroalkyl, heteroalkenyl, heteroalkynyl, heteroaryl, and aryl (all as defined above); or the substituent may be an optionally substituted group selected from alkyl, alkenyl, alkynyl, heteroalkyl, heteroalkenyl, heteroalkynyl, aryl, heteroaryl, O-aryl, O-heteroaryl and arylalkyl.

Optional substituents on a non-aromatic group (e.g., alkyl, alkenyl, and alkynyl groups), are typically selected from the same list of substituents suitable for aromatic or heteroaromatic groups, except as noted otherwise herein. A non-aromatic group may also include a substituent selected from =O and =NOR' where R' is H or an optionally substituted group selected from alkyl, alkenyl, alkynyl, heteroalkyl, heteroalkenyl, heteralkynyl, heteroaryl, and aryl (all as defined above).

The term "pharmaceutically acceptable salt," as use herein, represents those salts of the compounds described here (e.g., a compound according to any of Formulas (I)-(V) or any of Compounds (1)-(50) of Table 1) that are, within the scope of sound medical judgment, suitable for use in contact with the tissues of humans and animals without undue toxicity, irritation, allergic response and the like and are commensurate with a reasonable benefit/risk ratio. Pharmaceutically acceptable salts are well known in the art. For example, pharmaceutically acceptable salts are described in: Berge et al., *J. Pharmaceutical Sciences* 66:1-19, 1977 and in *Pharmaceutical Salts: Properties, Selection, and Use*, (Eds. P. H. Stahl and C. G. Wermuth), Wiley-VCH, 2008. The salts can be prepared in situ during the final isolation and purification of the compounds described herein or separately by reacting the free base group with a suitable organic acid.

The compounds of the invention may have ionizable groups so as to be capable of preparation as pharmaceutically acceptable salts. These salts may be acid addition salts involving inorganic or organic acids or the salts may, in the case of acidic forms of the compounds of the invention be prepared from inorganic or organic bases. Frequently, the compounds are prepared or used as pharmaceutically acceptable salts prepared as addition products of pharmaceutically acceptable acids or bases. Suitable pharmaceutically acceptable acids and bases are well-known in the art, such as hydrochloric, sulphuric, hydrobromic, acetic, lactic, citric, or tartaric acids for forming acid addition salts, and potassium hydroxide, sodium hydroxide, ammonium hydroxide, caffeine, various amines, and the like for forming basic salts. Methods for preparation of the appropriate salts are well-established in the art.

Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts and the like. Representative alkali or alkaline earth metal salts include sodium, lithium, potassium, calcium, magnesium and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine and the like.

In some cases, the compounds of the invention contain one or more chiral centers. The invention includes each of the isolated stereoisomeric forms as well as mixtures of stereoisomers in varying degrees of chiral purity, including racemic mixtures. It also encompasses the various diastereomers and tautomers that can be formed.

The compounds described herein can be prepared according to conventional means known in the art.

By the term "immune disorder" is meant a disorder characterized by deregulation of Toll like receptor and/or type 1 interferon.

By the term "proliferative disorder" is meant a disorder characterized by inappropriate accumulation of a cell population in a tissue (e.g., by abnormal cell growth). This inappropriate accumulation may be the result of a genetic or epigenetic variation that occurs in one or more cells of the cell population. This genetic or epigenetic variation causes the cells of the cell population to grow faster, die slower, or differentiate slower than the surrounding, normal tissue. The cell population includes cells of hematopoietic, epithelial, endothelial, or solid tissue origin.

As used herein, the term "Pin1 marker" refers to a marker which is capable of being indicative of Pin1 activity levels in an organism or a sample of the invention. Pin1 markers include nucleic acid molecules (e.g., mRNA, DNA) which correspond to some or all of a Pin1 gene, peptide sequences (e.g., amino acid sequences) which correspond to some or all of a Pin1 protein, nucleic acid sequences which are homologous to Pin1 gene sequences, peptide sequences which are homologous to Pin1 peptide sequences, antibodies to Pin1 protein, substrates of Pin1 protein, binding partners of Pin1 protein, and activity of Pin1.

By "elevated levels of a Pin1 marker" is meant a level of Pin1 marker that is altered thereby indicating elevated Pin1 activity. "Elevated levels of a Pin1 marker" include levels at least 5%, 6%, 7%, 8%, 9%, 10%, 15%, 20%, 25%, 30%, 40%, 50%, 60%, 70%, 80%, 90%, 100%, 200%, 500%, 1000%, or greater than, or 5%, 6%, 7%, 8%, 9%, 10%, 15%, 20%, 25%, 30%, 40%, 50%, 60%, 70%, 80%, 90%, 100% less than the marker levels measured in a normal, disease fee subject or tissue.

By "corticosteroid" is meant any naturally occurring or synthetic steroid hormone which can be derived from cholesterol and is characterized by a hydrogenated cyclopentanoperhydrophenanthrene ring system. Naturally occurring corticosteroids are generally produced by the adrenal cortex. Synthetic corticosteroids may be halogenated. Functional groups required for activity include a double bond at A4, a C3 ketone, and a C20 ketone. Corticosteroids may have glucocorticoid and/or mineralocorticoid activity. In preferred embodiments, the corticosteroid is either fludrocortisone or prednisolone.

Exemplary corticosteroids include algestone, 6-alpha-fluoroprednisolone, 6-alpha-methylprednisolone, 6-alpha-methylprednisolone 21-acetate, 6-alpha-methylprednisolone 21-hemisuccinate sodium salt, 6-alpha,9-alpha-difluoroprednisolone 21-acetate 17-butyrate, amcinafal, beclomethasone, beclomethasone dipropionate, beclomethasone dipropionate monohydrate, 6-beta-hydroxycortisol, betamethasone, betamethasone-17-valerate, budesonide, clobetasol, clobetasol propionate, clobetasone, clocortolone, clocortolone pivalate, cortisone, cortisone acetate, cortodoxone, deflazacort, 21-deoxycortisol, deprodone, descinolone, desonide, desoximethasone, dexamethasone, dexamethasone-21-acetate, dichlorisone, diflorasone, diflorasone diacetate, diflucortolone, doxibetasol, fludrocortisone, flumethasone, flumethasone pivalate, flumoxonide, flunisolide, fluocinonide, fluocinolone acetonide, 9-fluorocortisone, fluorohydroxyandrostenedione, fluorometholone, fluorometholone acetate, fluoxymesterone, flupredidene, fluprednisolone, flurandrenolide, formocortal, halcinonide, halometasone, halopredone, hyrcanoside, hydrocortisone, hydrocortisone acetate, hydrocortisone butyrate, hydrocortisone cypionate, hydrocortisone sodium phosphate, hydrocortisone sodium succinate, hydrocortisone probutate, hydrocortisone valerate, 6-hydroxydexamethasone, isoflupredone, isoflupredone acetate, isoprednidene, meclorisone, methylprednisolone, methylprednisolone acetate, methylprednisolone sodium succinate, paramethasone, paramethasone acetate, prednisolone, prednisolone acetate, prednisolone metasulphobenzoate, prednisolone sodium phosphate, prednisolone tebutate, prednisolone-21-hemisuccinate free acid, prednisolone-21-acetate, prednisolone-21(beta-D-glucuronide), prednisone, prednylidene, procinonide, tralonide, triamcinolone, triamcinolone acetonide, triamcinolone acetonide 21-palmitate, triamcinolone diacetate, triamcinolone hexacetonide, and wortmannin. Desirably, the corticosteroid is fludrocortisone or prednisolone.

"Treatment," as used herein, refers to the application or administration of a therapeutic agent (e.g., a Table 1 Compound) to a patient, or application or administration of a therapeutic agent to an isolated tissue or cell line from a patient, who has a disease, a symptom of disease or a predisposition toward a disease, with the purpose to cure, heal, alleviate, relieve, alter, remedy, ameliorate, improve or affect the disease, the symptoms of disease or the predisposition toward disease, or to slow the progression of the disease.

As used herein, the terms "sample" and "biological sample" include samples obtained from a mammal or a subject containing Pin1 which can be used within the methods described herein, e.g., tissues, cells and biological fluids isolated from a subject, as well as tissues, cells and fluids present within a subject. Typical samples from a subject include tissue samples, tumor samples, blood, urine, biopsies, lymph, saliva, phlegm, cerebrospinal fluid, pus, and the like. The sample can be from a diseased tissue such as a tumor biopsy or fractionated blood.

By a "low dosage" or "low concentration" is meant at least 5% less (e.g., at least 10%, 20%, 50%, 80%, 90%, or even 95%) than the lowest standard recommended dosage or lowest standard recommended concentration of a particular compound formulated for a given route of administration for treatment of any human disease or condition. For example, a low dosage of an anti-inflammatory, anti-microbial, or anti-viral compound formulated for oral administration will differ from a low dosage of an anti-inflammatory, anti-microbial, or anti-viral compound formulated for intravenous administration.

Each of FIGS. 3A-3D is a series of compounds tested in a Pin1 competition fluorescence polarization assay together with the chemical structures of a subset of these compounds and curves relating to the performance of those compounds for which chemical structures are shown in the assay. A set of assayed compounds is identified in the list shown on the left of each of FIGS. 3A-3D. Chemical structures of a subset of the listed compounds are shown to the right of the list, and the performance each compound for which a chemical structure is shown is visualized in the two curves to the right of the chemical structure. The curve closest to each chemical structure shows the relationship between log concentration (M) of the compound (X axis) and the emission of polarized fluorescence (Y axis), shown as percentage change in comparison to the emission of polarized fluorescence by an uninhibited control. The rightmost set of curves shows the relationship between log concentration (M) of the compound (X axis) and total fluorescence intensity (Y axis). Pin1 inhibitors in FIG. 3A demonstrate no interference of total fluorescence. Pin1 inhibitors in FIG. 3B may demonstrate interference of total fluorescence. Pin1 inhibitors in FIG. 3C demonstrate strong interference of total fluorescence. Pin1 inhibitors in FIG. 3D possibly quench total fluorescence.

Figure 4:
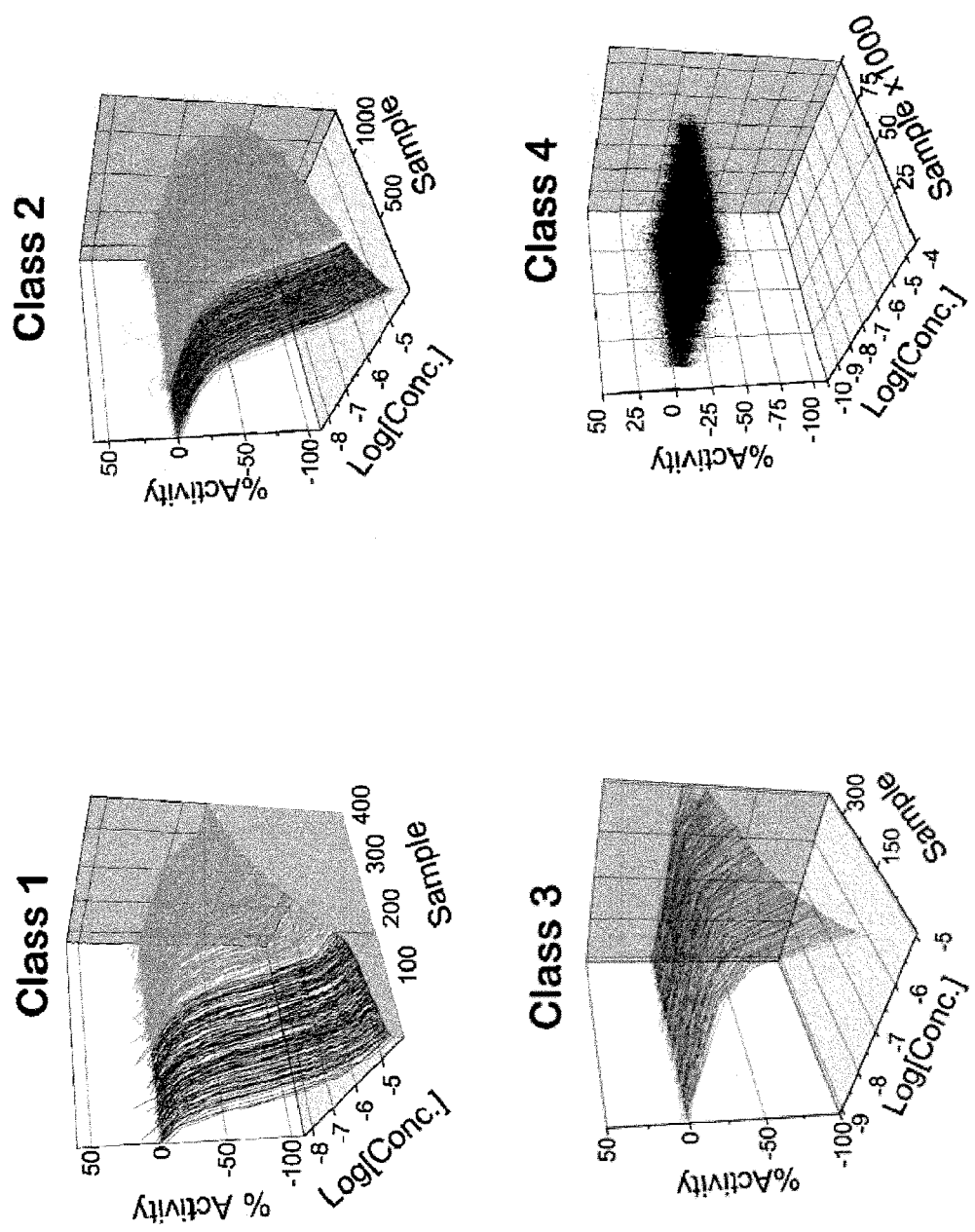
Figure 4:
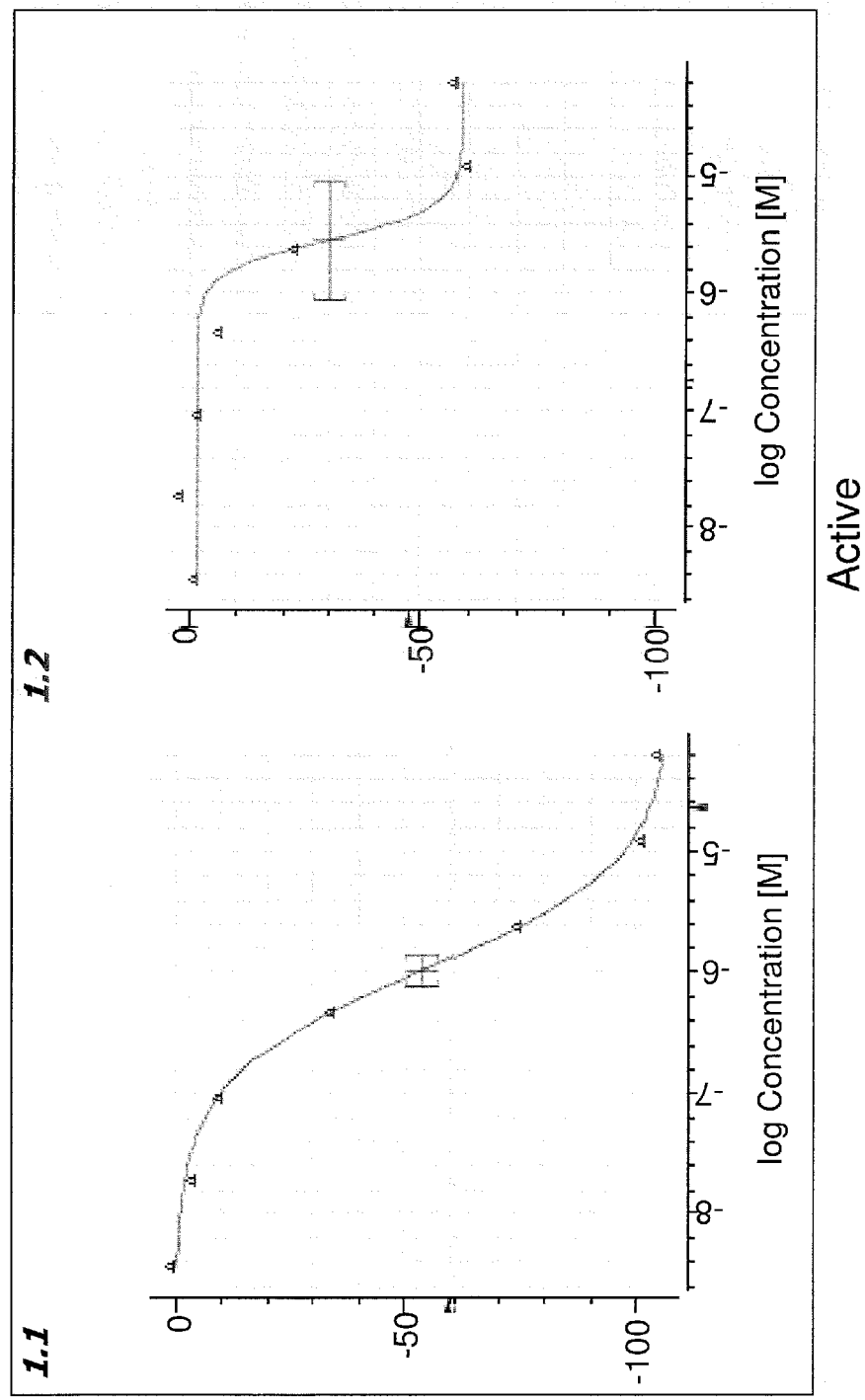
Figure 4:
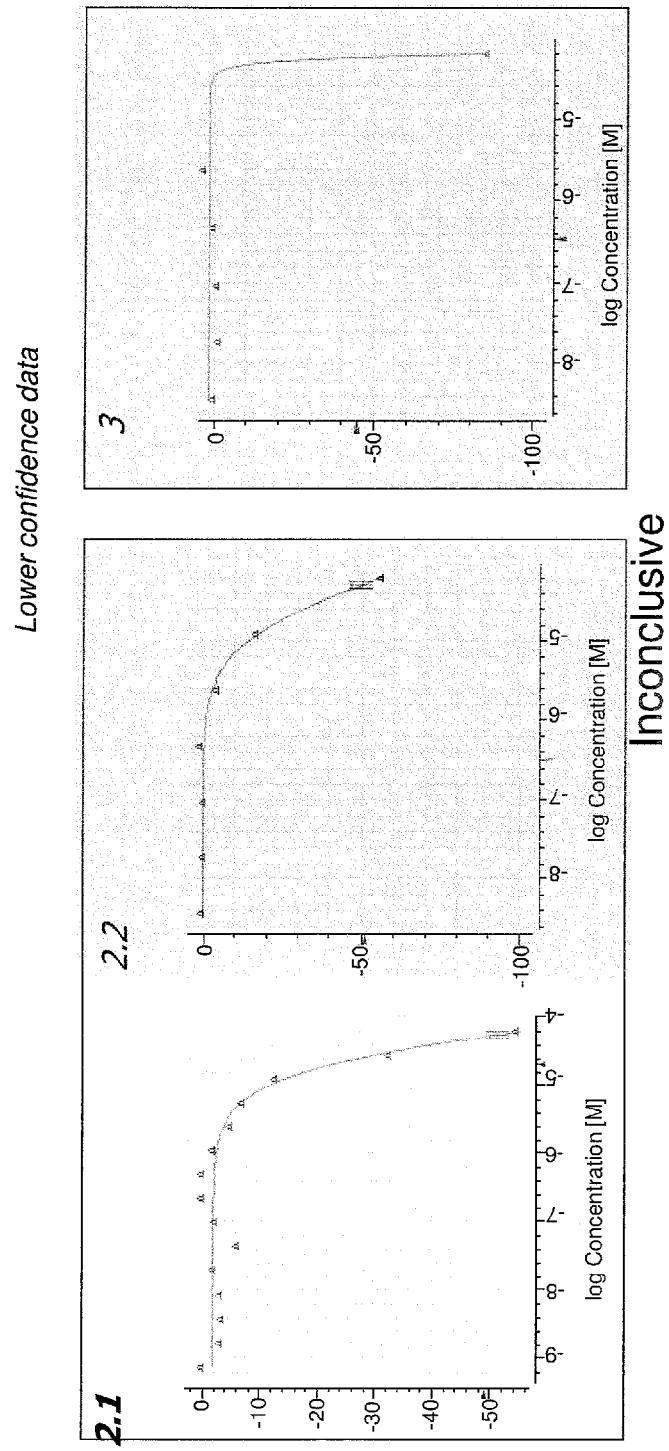
Figure 4:
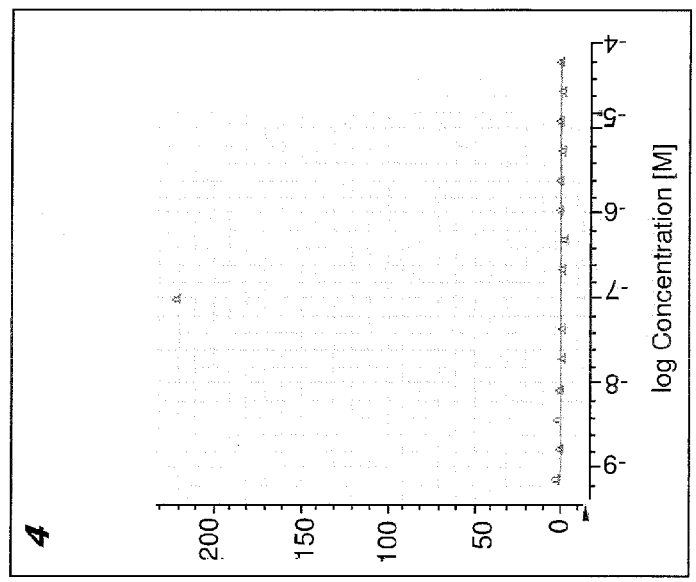

FIG. 4 is a series of curves that represent data from a Pin1 competition fluorescence polarization assay and that have been grouped into categories based on curve characteristics. Each curve plots log concentration (M) of the compound (X axis) against the emission of polarized fluorescence (Y axis), shown as percentage change in comparison to the emission of polarized fluorescence by an uninhibited control. In three dimensional plots, the third dimension is the sample number. Class 1 includes complete curves, having 2 asymptotes and $r^2 \geq 0.9$, with an efficacy of either >80% (class 1.1) or ≤80% (class 1.2). Class 1 curves may also be classified as noisy curves when efficacy is >80% and $r^2<0.9$ (class 1.3) or when efficacy is ≤80% and $r^2<0.9$ (class 1.4). Class 2 includes incomplete curves having 1 asymptote and an $r^2$ value of either >0.9 (subclass a) or <0.9 (subclass b), with an efficacy of either >80% (class 2.1) or ≤80% (class 2.2). Class 2 curves may also be classified as noisy curves when efficacy is >80% and $r^2<0.9$ (class 2.3) or when efficacy is ≤80% and $r^2<0.9$ (class 2.4). Class 3 includes single point activity curves having 1 asymptote and an efficacy >3 SD from the mean activity of the sample field at the highest tested concentration. Class 4 includes inactive curves, for which there are no asymptotes and for which efficacy and $r^2$ values are not applicable. A fifth class captures any curves not otherwise classified.

Figure 5:
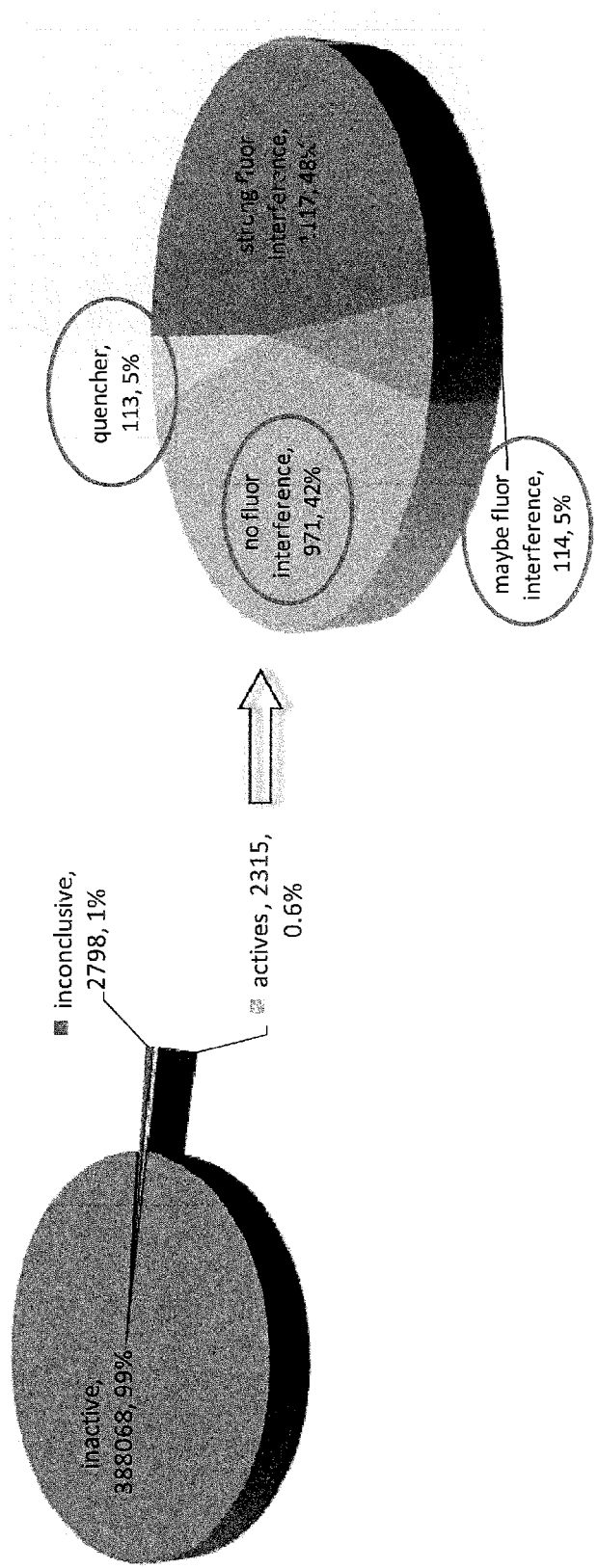

FIG. 5 summarizes the occurrence of curve types identified in a Pin1 competition fluorescence polarization assay. Active inhibitors are those yielding curves that fall into classes 1 and 2 with efficacy >50%. Class 4 curves are classified as inactive. All other curves are classified as inconclusive. Of 2315 active inhibitors, those demonstrating strong interference of fluorescence were not selected for further assessment.

DETAILED DESCRIPTION OF THE INVENTION

We have discovered compounds (i.e., the compounds of Table 1) useful for inhibiting Pin1. Inhibitors of Pin1 are useful for treating immune disorders and proliferative disorders (e.g., disorders characterized by elevated Pin1 marker levels). In other preferred embodiments, the compounds of Table 1 are useful for administration to subjects having aging-related disorders, asthma, and microbial infections. The usefulness of Pin1 inhibitors in treating the above diseases is further identified or elaborated in PCT Application Nos. PCT/US2012/029077, PCT/US2012/35473, PCT/US2012/39850, PCT/US2010/054077, U.S. Application Publication No. 2008/0214470 A1, U.S. Pat. Nos. 6,495,376 B1, 6,462,173 B1, 8,129,131 B2, 8,258,099 B2, and U.S. Provisional Application No. 61/490,338, each of which is hereby specifically incorporated by reference in its entirety.

The compounds of Table 1 were identified and validated using the methods described in the examples. In brief, the compounds were identified in a high-throughput screen for displacing a known binder of Pin-1 from Pin-1 proteins. Based on this displacement, and the nature of the displaced molecule, we conclude that the compounds are likely to inhibit Pin-1 activity.

I. PIN1

Phosphorylation on serine/threonine-proline motifs restrains cis/trans prolyl isomerization, and also creates a binding site for the essential protein Pin1. Pin1 binds and regulates the activity of a defined subset of phosphoproteins, as well as participating in the timing of mitotic progression. Both structural and functional analyses have indicated that Pin1 contains a phosphoserine/threonine-binding module that binds phosphoproteins, and a catalytic activity that specifically isomerizes the phosphorylated phosphoserine/threonine-proline. Both of these Pin1 activities are essential for Pin1 to carry out its function in vivo.

Pin1 has previously been shown to act on IRF3 to affect IFN-β production upon TLR3 or RIG-I activation. However, recent results have shown that unlike IRF3- or TLR3-deficient mice, IRF7 or IRAK1-deficient mice completely fail to mount a type I IFN antiviral responses due to loss of type I IFN secretion from pDCs. Results have uncovered an essential role for Pin1 as a novel regulator of IRAK1 activation in TLR signaling and type I IFN-mediated innate and adaptive immunity and revealed that Pin1 inhibitors, which are under active development, may represent a novel therapeutic approach that would allow selective inhibition of the type I IFN response while leaving proinflammatory cytokine production unaffected.

Pin1 is highly conserved and contains a protein-interacting module, called WW domain, and a catalytically active peptidyl-prolyl isomerase (PPIase). Pin1 is structurally and functionally distinct from members of two other well-characterized families of PPIases, the cyclophilins and the FKBPs. PPIases are ubiquitous enzymes that catalyze the typically slow prolyl isomerization of proteins, allowing relaxation of local energetically unfavorable conformational states. Phosphorylation on Ser/Thr residues immediately preceding Pro not only alters the prolyl isomerization rate, but also creates a binding site for the WW domain of Pin1. The WW domain acts a novel phosphoserine-binding module targeting Pin1 to a highly conserved subset of phosphoproteins. Furthermore, Pin1 displays a unique phosphorylation-dependent PPIase that specifically isomerizes phosphorylated Ser/Thr-Pro bonds and regulates the function of phosphoproteins.

II. METHODS OF IDENTIFYING PIN1 INHIBITORS

Numerous methods of identifying a Pin1 inhibitor are known in the art. In one method of identifying a Pin1 inhibitor, candidate or test compounds are substrates of a Pin1 protein or polypeptide or biologically active portion thereof that can bind to a Pin1 protein or polypeptide or biologically active portion thereof. In another method of identifying a Pin1 inhibitor, Test compounds that may be screened to identify a Pin1 inhibitor can be obtained from numerous available resources or using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other four approaches are applicable to peptide, non-peptide oligomer or small molecule libraries of compounds (Lam (1997) Anticancer Drug Des. 12:145). Examples of methods for the synthesis of molecular libraries can be found in the art, for example in: DeWitt et al. (1993) Proc. Natl. Acad. Sci. U.S.A. 90:6909; Erb et al. (1994) Proc. Natl. Acad. Sci. USA 91:11422; Zuckermann et al. (1994). J. Med. Chem. 37:2678; Cho et al. (1993) Science 261:1303; Carrell et al. (1994) Angew. Chem. Int. Ed. Engl. 33:2059; Carell et al. (1994) Angew. Chem. Int. Ed. Engl. 33:2061; and in Gallop et al. (1994) J. Med. Chem. 37:1233.

Libraries of compounds may be presented in solution (e.g., Houghten (1992) Biotechniques 13:412-421), on beads (Lam (1991) Nature 354:82-84), chips (Fodor (1993) Nature 364:555-556), bacteria (Ladner U.S. Pat. No. 5,223, 409), spores (Ladner U.S. Pat. No. '409), plasmids (Cull et al. (1992) Proc Natl Acad Sci USA 89:1865-1869) or on phage (Scott and Smith (1990) Science 249:386-390; Devlin (1990) Science 249:404-406; Cwirla et al. (1990) Proc. Natl. Acad. Sci. 87:6378-6382; Felici (1991) J. Mol. Biol. 222: 301-310; Ladner supra.).

In another method of identifying a Pin1 inhibitor, the assay is a cell-based assay in which a cell expressing a Pin1 target molecule (e.g., a Pin1 substrate; a phosphoprotein) is contacted with a test compound and the ability of the test compound to inhibit the activity of the Pin1 target molecule is determined. Determining the ability of the test compound to modulate the activity of a Pin1 target molecule can be accomplished, for example, by determining the ability of the Pin1 protein to bind to or interact with the Pin1 target molecule, or by determining the ability of the Pin1 protein to isomerize the Pin1 target molecule.

Determining the ability of the Pin1 protein to bind to or interact with a Pin1 target molecule can be accomplished by determining direct binding. Determining the ability of the Pin1 protein to bind to or interact with a Pin1 target molecule can be accomplished, for example, by coupling the Pin1 protein with a radioisotope or enzymatic label such that binding of the Pin1 protein to a Pin1 target molecule can be determined by detecting the labeled Pin1 protein in a complex. For example, Pin1 molecules, e.g., Pin1 proteins, can be labeled with, $I^{125}$, $S^{35}$, $C^{14}$, or $H^3$, either directly or indirectly, and the radioisotope detected by direct counting of radioemission or by scintillation counting. Alternatively, Pin1 molecules can be enzymatically labeled with, for example, horseradish peroxidase, alkaline phosphatase, or luciferase, and the enzymatic label detected by determination of conversion of an appropriate substrate to product.

The ability of a compound to modulate the interaction between Pin1 and its target molecule may also be determined without the labeling any of the interactants. For example, a microphysiometer can be used to detect the interaction of Pin1 with its target molecule without the labeling of either Pin1 or the target molecule (McConnell (1992) Science 257:1906-1912). A "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between compound and receptor.

Determining the ability of the Pin1 protein to bind to or interact with a Pin1 target molecule can be accomplished by determining the activity of the target molecule. For example, the activity of the target molecule can be determined by detecting induction of a downstream event (e.g., expression of cyclin D1, mitosis etc.), detecting catalytic/enzymatic activity of the target on an appropriate substrate, detecting the induction of a reporter gene (comprising a target-responsive regulatory element (e.g., AP-1) operatively linked to a nucleic acid optionally encoding a detectable marker, e.g., chloramphenicol acetyl transferase), or detecting a target-regulated cellular response.

Another method identifying a Pin1 inhibitor utilizes a cell-free assay in which a Pin1 protein or biologically active portion thereof is contacted with a test compound and the ability of the test compound to bind to the Pin1 protein or biologically active portion thereof is determined. Binding of the test compound to the Pin1 protein can be determined either directly or indirectly. For instance, the assay may include contacting the Pin1 protein or biologically active portion thereof with a known compound which binds Pin1 to form an assay mixture, contacting the assay mixture with a test compound, and determining the ability of the test compound to interact with a Pin1 protein, wherein determining the ability of the test compound to interact with a Pin1 protein comprises determining the ability of the test compound to preferentially bind to Pin1 or a biologically active portion thereof as compared to the known compound.

In another method of identifying a Pin1 inhibitor, the assay is a cell-free assay in which a Pin1 protein or biologically active portion thereof is contacted with a test compound and the ability of the test compound to inhibit the activity of the Pin1 protein or biologically active portion thereof is determined. Determining the ability of the test compound to modulate the activity of a Pin1 protein can be accomplished, for example, by determining the ability of the Pin1 protein to bind to a Pin1 target molecule using a technology such as real-time Biomolecular Interaction Analysis (BIA). Sjolander, S. and Urbaniczky, C. (1991)

Anal. Chem. 63:2338-2345 and Szabo et al. (1995) Curr. Opin. Struct. Biol. 5:699-705. As used herein, "BIA" is a technology for studying biospecific interactions in real time, without labeling any of the interactants (e.g., BIAcore). Changes in the optical phenomenon of surface plasmon resonance (SPR) can be used as an indication of real-time reactions between biological molecules.

In another method of identifying a Pin1 inhibitor, determining the ability of the test compound to modulate the activity of a Pin1 protein can be accomplished by determining the ability of the Pin1 protein to further modulate the isomerization of the activity of a Pin1 target molecule (e.g., a Pin1 substrate, a phosphoprotein).

In another method of identifying a Pin1 inhibitor, the cell-free assay involves contacting a Pin1 protein or biologically active portion thereof with a known compound which binds the Pin1 protein to form an assay mixture, contacting the assay mixture with a test compound, and determining the ability of the test compound to interact with the Pin1 protein, wherein determining the ability of the test compound to interact with the Pin1 protein comprises determining the ability of the Pin1 protein to preferentially bind to or modulate the activity of a Pin1 target molecule.

Cell-free assays for identifying a Pin1 inhibitor are amenable to use of both soluble and/or membrane-bound forms of proteins (e.g., Pin1 proteins or biologically active portions thereof, or receptors to which Pin1 binds). In the case of cell-free assays in which a membrane-bound form of a protein is used (e.g., a cell surface Pin1 receptor) it may be desirable to utilize a solubilizing agent such that the membrane-bound form of the protein is maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether).sub.n, 3-[(3-cholamidopropyl)dimethylamminio]-1-propane sulfonate (CHAPS), 3-[(3-cholamidopropyl)dimethyl-amminio]-2-hydroxy-1-propane sulfonate (CHAPSO), or N-dodecyl=N,N-dimethyl-3-ammonio-1-propane sulfonate.

In some methods of identifying a Pin1 inhibitor, it may be desirable to immobilize either Pin1 or its target molecule to facilitate separation of complexed from uncomplexed forms of one or both of the proteins, as well as to accommodate automation of the assay. Binding of a test compound to a Pin1 protein, or interaction of a Pin1 protein with a target molecule in the presence and absence of a candidate compound, can be accomplished in any vessel suitable for containing the reactants. Examples of such vessels include microtitre plates, test tubes, and micro-centrifuge tubes.

A fusion protein can be provided which adds a domain that allows one or both of the proteins to be bound to a matrix. For example, glutathione-S-transferase/Pin1 fusion proteins or glutathione-S-transferase/target fusion proteins can be adsorbed onto glutathione sepharose beads (Sigma Chemical, St. Louis, Mo.) or glutathione derivatized microtitre plates, which are then combined with the test compound or the test compound and either the non-adsorbed target protein or Pin1 protein, and the mixture incubated under conditions conducive to complex formation (e.g., at physiological conditions for salt and pH). Following incubation, the beads or microtitre plate wells are washed to remove any unbound components, or that are matrix immobilized in the case of beads, and complex formation may be determined either directly or indirectly, for example, as described above. Alternatively, the complexes can be dissociated from the matrix, and the level of Pin1 binding or activity determined using standard techniques.

Other techniques for immobilizing proteins on matrices can also be used in an assay for identifying a Pin1 inhibitor. For example, either a Pin1 protein or a Pin1 target molecule can be immobilized utilizing conjugation of biotin and streptavidin. Biotinylated Pin1 protein or target molecules can be prepared from biotin-NHS(N-hydroxy-succinimide) using techniques well known in the art (e.g., biotinylation kit, Pierce Chemicals, Rockford, Ill.), and immobilized in the wells of streptavidin-coated 96 well plates (Pierce Chemical). Alternatively, antibodies reactive with Pin1 protein or target molecules but which do not interfere with binding of the Pin1 protein to its target molecule can be derivatized to the wells of the plate, and unbound target or Pin1 protein trapped in the wells by antibody conjugation. Methods for detecting such complexes, in addition to those described above for the GST-immobilized complexes, include immunodetection of complexes using antibodies reactive with the Pin1 protein or target molecule, as well as enzyme-linked assays which rely on detecting an enzymatic activity associated with the Pin1 protein or target molecule.

In other assays for identifying a Pin1 inhibitor, a cell is contacted with a candidate compound and the expression of Pin1 mRNA or protein in the cell is determined. The level of expression of Pin1 mRNA or protein in the presence of the candidate compound is compared to the level of expression of Pin1 mRNA or protein in the absence of the candidate compound. The candidate compound can then be identified as a modulator of Pin1 expression based on this comparison. For example, when expression of Pin1 mRNA or protein is less (statistically significantly less) in the presence of the candidate compound than in its absence, the candidate compound is identified as an inhibitor of Pin1 mRNA or protein expression.

In some assays for identifying a Pin1 inhibitor, Pin1 proteins can be used as "bait proteins" in a two-hybrid assay or three-hybrid assay (see, e.g., U.S. Pat. No. 5,283,317; Zervos et al. (1993) Cell 72:223-232; Madura et al. (1993) J. Biol. Chem. 268:12046-12054; Bartel et al. (1993) Biotechniques 14:920-924; Iwabuchi et al. (1993) Oncogene 8:1693-1696; and Brent WO94/10300), to identify other proteins, which bind to or interact with Pin1 ("Pin1-binding proteins" or "Pin1-bp").

A two-hybrid system may be used in an assay for identifying a Pin1 inhibitor. A two-hybrid system may be based on the modular nature of most transcription factors and utilizes two different DNA constructs. In one construct, the gene that codes for a Pin1 protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a Pin1-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the Pin1 protein.

III. MEASUREMENT OF PIN1 MARKER LEVELS

The present invention pertains to the treatment of disorders identified as coinciding with elevated Pin1 marker levels with Table 1 Compounds. In some aspects, the invention features the determination of Pin1 marker levels in a subject and subsequently administering Table 1 Compound in subjects where Pin1 marker levels are determined to be elevated. In other aspects, the invention can also feature the measurement of Pin1 marker levels subsequent to the administration of Table 1 Compounds in order to evaluate the progress of therapy in treating the immune disorder or proliferative disorder.

Accordingly, one aspect of the present invention relates to diagnostic assays for measuring levels of Pin1 marker, as well as Pin1 activity, in the context of a biological sample (e.g., blood, urine, biopsies, lymph, saliva, phlegm, and pus) to thereby determine whether an individual is a candidate for treatment with a Table 1 Compound. The invention features both treatment of subjects exhibiting symptoms of an immune disorder, or proliferative disorder, and individuals at risk for developing such a disorder.

Diagnostic Assays

An exemplary method for detecting the presence or absence of Pin1 protein or nucleic acid in a biological sample involves obtaining a biological sample from a test subject and contacting the biological sample with a compound or an agent capable of detecting Pin1 protein or a nucleic acid (e.g., mRNA, genomic DNA) that encodes Pin1 protein such that the presence of Pin1 protein or nucleic acid is detected in the biological sample. A preferred agent for detecting Pin1 mRNA or genomic DNA is a labeled nucleic acid probe capable of hybridizing to Pin1 mRNA or DNA. The nucleic acid probe can be, for example, a Pin1 nucleic acid or a corresponding nucleic acid such as an oligonucleotide of at least 15, 30, 50, 100, 250 or 500 nucleotides in length which is capable of specifically hybridizing under stringent conditions to Pin1 mRNA or genomic DNA. Other suitable probes for use in the diagnostic assays of the invention are described herein.

A preferred agent for detecting Pin1 marker is an antibody capable of binding to Pin1 protein, preferably an antibody with a detectable label. Antibodies can be polyclonal, or more preferably, monoclonal. An intact antibody, or a fragment thereof (e.g., Fab or F(ab'2) can be used. The term "labeled," with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin.

With respect to antibody-based detection techniques, one of skill in the art can raise anti-Pin1 antibodies against an appropriate immunogen, such as isolated and/or recombinant Pin1 or a portion or fragment thereof (including synthetic molecules, such as synthetic peptides) using no more than routine experimentation. Synthetic peptides can be designed and used to immunize animals, such as rabbits and mice, for antibody production. The nucleic acid and amino acid sequence of Pin1 is known (Hunter et al., WO 97/17986 (1997); Hunter et al., U.S. Pat. Nos. 5,952,467 and 5,972, 697, the teachings of all of which are hereby incorporated by reference in their entirety) and can be used to design nucleic acid constructs for producing proteins for immunization or in nucleic acid detection methods or for the synthesis of peptides for immunization.

Conditions for incubating an antibody with a test sample can vary depending upon the tissue or cellular type. Incubation conditions can depend on the format employed in the assay, the detection methods employed, and the type and nature of the antibody used in the assay. One skilled in the art will recognize that any one of the commonly available immunological assay formats (such as radioimmunoassays, enzyme-linked immunosorbent assays, diffusion based Ouchterlony, or rocket immunofluorescent assays) can readily be adapted to employ a Pin1 antibody. Examples of such assays can be found in Chard, "An Introduction to Radioimmunoas say and Related Techniques," Elsevier Science Publishers, Amsterdam, The Netherlands (1986); Bullock et al., "Techniques in Immunocytochemistry," Academic Press, Orlando, Fla. Vol. 1 (1982), Vol. 2 (1983), Vol. 3 (1985); Tijssen, "Practice and Theory of enzyme Immunoassays: Laboratory Techniques in Biochemistry and Molecular Biology," is Elsevier Science Publishers, Amsterdam, The Netherlands (1985).

The detection method of the invention can be used to detect Pin1 mRNA, protein, or genomic DNA in a biological sample in vitro as well as in vivo. For example, in vitro techniques for detection of Pin1 mRNA include northern blot hybridizations and in situ hybridizations. In vitro techniques for detection of Pin1 protein include enzyme linked immunosorbent assays (ELISAs), Western blots, immunoprecipitations, immunofluorescence, or quantitative sequencing reactions. In vitro techniques for detection of Pin1 genomic DNA include Southern hybridizations. The detection of genomic mutations in Pin1 (or other genes that effect Pin1 marker levels) can be used to identify inherited or somatic mutations. Furthermore, in vivo techniques for detection of Pin1 protein include introducing into a subject a labeled anti-Pin1 antibody. For example, the antibody can be labeled with a radioactive marker whose presence and location in a subject can be detected by standard imaging techniques.

In another embodiment, the biological sample contains protein molecules from the test subject. Alternatively, the biological sample can contain mRNA molecules from the test subject or genomic DNA molecules from the test subject. A preferred biological sample is a serum sample isolated by conventional means from a subject.

In another embodiment, the methods further involve obtaining a control biological sample from a control subject, contacting the control sample with a compound or agent capable of detecting Pin1 marker such that the presence of Pin1 marker is detected in the biological sample, and comparing the presence of Pin1 marker in the control sample with the presence of Pin1 marker in the test sample.

The immunological assay test samples of the present invention may include cells, protein or membrane extracts of cells, blood or biological fluids such as ascites fluid or cerebrospinal fluid. The test sample used in the above-described method is based on the assay format, nature of the detection method and the tissues, cells or extracts used as the sample to be assayed. Methods for preparing protein extracts or membrane extracts of cells are well known in the art and can be readily be adapted in order to obtain a sample which is compatible with the system utilized.

The invention also encompasses kits for detecting the presence of Pin1 in a biological sample. For example, the kit can comprise a labeled compound or agent capable of detecting Pin1 protein or mRNA in a biological sample; means for determining the amount of Pin1 in the sample; and means for comparing the amount of Pin1 in the sample with a known standard. The compound or agent can be packaged in a suitable container. The kit can further comprise instructions for using the kit to detect Pin1 protein or nucleic acid.

Pin1 marker levels can also be measured in an assay designed to evaluate a panel of target genes, e.g., a microarray or multiplex sequencing reaction. In the embodiments of the invention described herein, well known biochemical methods such as northern blot analysis, RNase protection assays, southern blot analysis, western blot analysis, in situ hybridization, immunocytochemical procedures of tissue sections or cellular spreads, and nucleic acid amplification reactions (e.g., polymerase chain reactions) may be used interchangeably. One of skill in the art would be capable of performing these well-established protocols for the methods of the invention. (See, for example, Ausubel, et al., "Current Protocols in Molecular Biology," John Wiley & Sons, NY, N.Y. (1999)).

Diagnostic assays can be carried out in, e.g., subjects diagnosed or at risk of an immune disorder. Such disorders include, without limitation, acne vulgaris; acute respiratory distress syndrome; Addison's disease; adrenocortical insufficiency; adrenogenital ayndrome; allergic conjunctivitis; allergic rhinitis; allergic intraocular inflammatory diseases; ANCA-associated small-vessel vasculitis; angioedema; ankylosing spondylitis; aphthous stomatitis; arthritis; asthma; atherosclerosis; atopic dermatitis; autoimmune disease; autoimmune hemolytic anemia; autoimmune hepatitis; Behcet's disease; Bell's palsy; berylliosis; bronchial asthma; bullous herpetiformis dermatitis; bullous pemphigoid; carditis; celiac disease; cerebral ischaemia; chronic obstructive pulmonary disease; cirrhosis; Cogan's syndrome; contact dermatitis; COPD; Crohn's disease; Cushing's syndrome; dermatomyositis; diabetes mellitus; discoid lupus erythematosus; eosinophilic fasciitis; epicondylitis; erythema nodosum; exfoliative dermatitis; fibromyalgia; focal glomerulosclerosis; giant cell arteritis; gout; gouty arthritis; graft-versus-host disease; hand eczema; Henoch-Schonlein purpura; herpes gestationis; hirsutism; hypersensitivity drug reactions; idiopathic cerato-scleritis; idiopathic pulmonary fibrosis; idiopathic thrombocytopenic purpura; inflammatory bowel or gastrointestinal disorders, inflammatory dermatoses; juvenile rheumatoid arthritis; laryngeal edema; lichen planus; Loeffler's syndrome; lupus nephritis; lupus vulgaris; lymphomatous tracheobronchitis; macular edema; multiple sclerosis; musculoskeletal and connective tissue disorder; myasthenia gravis; myositis; obstructive pulmonary disease; ocular inflammation; organ transplant rejection; osteoarthritis; pancreatitis; pemphigoid gestationis; pemphigus vulgaris; polyarteritis nodosa; polymyalgia rheumatica; primary adrenocortical insufficiency; primary biliary cirrhosis; pruritus scroti; pruritis/inflammation, psoriasis; psoriatic arthritis; Reiter's disease; relapsing polychondritis; rheumatic carditis; rheumatic fever; rheumatoid arthritis; rosacea caused by sarcoidosis; rosacea caused by scleroderma; rosacea caused by Sweet's syndrome; rosacea caused by systemic lupus erythematosus; rosacea caused by urticaria; rosacea caused by zoster-associated pain; sarcoidosis; scleroderma; segmental glomerulosclerosis; septic shock syndrome; serum sickness; shoulder tendinitis or bursitis; Sjogren's syndrome; Still's disease; stroke-induced brain cell death; Sweet's disease; systemic dermatomyositis; systemic lupus erythematosus; systemic sclerosis; Takayasu's arteritis; temporal arteritis; thyroiditis; toxic epidermal necrolysis; tuberculosis; type-1 diabetes; ulcerative colitis; uveitis; vasculitis; and Wegener's granulomatosis. The invention also features the treatment of immune disorders that increase susceptibility to microbial or viral infection, including HIV.

Diagnostic assays can also be carried out in, e.g., subjects diagnosed or at risk of a proliferative disorder. Such disorders include, without limitation, leukemias (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphoma (Hodgkin's disease, non-Hodgkin's disease), Waldenstrom's macroglobulinemia, heavy chain disease, and solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, schwannoma, meningioma, melanoma, neuroblastoma, and retinoblastoma).

Prognostic Assays

The diagnostic methods described herein can furthermore be utilized to identify subjects having or at risk of developing a disease or disorder associated with aberrant Pin1 expression or activity. For example, the assays described herein, such as the preceding diagnostic assays or the following assays, can be utilized to identify a subject having or at risk of developing a disorder associated with Pin1 marker (e.g., an immune disorder or proliferative disorder). Thus, the present invention provides a method for identifying a disease or disorder associated with aberrant Pin1 expression or activity in which a test sample is obtained from a subject and Pin1 protein or nucleic acid (e.g., mRNA, genomic DNA) is detected, wherein the presence of Pin1 protein or nucleic acid is diagnostic for a subject having or at risk of developing a Pin1-associated disorder and are, therefore, susceptible to treatment with a Table 1 Compound.

Furthermore, the present invention provides methods for determining whether a subject can be effectively treated with a Table 1 Compound for a disorder associated with aberrant Pin1 expression or activity in which a test sample is obtained and Pin1 protein or nucleic acid expression or activity is detected (e.g., wherein the abundance of Pin1 protein or nucleic acid expression or activity is diagnostic for a subject that can be administered the agent to treat a disorder Pin1-associated disorder).

In one embodiment, the present invention provides methods for determining Pin1 post-translational modifications. More importantly, phosphorylation of Pin1 on Ser71 in the catalytic active site may also prevent Table 1 Compounds from binding to Pin1 active site and induce Pin1 degradation and inhibit Pin1 function. Therefore, detecting reduced Ser71 phosphorylation using phospho-specific Pin1 antibodies that we have generated can be a method to select patients for treatment with Table 1 Compounds and to explain why some patients may not respond to treatment with Table 1 Compounds.

The methods of the invention can also be used to detect genetic alterations in a Pin1 gene, thereby determining if a subject with the altered gene is at risk for a disorder associated with the Pin1 gene and, consequently, a candidate for therapy with Table 1 Compounds. In preferred embodiments, the methods include detecting, in a sample of cells from the subject, the presence or absence of a genetic alteration characterized by at least one alteration affecting the integrity of a gene encoding a Pin1-protein, or the mis-expression of the Pin1 gene. For example, such genetic alterations can be detected by ascertaining the existence of at least one of 1) a deletion of one or more nucleotides from a Pin1 gene; 2) an addition of one or more nucleotides to a Pin1 gene; 3) a substitution of one or more nucleotides of a Pin1 gene; 4) a chromosomal rearrangement of a Pin1 gene; 5) an alteration in the level of a messenger RNA transcript of a Pin1 gene; 6) aberrant modification of a Pin1 gene, such as of the methylation pattern of the genomic DNA; 7) the presence of a non-wild type splicing pattern of a messenger RNA transcript of a Pin1 gene; 8) a non-wild type level of a Pin1-protein; 9) allelic loss of a Pin1 gene; and 10) inappropriate post-translational modification of a Pin1-protein. As described herein, there are a large number of assay techniques known in the art which can be used for detecting alterations in a Pin1 gene. A preferred biological sample is a tissue or serum sample isolated by conventional means from a subject.

In certain embodiments, detection of the alteration involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) Science 241:1077-1080; and Nakazawa et al. (1994) Proc. Natl. Acad. Sci. USA 91:360-364), the latter of which can be particularly useful for detecting point mutations in the Pin1-gene (see Abravaya et al. (1995) Nucleic Acids Res 0.23:675-682). This method can include the steps of collecting a sample from a patient, isolating nucleic acid (e.g., genomic DNA, mRNA or both) from the sample, contacting the nucleic acid sample with one or more primers which specifically hybridize to a Pin1 gene under conditions such that hybridization and amplification of the Pin1-gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli, J. C. et al., (1990) Proc. Natl. Acad. Sci. USA 87:1874-1878), transcriptional amplification system (Kwoh, D. Y. et al, (1989) Proc. Natl. Acad. Sci. USA 86:1173-1177), Q-Beta Replicase (Lizardi, P. M. et al. (1988) Bio-Technology 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in a Pin1 gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicate mutations in the sample DNA. Moreover, the use of sequence specific ribozymes (see, for example, U.S. Pat. No. 5,498,531; hereby incorporated by reference) can be used to score for the presence of specific mutations by development or loss of a ribozyme cleavage site.

In other embodiments, genetic mutations in Pin1 can be identified by hybridizing a sample and control nucleic acids, e.g., DNA or RNA, to high density arrays containing hundreds or thousands of oligonucleotides probes (Cronin, M. T. et al. (1996) Human Mutation 7: 244-255; Kozal, M. J. et al. (1996) Nature Medicine 2: 753-759). For example, genetic mutations in Pin1 can be identified in two dimensional arrays containing light-generated DNA probes as described in Cronin, M. T. et al. supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the Pin1 gene and detect mutations by comparing the sequence of the sample Pin1 with the corresponding wild-type (control) sequence. Examples of sequencing reactions include those based on techniques developed by Maxam and Gilbert ((1977) Proc. Natl. Acad. Sci. USA 74:560) or Sanger ((1977) Proc. Natl. Acad. Sci. USA 74:5463). It is also contemplated that any of a variety of automated sequencing procedures can be utilized when performing the diagnostic assays ((1995) Biotechniques 19:448), including sequencing by mass spectrometry (see, e.g., PCT International Publication No. WO 94/16101; Cohen et al. (1996) Adv. Chromatogr. 36:127-162; and Griffin et al. (1993) Appl. Biochem. Biotechnol. 38:147-159).

Other methods for detecting mutations in the Pin1 gene include methods in which protection from cleavage agents is used to detect mismatched bases in RNA/RNA or RNA/DNA heteroduplexes (Myers et al. (1985) Science 230: 1242). In general, the art technique of "mismatch cleavage" starts by providing heteroduplexes formed by hybridizing (labeled) RNA or DNA containing the wild-type Pin1 sequence with potentially mutant RNA or DNA obtained from a tissue sample. The double-stranded duplexes are treated with an agent which cleaves single-stranded regions of the duplex such as which will exist due to basepair mismatches between the control and sample strands. For instance, RNA/DNA duplexes can be treated with RNase and DNA/DNA hybrids treated with S1 nuclease to enzymatically digesting the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al. (1988) Proc. Nat Acad Sci USA 85:4397; Saleeba et al. (1992) Methods Enzymol. 217:286-295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in Pin1 cDNAs obtained from samples of cells. For example, the mutY enzyme of E. coli cleaves A at G/A mismatches and the thymidine DNA glycosylase from HeLa cells cleaves T at G/T mismatches (Hsu et al. (1994) Carcinogenesis 15:1657-1662). According to an exemplary embodiment, a probe based on a Pin1 sequence, e.g., a wild-type Pin1 sequence, is hybridized to a cDNA or other DNA product from a test cell(s). The duplex is treated with a DNA mismatch repair enzyme, and the cleavage products, if any, can be detected from electrophoresis protocols or the like. See, for example, U.S. Pat. No. 5,459,039; hereby incorporated by reference.

In other embodiments, alterations in electrophoretic mobility will be used to identify mutations in Pin1 genes. For example, single strand conformation polymorphism (SSCP) may be used to detect differences in electrophoretic mobility between mutant and wild type nucleic acids (Orita et al. (1989) Proc Natl. Acad. Sci. USA: 86:2766, see also Cotton (1993) Mutat Res 285:125-144; and Hayashi (1992) Genet Anal Tech Appl 9:73-79). Single-stranded DNA fragments of sample and control Pin1 nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) Trends Genet. 7:5).

In yet another embodiment the movement of mutant or wild-type fragments in polyacrylamide gels containing a gradient of denaturant is assayed using denaturing gradient gel electrophoresis (DGGE) (Myers et al. (1985) Nature 313:495). When DGGE is used as the method of analysis, DNA will be modified to insure that it does not completely denature, for example by adding a GC clamp of approximately 40 by of high-melting GC-rich DNA by PCR. In a further embodiment, a temperature gradient is used in place of a denaturing gradient to identify differences in the mobility of control and sample DNA (Rosenbaum and Reissner (1987) Biophys Chem 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) Nature 324:163); Saiki et al. (1989) Proc. Natl Acad. Sci USA 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) Nucleic Acids Res. 17:2437-2448) or at the extreme 3' end of one primer where, under appropriate conditions, mismatch can prevent, or reduce polymerase extension (Prossner et al. (1993) Tibtech 11:238). In addition it may be desirable to introduce a novel restriction site in the region of the mutation to create cleavage-based detection (Gasparini et al. (1992) Mol. Cell Probes 6:1). It is anticipated that in certain embodiments amplification may also be performed using Taq ligase for amplification (Barany (1991) Proc. Natl. Acad. Sci USA 88:189). In such cases, ligation will occur only if there is a perfect match at the 3' end of the 5' sequence making it possible to detect the presence of a known mutation at a specific site by looking for the presence or absence of amplification.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving a Pin1 gene.

Furthermore, any cell type or tissue in which Pin1 is expressed may be utilized in the prognostic assays described herein.

As with the diagnostic assay described above, prognostic assays of Pin1 activity can be included as part of a panel of target genes.

Additional methods of detecting Pin1 activity and diagnosing Pin1 related disorders are disclosed in U.S. Patent Application Publication Nos.: 2009/0258352, 2008/0214470, 2006/0074222, 2005/0239095, US2002/0025521, U.S. Pat. No. 6,495,376, and PCT Application Publication No. WO02/065091, each of which is hereby incorporated by reference in its entirety.

Monitoring the Effects of Treatment

In one embodiment, the present invention features a method for monitoring the effectiveness of treatment of a subject with a Table 1 Compound comprising the steps of (i) obtaining a pre-administration sample from a subject prior to administration of the compound; (ii) detecting the level of expression or activity of a Pin1 protein, Pin1 phosphorylation on Ser71, mRNA, genomic DNA, or other Pin1 marker in the pre-administration sample; (iii) obtaining one or more post-administration samples from the subject; (iv) detecting the level of expression or activity of the Pin1 protein, mRNA, or genomic DNA in the post-administration samples; (v) comparing the level of expression or activity of the Pin1 protein, mRNA, or genomic DNA in the pre-administration sample with the Pin1 protein, mRNA, genomic DNA, or other Pin1 Marker in the post administration sample or samples; and (vi) altering the administration of the Table 1 Compound to the subject accordingly. According to such an embodiment, Pin1 expression, phosphorylation or activity may be used as an indicator of the effectiveness of the Table 1 Compound, even in the absence of an observable response.

IV. FORMULATIONS

The inhibitors of the present invention can be formulated into compositions with an effective amount of the Pin1 inhibitor as an active ingredient. Such compositions can also comprise a pharmaceutically acceptable carrier, and are referred to herein as pharmaceutical compositions. The inhibitor compositions of the present invention can be administered intravenously, parenterally, orally, by inhalation or by suppository. Formulations of the present invention include those suitable for oral, nasal, topical, transdermal, buccal, sublingual, rectal, vaginal and/or parenteral administration. The formulations may conveniently be presented in unit dosage form and may be prepared by any methods well known in the art of pharmacy. The amount of active ingredient that can be combined with a carrier material to produce a single dosage form will generally be that amount of the compound that produces a therapeutic effect. Generally, out of one hundred percent, this amount will range from about 1 percent to about 99 percent of active ingredient, preferably from about 5 percent to about 70 percent, most preferably from about 10 percent to about 30 percent. The inhibitor composition may be administered in a single dose or in more than one dose over a period of time to achieve a level of inhibitor which is sufficient to confer the desired effect.

Suitable pharmaceutical carriers include, but are not limited to water, salt solutions, alcohols, polyethylene glycols, gelatin, carbohydrates such as lactose, amylose or starch, magnesium stearate, talc, silicic acid, viscous paraffin, fatty acid esters, hydroxymethylcellulose, polyvinyl pyrolidone, etc. The pharmaceutical preparations can be sterilized, mixed with auxiliary agents, preservatives, stabilizers, wetting agents, emulsifiers or lubricants such as sodium lauryl sulfate and magnesium stearate, salts for influencing osmotic pressure, buffers, coloring, and/or aromatic substances and the like which do not deleteriously react with the active compounds. They can also be combined where desired with other active agents, e.g., enzyme inhibitors, to reduce metabolic degradation. Release agents, coating agents, sweetening, flavoring and perfuming agents, preservatives and antioxidants can also be present in the compositions.

Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, .alpha.-tocopherol, and the like; and metal chelating agents, such as citric acid, ethylenediamine tetraacetic acid (EDTA), sorbitol, tartaric acid, phosphoric acid, and the like.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol and glycerol monostearate; absorbents, such as kaolin and bentonite clay; lubricants, such a talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluent commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the active compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissue.

The preparations of the present invention may be given orally, parenterally, topically, or rectally. They may be given by forms suitable for each administration route. For example, they may be administered in tablet or capsule form, injection, inhalation, eye lotion, ointment, suppository, infusion; topical lotion or ointment; or rectal suppository.

Parenteral administration includes modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion. For parenteral application, injectable, sterile solutions, oily or aqueous solutions, as well as suspensions, emulsions, or implants, including suppositories, are suitable. Ampoules are convenient unit dosages.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

It will be appreciated that the actual effective amounts of the inhibitor in a specific case will vary according to the specific compound being utilized, the particular composition formulated, the mode of administration and the age, weight and condition of the patient, for example. Dosages for a particular patient can be determined by one of ordinary skill in the art using conventional considerations, (e.g., by means of an appropriate, conventional pharmacological protocol).

The regimen of administration can affect what constitutes an effective amount. The Pin1 binding compound can be administered to the subject either prior to or after the onset of a Pin1 associated state. Further, several divided dosages, as well as staggered dosages, can be administered daily or sequentially, or the dose can be continuously infused, or can be a bolus injection. Further, the dosages of the Pin1 binding compound(s) can be proportionally increased or decreased as indicated by the exigencies of the therapeutic or prophylactic situation.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient. If desired, the effective daily dose of the active compound may be administered as two, three, four, five, six or more sub-doses administered separately at appropriate intervals throughout the day, optionally, in unit dosage forms.

V. METHODS OF TREATMENT

The present invention provides for both prophylactic and therapeutic methods of treating a subject at risk of (or susceptible to) or afflicted with a disorder associated with increased Pin1 expression or activity with a Table 1 Compound.

Prophylactic Methods

In one aspect, the invention provides a method for preventing an immune disorder or proliferative disorder in a subject by administering to the subject a Table 1 compound. Subjects at risk for a disease which is caused or contributed to by aberrant Pin1 expression or activity can be identified by, for example, any or a combination of diagnostic or prognostic assays as described herein. Administration of a Table 1 Compound can occur prior to the manifestation of symptoms characteristic of the Pin1 aberrancy, such that a disease or disorder is prevented and/or its progression delayed.

Combination Therapies

Anti-inflammatory agents are useful for treating an immune disorder or proliferative disorder in combination with the Table 1 Compounds of the invention. Anti-inflammatory agents that can be used in combination with a Table 1 Compound include, without limitation, corticosteroids, NSAIDs (e.g., naproxen sodium, diclofenac sodium, diclofenac potassium, aspirin, sulindac, diflunisal, piroxicam, indomethacin, ibuprofen, nabumetone, choline magnesium trisalicylate, sodium salicylate, salicylsalicylic acid (salsalate), fenoprofen, flurbiprofen, ketoprofen, meclofenamate sodium, meloxicam, oxaprozin, sulindac, and tolmetin), COX-2 inhibitors (e.g., rofecoxib, celecoxib, valdecoxib, and lumiracoxib), biologics (e.g., inflixamab, adelimumab, etanercept, CDP-870, rituximab, and atlizumab), small molecule immunomodulators (e.g., VX 702, SCIO 469, doramapimod, RO 30201195, SCIO 323, DPC 333, pranalcasan, mycophenolate, and merimepodib), non-steroidal immunophilin-dependent immunosuppressants (e.g., cyclosporine, tacrolimus, pimecrolimus, and ISAtx247), 5-amino salicylic acid (e.g., mesalamine, sulfasalazine, balsalazide disodium, and olsalazine sodium), DMARDs (e.g., methotrexate, leflunomide, minocycline, auranofin, gold sodium thiomalate, aurothioglucose, and azathioprine), hydroxychloroquine sulfate, and penicillamine.

In cases where there is a viral or microbial infection, the Table 1 Compounds of the invention can be administered with an antimicrobial agent, e.g., the penicillins (e.g., penicillin G, ampicillin, methicillin, oxacillin, and amoxicillin), the cephalosporins (e.g., cefadroxil, ceforanid, cefotaxime, and ceftriaxone), the tetracyclines (e.g., doxycycline, minocycline, and tetracycline), the aminoglycosides (e.g., amikacin, gentamycin, kanamycin, neomycin, streptomycin, and tobramycin), the macrolides (e.g., azithromycin, clarithromycin, and erythromycin), the fluoroquinolones (e.g., ciprofloxacin, lomefloxacin, and norfloxacin), and other antibiotics including chloramphenicol, clindamycin, cycloserine, isoniazid, rifampin, and vancomycin. Particularly useful formulations contain aminoglycosides, including for example amikacin, gentamicin, kanamycin, neomycin, netilmicin, paromomycin, streptomycin, and tobramycin, or an antiviral agent, e.g., 1-D-ribofuranosyl-1,2,4-triazole-3 carboxamide, 9→2-hydroxy-ethoxy methylguanine, adamantanamine, 5-iodo-2'-deoxyuridine, trifluorothymidine, interferon, adenine arabinoside, protease inhibitors, thymidine kinase inhibitors, sugar or glycoprotein synthesis inhibitors, structural protein synthesis inhibitors, attachment and adsorption inhibitors, and nucleoside analogues such as acyclovir, penciclovir, valacyclovir, and ganciclovir.

Anti-cancer agents that can be used in combination with a Table 1 Compound include, without limitation,MK-2206, ON 013105, RTA 402, BI 2536, Sorafenib, ISIS-STAT3Rx, a microtubule inhibitor, a topoisomerase inhibitor, a platin, an alkylating agent, an anti-metabolite, paclitaxel, gemcitabine, doxorubicin, vinblastine, etoposide, 5-fluorouracil, carboplatin, altretamine, aminoglutethimide, amsacrine, anastrozole, azacitidine, bleomycin, busulfan, carmustine, chlorambucil, 2-chlorodeoxyadenosine, cisplatin, colchicine, cyclophosphamide, cytarabine, cytoxan, dacarbazine, dactinomycin, daunorubicin, docetaxel, estramustine phosphate, floxuridine, fludarabine, gentuzumab, hexamethylmelamine, hydroxyurea, ifosfamide, imatinib, interferon, irinotecan, lomustine, mechlorethamine, melphalen, 6-mercaptopurine, methotrexate, mitomycin, mitotane, mitoxantrone, pentostatin, procarbazine, rituximab, streptozocin, tamoxifen, temozolomide, teniposide, 6-thioguanine, topotecan, trastuzumab, vincristine, vindesine, and/or vinorelbine.

Such compounds can act synergistically with a Table 1 Compound. Additionally, co-administration with a Table 1 Compound may result in the efficacy of the anti-inflammatory compound at lower (and thus safer) doses (e.g., at least 5% less (e.g., at least 10%, 20%, 50%, 80%, 90%, or even 95%) less than when the anti-inflammatory compound is administered alone.

Therapy according to the invention may be performed alone or in conjunction with another therapy and may be provided at home, the doctor's office, a clinic, a hospital's outpatient department, or a hospital. Treatment optionally begins at a hospital so that the doctor can observe the therapy's effects closely and make any adjustments that are needed, or it may begin on an outpatient basis. The duration of the therapy depends on the type of disease or disorder being treated, the age and condition of the patient, the stage and type of the patient's disease, and how the patient responds to the treatment. Additionally, a person having a greater risk of developing an immune disease or proliferative disorder, may receive treatment to inhibit or delay the onset of symptoms.

Routes of administration for the various embodiments include, but are not limited to, topical, transdermal, nasal, and systemic administration (such as, intravenous, intramuscular, subcutaneous, inhalation, rectal, buccal, vaginal, intraperitoneal, intraarticular, ophthalmic, otic, or oral administration). As used herein, "systemic administration" refers to all nondermal routes of administration, and specifically excludes topical and transdermal routes of administration.

In combination therapy (e.g., a Table 1 Compound with a second therapeutic agent), the dosage and frequency of administration of each component of the combination can be controlled independently. For example, one compound may be administered three times per day, while the second compound may be administered once per day. Combination therapy may be given in on-and-off cycles that include rest periods so that the patient's body has a chance to recover from any as yet unforeseen side effects. The compounds may also be formulated together such that one administration delivers both compounds.

Each compound of the combination may be formulated in a variety of ways that are known in the art. For example, the first and second agents may be formulated together or separately. Desirably, the first and second agents are formulated together for the simultaneous or near simultaneous administration of the agents. Such co-formulated compositions can include the two drugs together in the same pill, ointment, cream, foam, capsule, liquid, etc. It is to be understood that, when referring to the formulation of combinations of the invention, the formulation technology employed is also useful for the formulation of the individual agents of the combination, as well as other combinations of the invention. By using different formulation strategies for different agents, the pharmacokinetic profiles for each agent can be suitably matched.

The individually or separately formulated agents can be packaged together as a kit. Non-limiting examples include kits that contain, e.g., two pills, a pill and a powder, a suppository and a liquid in a vial, two topical creams, ointments, foams etc. The kit can include optional components that aid in the administration of the unit dose to patients, such as vials for reconstituting powder forms, syringes for injection, customized IV delivery systems, inhalers, etc. Additionally, the unit dose kit can contain instructions for preparation and administration of the compositions. The kit may be manufactured as a single use unit dose for one patient, multiple uses for a particular patient (at a constant dose or in which the individual compounds may vary in potency as therapy progresses); or the kit may contain multiple doses suitable for administration to multiple patients ("bulk packaging"). The kit components may be assembled in cartons, blister packs, bottles, tubes, and the like.

VI. PHARMACOGENOMICS

The Pin1 inhibitors described herein can be administered to individuals to treat (prophylactically or therapeutically) disorders (e.g, proliferative disorders such as cancer) associated with aberrant Pin1 activity. In conjunction with such treatment, pharmacogenomics (i.e., the study of the relationship between an individual's genotype and that individual's response to a foreign compound or drug) may be considered. Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer a Pin1 inhibitor as well as tailoring the dosage and/or therapeutic regimen of treatment with a Pin1 molecule or Pin1 modulator.

Pharmacogenomics deals with clinically significant hereditary variations in the response to drugs due to altered drug disposition and abnormal action in affected persons (see, for example, Eichelbaum, M. et al. (1996) Clin. Exp. Pharmacol. Physiol. 23(10-11): 983-985 and Linder, M. W. et al. (1997) Clin. Chem. 43(2):254-266). In general, two types of pharmacogenetic conditions can be differentiated: Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare genetic defects or as naturally-occurring polymorphisms. For example, glucose-6-phosphate dehydrogenase deficiency (G6PD) is a common inherited enzymopathy in which the main clinical complication is haemolysis after ingestion of oxidant drugs (anti-malarials, sulfonamides, analgesics, nitrofurans) and consumption of fava beans.

One pharmacogenomics approach to identifying genes that predict drug response, known as "genome-wide association", relies primarily on a high-resolution map of the human genome consisting of already known gene-related markers (e.g., a "bi-allelic" gene marker map which consists of 60,000-100,000 polymorphic or variable sites on the human genome). Such a high-resolution genetic map can be compared to a map of the genome of each of a statistically significant number of patients taking part in a Phase II/III drug trial to identify markers associated with a particular observed drug response or side effect. Alternatively, such a high resolution map can be generated from a combination of some ten-million known single nucleotide polymorphisms (SNPs) in the human genome. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that may be common among such genetically similar individuals.

Alternatively, a method termed the "candidate gene approach," can be utilized to identify genes that predict a drug response. According to this method, if a gene that encodes a drug target is known (e.g., a Pin1 inhibitor of the present invention), all common variants of that gene can be fairly easily identified in the population and it can be determined if having one version of the gene versus another is associated with a particular drug response.

As an illustration, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C19 quite frequently experience exaggerated drug response and side effects when they receive standard doses. If a metabolite is the active therapeutic moiety, PM show no therapeutic response, as demonstrated for the analgesic effect of codeine mediated by its CYP2D6-formed metabolite morphine. The other extreme are the so called ultra-rapid metabolizers who do not respond to standard doses. Recently, the molecular basis of ultra-rapid metabolism has been identified to be due to CYP2D6 gene amplification.

Alternatively, a method termed the "gene expression profiling," can be utilized to identify genes that predict drug response. For example, the gene expression of an animal dosed with a drug (e.g., a Pin1 inhibitor of the present invention) can give an indication of whether gene pathways related to toxicity have been turned on.

Information generated from one or more of the above pharmacogenomics approaches, or other approaches known in the art, can be used to determine appropriate dosage and treatment regimens for prophylactic or therapeutic treatment an individual. Pharmacogenomic findings, when applied to dosing or drug selection, can avoid adverse reactions or therapeutic failure and thus enhance therapeutic or prophylactic efficiency when treating a subject with a Pin1 inhibitor, such as a modulator identified by one of the exemplary screening assays described herein.

VII. FURTHER APPLICATIONS OF PIN1 INHIBITORS

The inhibitors of the present invention can be used to interfere with eukaryotic cell growth. The inhibitors can be used in vitro to study cell cycle regulation, mitotic events, protein degradation, apoptosis, neurodegenerative diseases, or certain aspects of cell division such as embryonic development, or signaling pathways thereof. The inhibitors can be used in defining pathways which lead to carcinogenesis or to evaluate, interfere with, or treat events such as cell spreading in metastatic cancers. The inhibitors can be used to inhibit cell growth, and to kill targeted cells. For example, the inhibitors of the present invention can be used to interfere with the growth of fungus or yeast, including *Aspergillus*, and parasitic infections (e.g., malaria) in mammals such as domesticated animals and humans.

VIII. EXPERIMENTAL RESULTS

Example 1

Pin1 Inhibitor Assay

Figure 1:
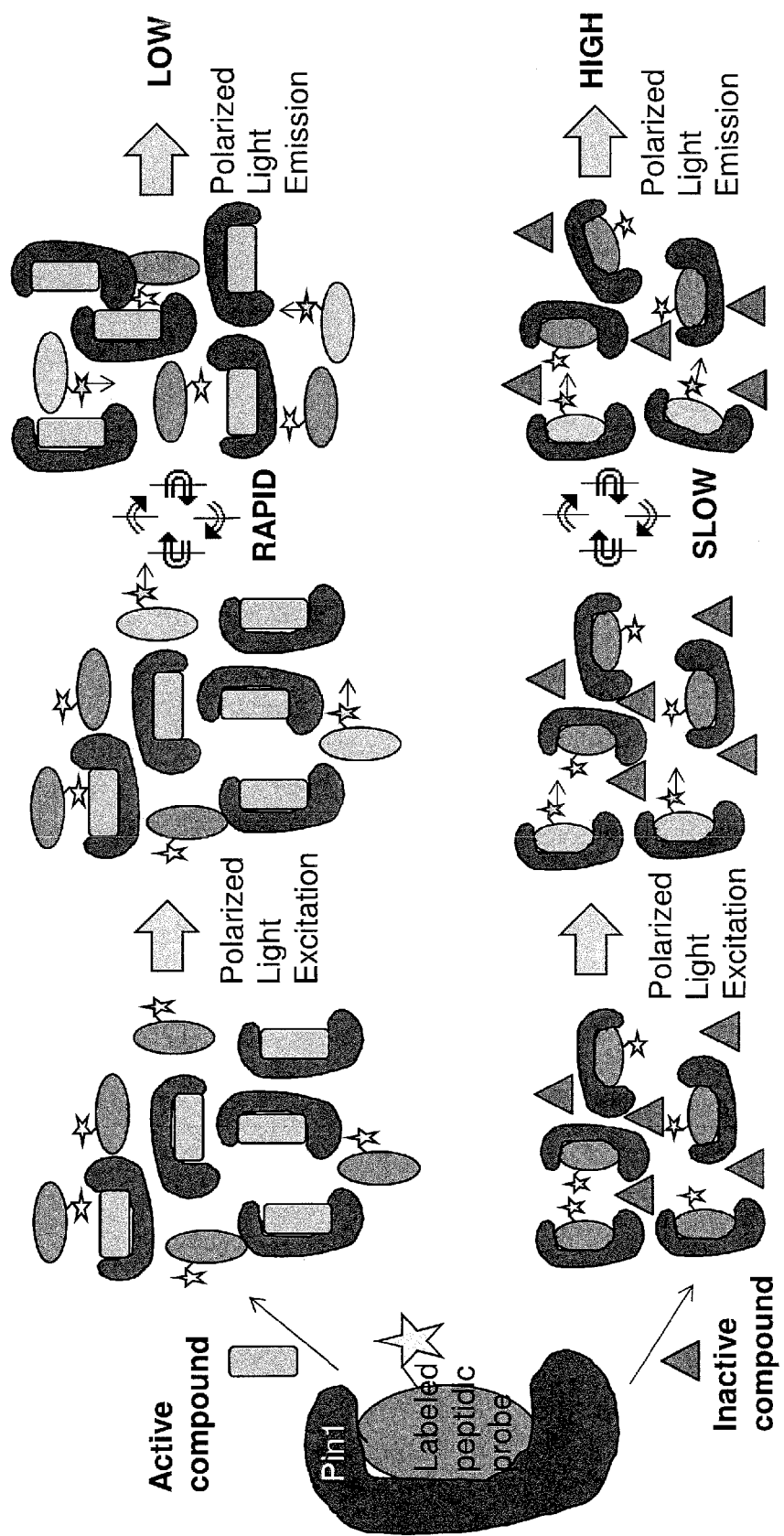
FIG. 1 is a schematic diagram of a Pin1 competition fluorescence polarization assay. Pin1 protein is incubated in the presence of a fluorophore-labeled Pin1 probe with which Pin1 may interact and, optionally, a compound of interest. The compound may inhibit the interaction of Pin1 with the fluorophore-labeled probe. When the fluorophore on the probe is excited by polarized light, the resulting emission of polarized light will depend upon the extent to which the probe interacts with Pin1. A compound that does not inhibit the interaction of the probe with Pin1 generally will not decrease the detected emission of polarized light relative to a control value such as the emission of polarized fluorescence by an uninhibited control. In contrast, when the compound does inhibit interaction of probe and Pin1, the detected emission of polarized light will be decreased relative to a control value such as the emission of polarized fluorescence by an uninhibited control.

An assay was developed for the identification of inhibitors of Pin1. The goal of this assay was to identify small-molecule inhibitors of Pin1 using a fluorescence polarization competition assay (FIG. 1). In this assay, fluorescence polarization is used to determine whether a given candidate small molecule inhibitory compound displaces a HiFluor-488-labeled peptide that normally binds to the active site of Pin1. Candidate compounds were screened in a concentration-titration series (e.g., 57 µM to 0.7 nM).

Pin1 (0.6 µM) was dispensed into black, solid 1536-well plates (32 rows by 48 columns) at 2 µL/well in Pin1 buffer (10 mM HEPES (pH 7.5), 10 mM NaCl, 0.01% Tween20, 1 mM DTT, and 1% glycerol). Next, 23 nL of compound or DMSO was delivered to each well using a pin tool (tip wash sequence: DMSO, IPA, MeOH, 3 s vacuum dry). Two µL of Pin1-1b-HiFluor488 peptide in buffer (10 mM HEPES (pH 7.5), 10 mM NaCl, 0.01% Tween20, 1 mM DTT, and 1% glycerol, 0.02 µM Pin1-1b-HiFluor488) or DMSO was then dispensed to each well using a pin tool (tip wash sequence: DMSO, IPA, MeOH, 3 s vacuum dry), and plates were incubated at room temperature for 10 min (Table 2). Each plate included controls with no candidate inhibitory compound (32 wells), with unlabeled Pin1-lc titration (3.5 mM to 0.020 mM in a 1:2 dilution series including 2 replicates per concentration; 32 wells), and without Pin1 (64 wells).

TABLE 2

Pin1 Assay Protocol

| Step | Parameter | Value | Description |
|------|-----------|-------|-------------|
| 1 | Reagent | 2 µL | Pin1 buffer (0.6 µM Pin1; 0 µM controls) |
| 2 | Library compounds | 23 nL | Dilution series (10 mM, 7-pt) |
| 3 | Control compounds | 23 nL | DMSO, Pin1-1c dilution series (3.5 mM, 16-pt) |
| 4 | Reagent | 2 µL | Probe 488 buffer |
| 5 | Time | 10 min | Room temperature incubation |
| 6 | Detection | Polarization | ViewLux ® |

The fluorescence polarization signal of each well was measured on a ViewLux® plate reader using a 480/20 nm excitation filter and 540/25 nm S and P emission filters with a 20 second exposure with 2× binning (Table 2). Percent inhibitory activity was determined from corrected fluorescence polarization values. Unlabeled Pin1-1c peptide was used as a control (3.5 mM two-fold serial; 20 µM final concentration) with a 1×(0.3 µM) and 0×(no-enzyme) Pin1 enzyme control to normalize the percent activity of identified inhibitors; 0× enzyme values corresponded to full inhibition, while 1×Pin1 enzyme values were used to normalize no inhibition.

Concentration-response curves were fitted to the signals arising from the resulting fluorescence polarization. The concentration-effect curves were then classified based on curve quality ($r^2$), response magnitude, and degree of measured activity. Compounds were subsequently categorized based on their curve class. Active inhibitors showed concentration-dependent decreases in fluorescence polarization, concordant with their displacement of Pin1-1b-HiFluor488 from the Pin1 active site (see, e.g., FIGS. 3A-3D). Inactive compounds showed no effect on the fluorescence polarization signal.

Example 2

Quantitative High Throughput Analysis of Candidate Pin1 Inhibitors

Figure 2:
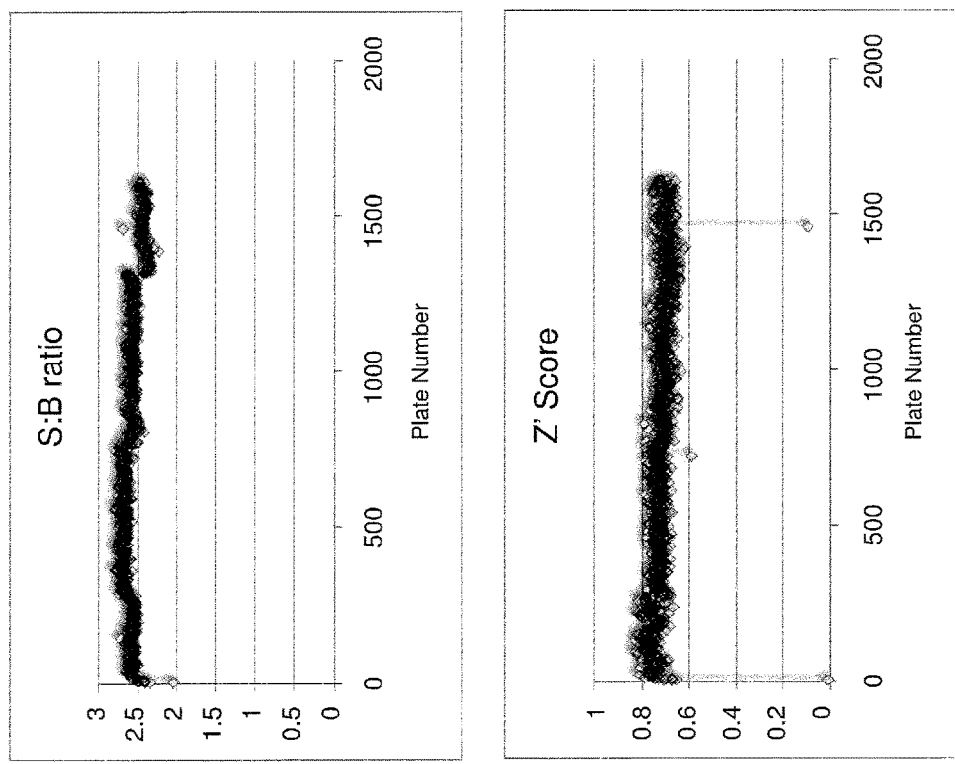
FIG. 2 is a set of three graphs relating to the performance of a Pin1 competition fluorescence polarization assay of 1607 plates, each containing 1536 wells, covering a total of 393,181 compounds. Graphs show S:B ratio, Z' Score (Z' factor=1−3*(SD of positive control+SD of basal)/(median of positive control−median of basal)), and CV % (CV (coefficient of variation)=SD of compound area/median of compound area).
Figure 2:
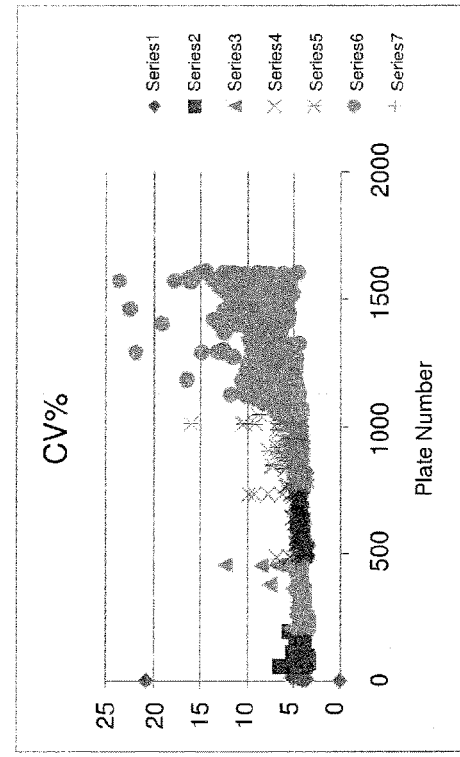
Figure 3A:
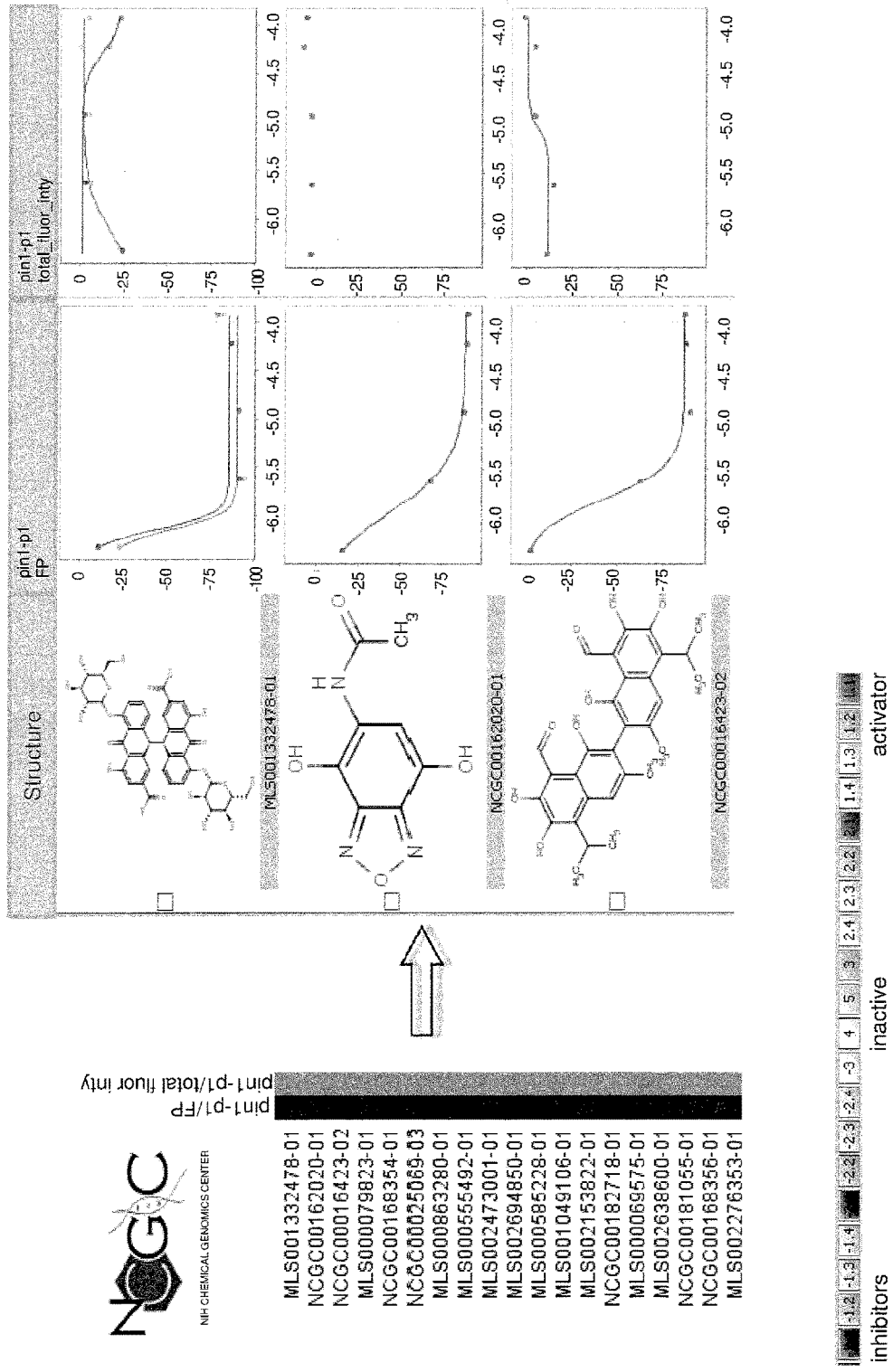
Figure 3A:
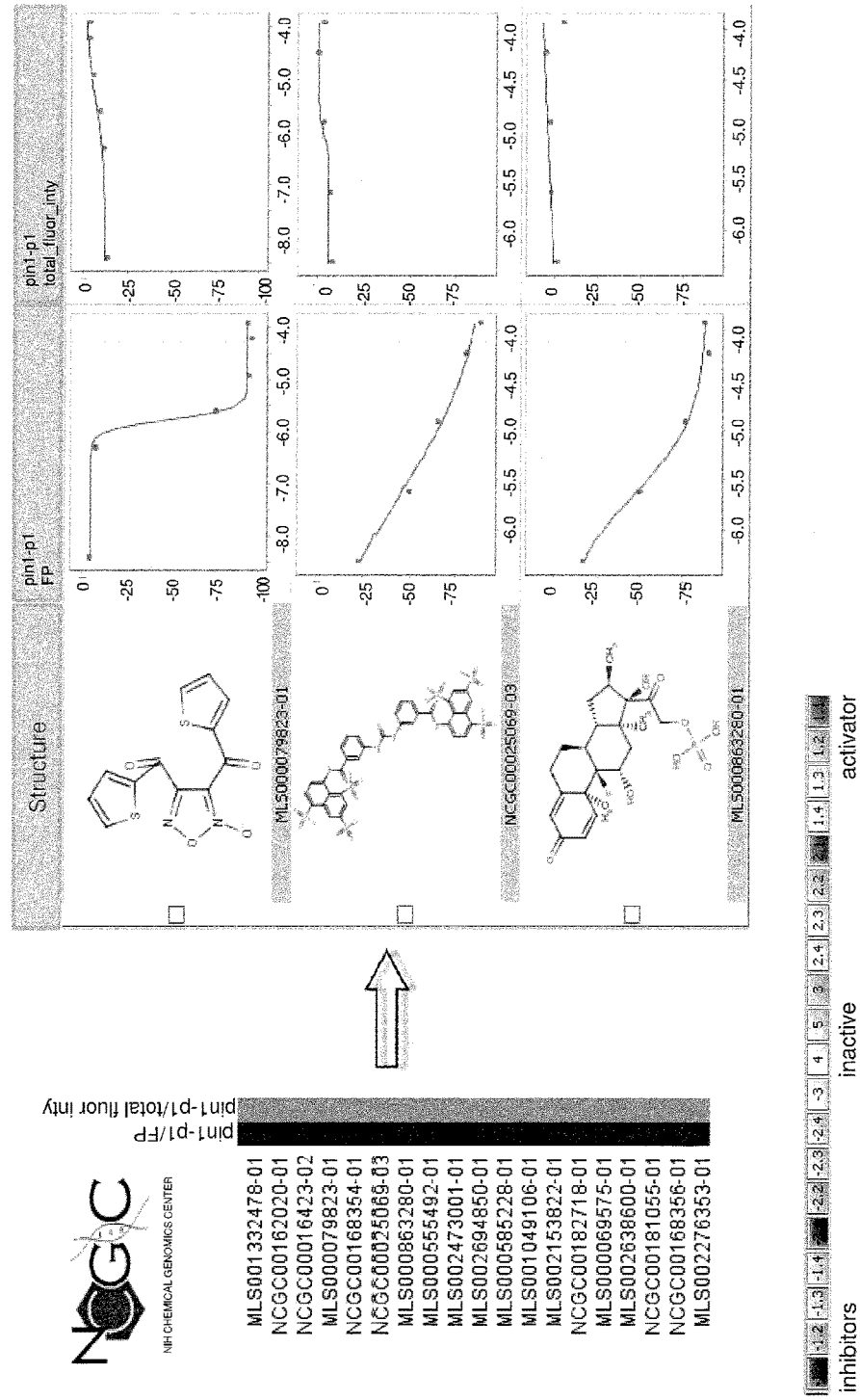
Figure 3B:
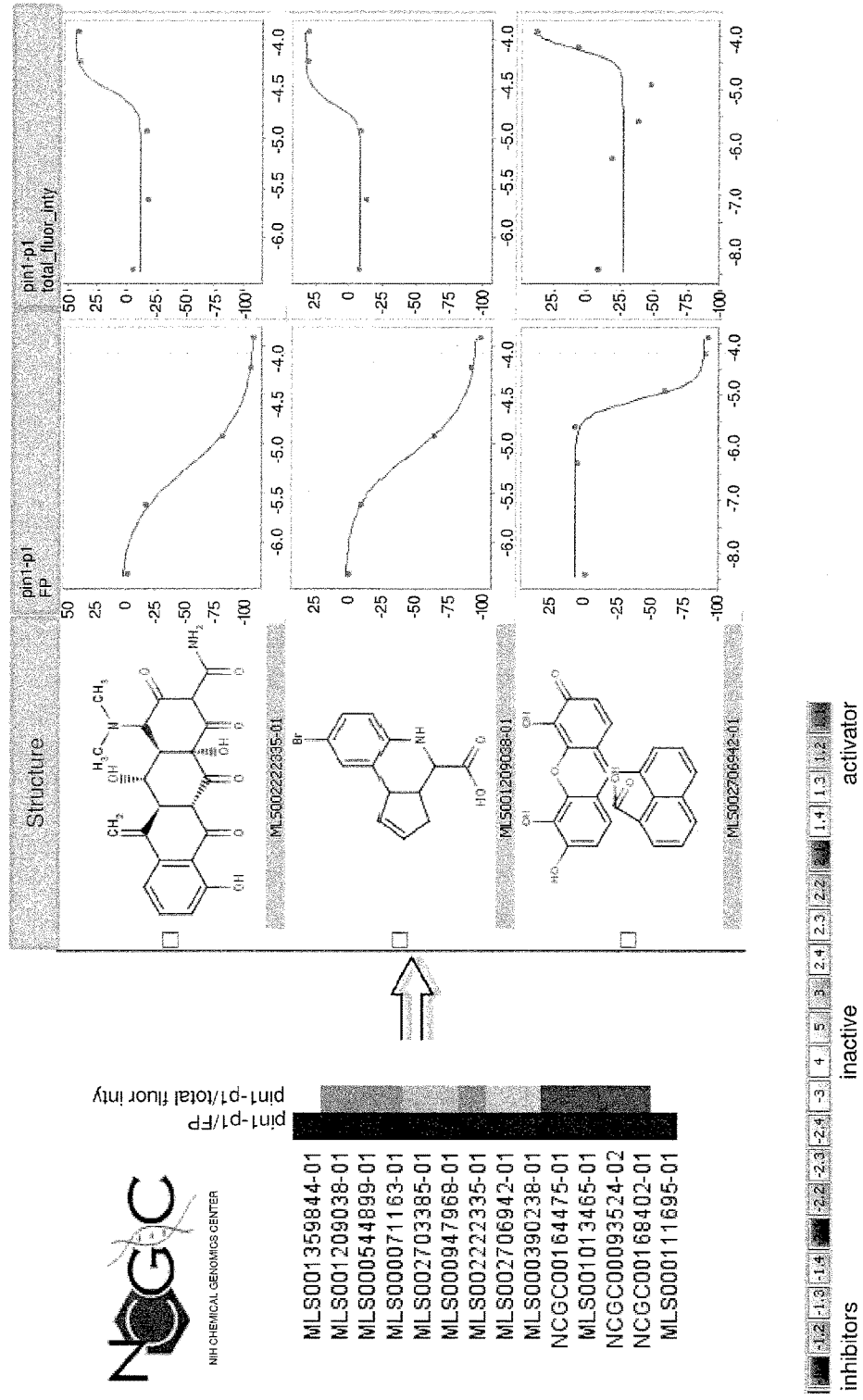
Figure 3B:
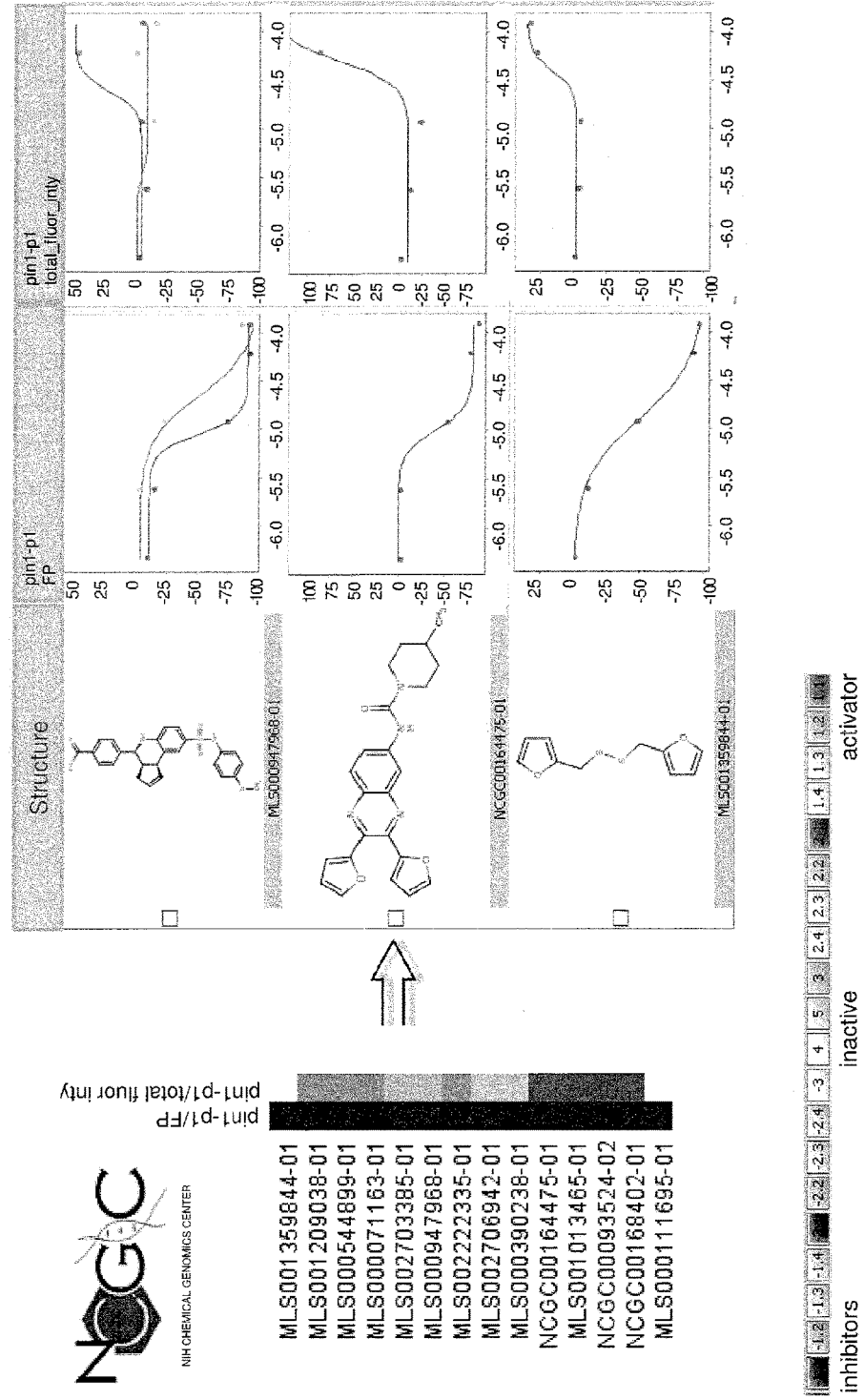
Figure 3C:
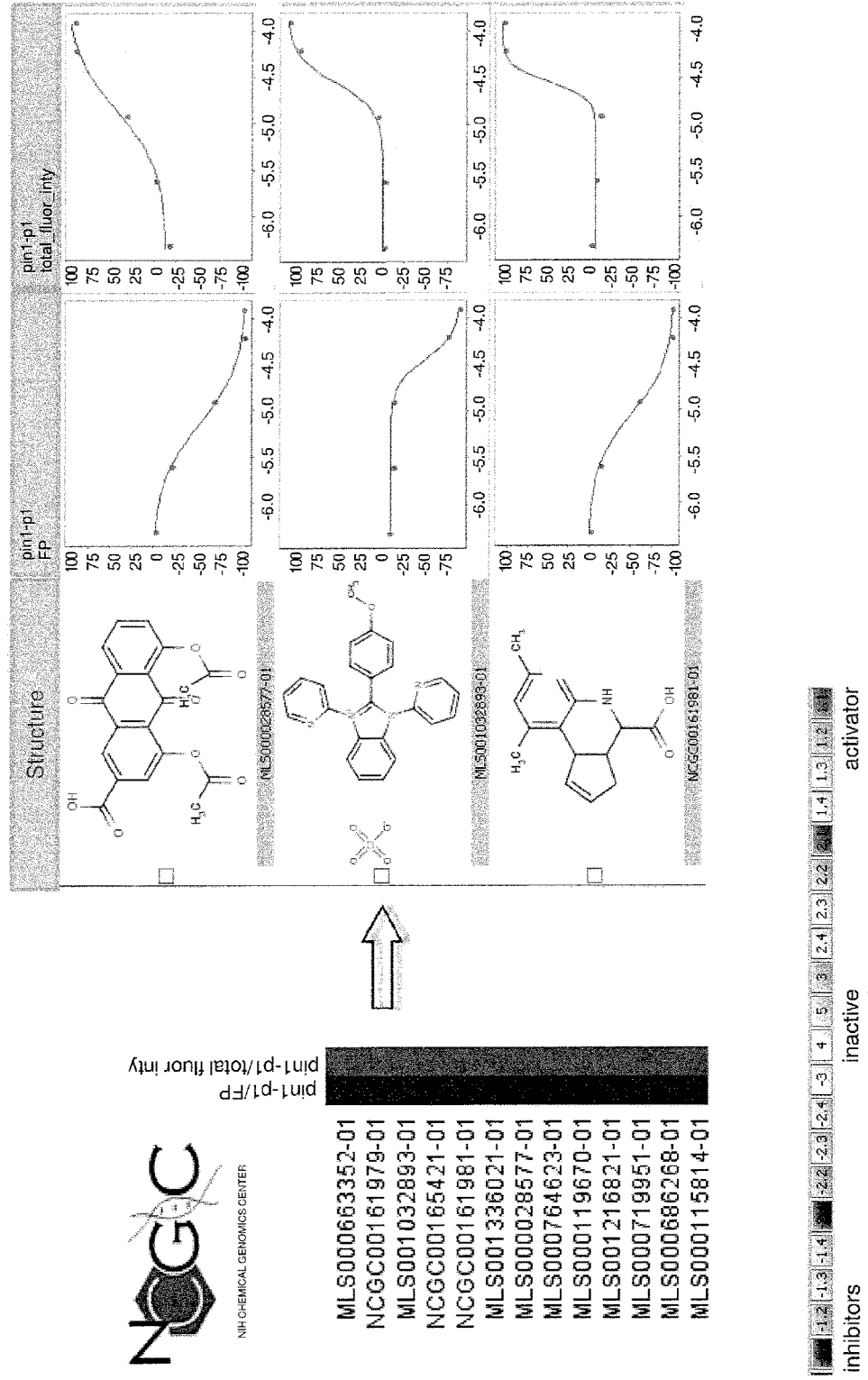
Figure 3C:
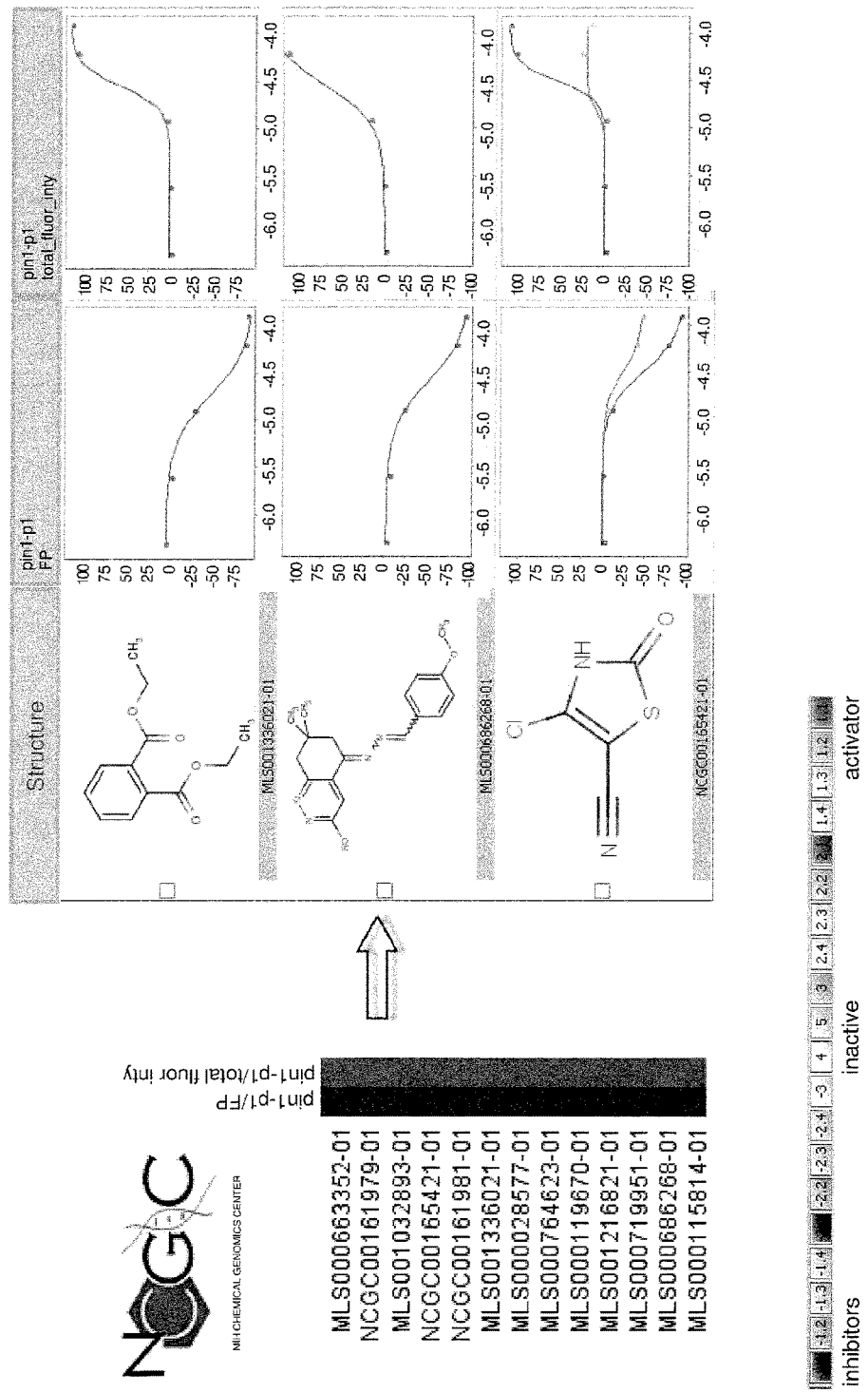
Figure 3D:
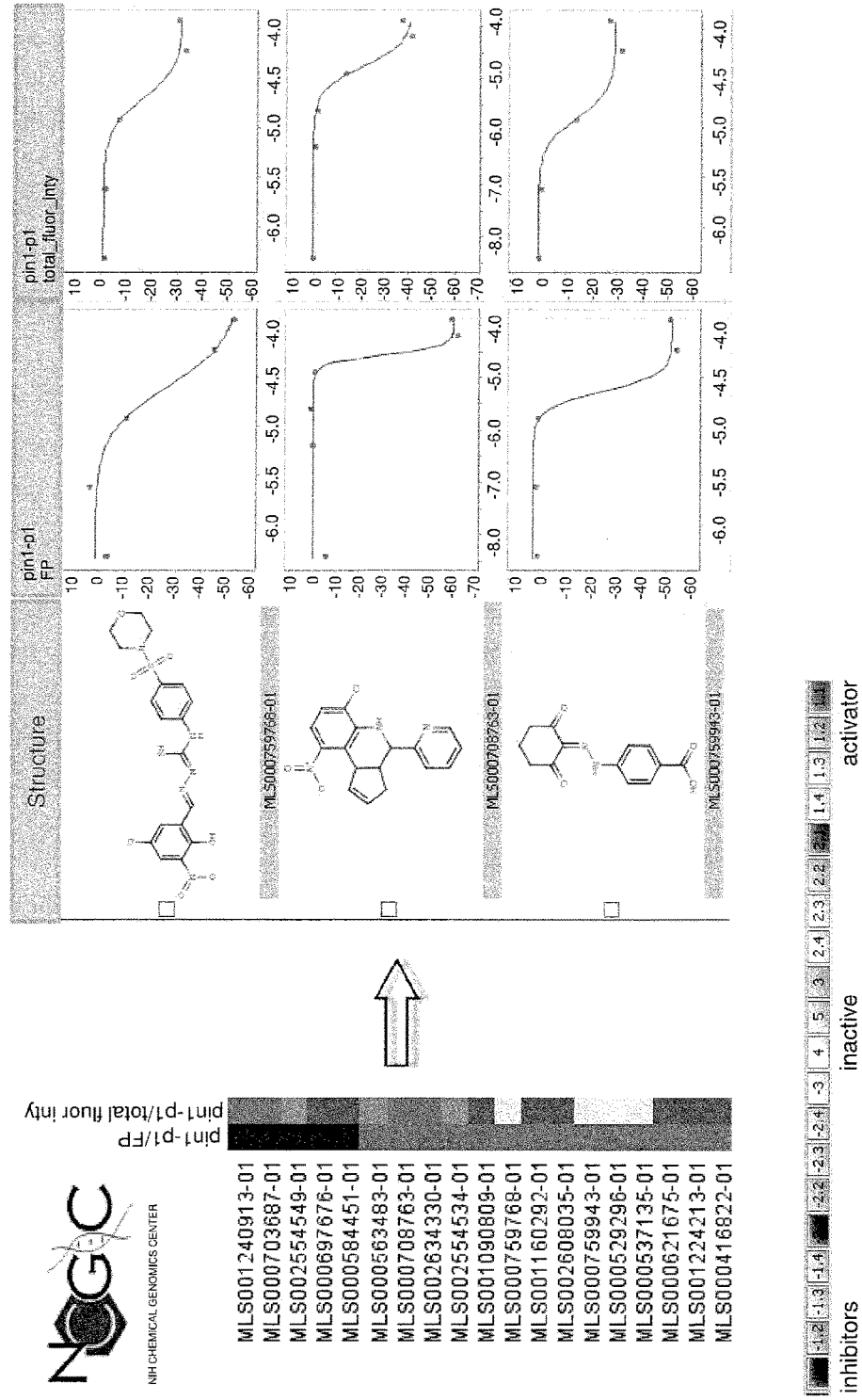
Figure 3D:
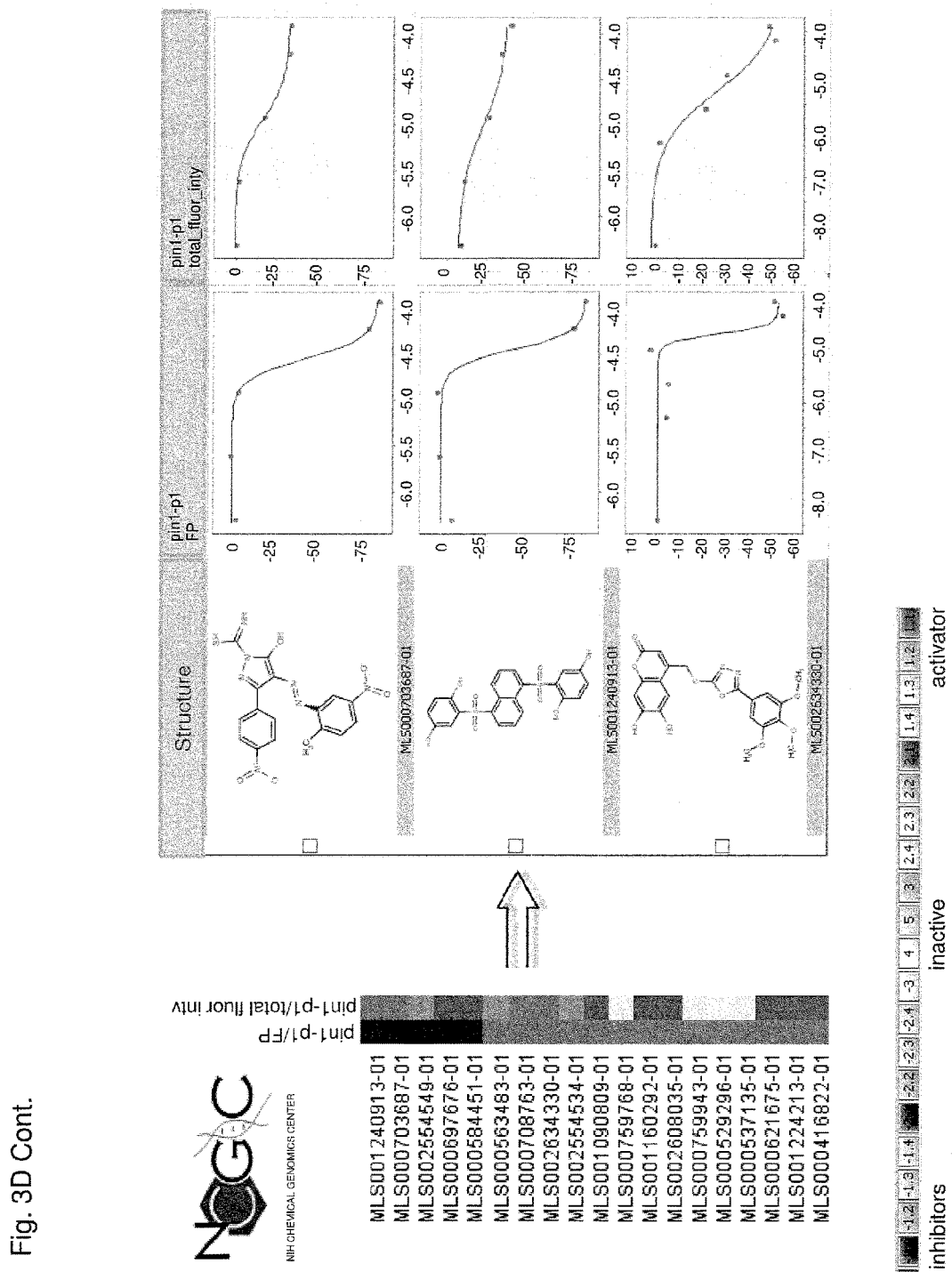

The Pin1 fluorescence polarization competition assay of Example 1 was used to identify inhibitors of Pin1 from a library of 393,181 compounds (Table 3). Initial analysis was accomplished in an offline LOPAC assay. Ten plates were screened, inclusive of 1,280 compounds, collecting 8,960 data points. A hit rate of 1.8% was achieved. A subsequent online LOPAC analysis of 30 plates was also inclusive of 1,280 compounds, collecting 26,880 data points. A hit rate of 1.5% was achieved. qHTS of 1607 plates inclusive of 393,181 compounds was then executed, collecting 2,359,086 data points. A hit rate of 0.6% was achieved (Table 3). Performance of the assay may be gauged using S:B ratio by plate, Z' score by plate, or CV % by plate (FIG. 2).

TABLE 3

Pin-1 Inhibitor Screens and overall Plate Statistics

| Parameter | Offline LOPAC | Online LOPAC | qHTS |
|---|---|---|---|
| System | Offline | Kalypsys robot | Kalypsys robot |
| Plates screened | 10 | 30 | 1607 |
| Plates failed QC | 0 | 0 | 2 (DMSO plate) |
| Compounds tested | 1,280 | 1,280 | 393,181 |
| Concentration-Response Titrations | 3 nM - 57 µM | 3 nM - 57 µM | 3 nM - 114 µM |
| No. of data points | 8,960 | 26,880 | 2,359,086 |
| Z' | 0.79 +/- 0.03 | 0.69 +/- 0.04 | 0.72 +/- 0.04 |
| Signal/Background | 3.29 +/- 0.11 | 2.48 +/- 0.09 | 2.57 +/- 0.09 |
| CV | 5.2 +/- 3.45 | 6.9 +/- 1.93 | 5.6 +/- 2.3 |
| MSR (Pin1-1c) | 1.3 | 1.6 | 1.2 |
| Hit rate (high-quality actives) | 1.8% | 1.5% | 0.6% (2,315) |

Example 3

Identification of Pin1 Inhibitors

Data collected from the Pin1 fluorescence polarization competition assays of Example 2 may be expressed as curves showing log concentration of compound (X axis) by change polarized fluorescence or total fluorescence (FIGS. 3A-3E). Curves showing change polarized fluorescence may be categorized into 5 classes. Class 1 includes complete curves, having 2 asymptotes and an $r^2$ value of ≥0.9, with an efficacy of either >80% (class 1.1) or <80% (class 1.2). Class 1 curves may also be classified as noisy curves when efficacy is >80% and $r^2$<0.9 (class 1.3) or when efficacy is <80% and $r^2$<0.9 (class 1.4). Class 2 includes incomplete curves having 1 asymptote and an $r^2$ value of either >0.9 (subclass a) or <0.9 (subclass b), with an efficacy of either >80% (class 2.1) or <80% (class 2.2). Class 2 curves may also be classified as noisy curves when efficacy is >80% and $r^2$<0.9 (class 2.3) or when efficacy is <80% and $r^2$<0.9 (class 2.4). Class 3 includes single point activity curves having 1 asymptote and an efficacy >3 SD from the mean activity of the sample field at the highest tested concentration. Class 4 includes inactive curves, for which there are no asymptotes and for which efficacy and $r^2$ value are not applicable. A fifth class captures any curves not otherwise classified (FIG. 4).

Analysis of results from the Pin1 fluorescence polarization competition assays of Example 2 reveal that 99% of compounds (388,068 compounds) yield data curves classified as inactive. Active inhibitors include compounds yielding class 1 and class 2 curves and efficacy greater than or equal to 50%. These represented 0.6% of tested compounds, a total of 2315 compounds. Of these, 971 (42%) demonstrate no interference of total fluorescence, 114 (5%) may demonstrate interference of total fluorescence, 1117(48%) demonstrate strong interference of total fluorescence, and 113 (5%) demonstrate a possibility that they quench total fluorescence (FIG. 5). Excluding those that demonstrate strong interference of total fluorescence, 1198 compounds were selected for further analysis. Exemplary Pin1 inhibitors, their chemical structures, and associated data are shown in Tables 1 and 4.

Example 4

Secondary Assessment of Pin1 Inhibitors

To further evaluate the Pin1 inhibitors identified in the Pin1 fluorescence polarization competition assays of Example 2, as analyzed in Example 3, 1086 of the 1198 identified inhibitors of Pin1 were retested in a confirmatory Pin1 fluorescence polarization competition assay. Of the 1086 compounds, 307 yielded class 1.1, 1.2, 2.1, or 2.2 curves and efficacies greater than 50%.

A further secondary assessment was accomplished by replacing the HiFluor-488-labeled probe with Tamra-probe, a red-shifted fluorophore. In the Tamra assay, 285 of the 1086 compounds yielded class 1.1, 1.2, 2.1, or 2.2 curves and efficacies greater than 50%.

Of the compounds evaluated in both secondary assessments, 220 compounds yielded class 1.1, 1.2, 2.1, or 2.2 curves and efficacies greater than or equal to 50% in both. In total 191 compounds met these criteria in all three assays.

TABLE 4

Compound numbers correspond to Table 1 Compounds

| | Average HTS Potency (µM) | Average HTS Efficacy (% Inh.) | Alexa488 Primary | | | Alexa488 Reconfirmed | | | Tamra Secondary | | |
|---|---|---|---|---|---|---|---|---|---|---|---|
| | | | Potency (µM) | Efficacy (% Inh.) | Curve Class | Potency (µM) | Efficacy (% Inh.) | Curve Class | Potency (µM) | Efficacy (% Inh.) | Curve Class |
| 1 | 3 | 84 | 6 | 66 | 1.2 | 1.30 | 90 | 1.1 | 1.20 | 95 | 1.1 |
| 2 | 4 | 81 | 7 | 86 | 1.1 | 2 | 89 | 1.1 | 3 | 69 | 1.2 |
| 3 | 6 | 71 | 10 | 80 | 1.1 | 3 | 61 | 1.2 | 5 | 72 | 1.2 |
| 4 | 7 | 30 | 3 | 23 | 1.2 | nr | nr | | 11 | 37 | 2.2 |
| 5 | 7 | 63 | 18 | 53 | 1.2 | 2 | 75 | 1.2 | 2 | 61 | 1.2 |
| 6 | 14 | 72 | 22 | 42 | 1.1 | 10 | 85 | | 11 | 87 | 2.1 |
| 7 | 29 | 72 | 45 | 63 | 1.2 | 30 | 91 | 2.2 | 14 | 63 | 2.2 |
| 8 | 31 | 74 | 45 | 67 | 2.2 | 30 | 103 | 2.2 | 18 | 52 | 2.2 |
| 9 | 4 | 95 | 10 | 78 | 1.3 | 2 | 111 | 1.1 | 1.20 | 97 | 1.1 |

TABLE 4-continued

Compound numbers correspond to Table 1 Compounds

| | Average HTS Potency (µM) | Average HTS Efficacy (% Inh.) | Alexa488 Primary Potency (µM) | Alexa488 Primary Efficacy (% Inh.) | Alexa488 Primary Curve Class | Alexa488 Reconfirmed Potency (µM) | Alexa488 Reconfirmed Efficacy (% Inh.) | Alexa488 Reconfirmed Curve Class | Tamra Secondary Potency (µM) | Tamra Secondary Efficacy (% Inh.) | Tamra Secondary Curve Class |
|---|---|---|---|---|---|---|---|---|---|---|---|
| 10 | 13.6 | 82.1 | 22.4 | 81.3 | 2.2 | 4.8 | 82.9 | 1.1 | | | |
| 11 | 3 | 83 | 3 | 65 | 1.2 | 3 | 93 | 1.1 | 4 | 91 | 1.1 |
| 12 | 6 | 88 | 15 | 78 | 1.2 | 1.20 | 93 | 1.1 | 1.10 | 92 | 1.1 |
| 13 | 4 | 89 | 9 | 89 | 1.1 | 2 | 89 | 1.1 | 3 | 88 | 1.1 |
| 14 | 10 | 72 | 21 | 71 | 1.2 | 1 | 59 | 1.2 | 8 | 85 | 2.1 |
| 15 | 11 | 133 | 10 | 27 | 2.2 | 11 | 71 | 2.2 | 12 | 300 | 2.1 |
| 16 | 27 | 77 | 76 | 54 | 1.1 | 2 | 93 | 1.1 | 2 | 84 | 1.1 |
| 17 | 5 | 79 | 10 | 64 | 1.4 | 2 | 83 | 1.1 | 3 | 89 | 1.1 |
| 18 | 24 | 77 | 68 | 44 | 1.1 | 2 | 91 | 1.1 | 2 | 95 | 1.1 |
| 19 | 15 | 64 | 38 | 41 | 1.2 | 2 | 73 | 1.2 | 5 | 78 | 2.2 |
| 20 | 7 | 73 | 14 | 73 | 1.1 | 2 | 77 | 1.2 | 6 | 70 | 1.2 |
| 21 | 11 | 62 | 15 | 58 | 1.2 | 11 | 56 | 2.2 | 8 | 72 | 2.2 |
| 22 | 17 | 88 | n/a | n/a | n/a | 21 | 93 | 2.2 | 12 | 82 | 2.2 |
| 23 | 33 | 77 | 76 | 63 | 2.4 | 15 | 92 | 2.1 | 8 | 77 | 2.2 |
| 24 | 23 | 92 | 43 | 76 | 1.2 | 14 | 101 | 1.2 | 12 | 100 | 2.1 |
| 25 | 34 | 47 | 38 | 22 | 2.2 | nr | nr | | 30 | 73 | 3.0 |
| 26 | 22 | 94 | 20 | 71 | 1.1 | 24 | 111 | 2.1 | 21 | 101 | 2.1 |
| 27 | 27 | 108 | 23 | 85 | 1.1 | 30 | 112 | 2.1 | 27 | 126 | 2.1 |
| 28 | 0.89 | 94 | 1.69 | 89 | 1.1 | 0.08 | 99 | 1.1 | | | |
| 29 | 0.90 | 85 | 3 | 83 | 1.1 | 0.10 | 90 | 1.1 | 0.10 | 82 | 1.1 |
| 30 | 1.16 | 79 | 3 | 69 | 1.2 | 0.34 | 89 | 1.1 | 0.43 | 80 | 1.1 |
| 31 | 2 | 80 | 4 | 74 | 1.1 | 2 | 85 | 1.1 | 2 | 82 | 1.1 |
| 32 | 13 | 61 | 38 | 21 | 1.2 | 0.24 | 82 | 1.1 | 0.19 | 81 | 1.1 |
| 33 | 21 | 58 | 48 | 20 | 1.2 | 7 | 84 | 2.2 | 10 | 70 | 2.2 |
| 34 | 27 | 91 | 20 | 65 | 1.4 | 24 | 104 | 2.1 | 38 | 103 | 3.0 |
| 35 | 19 | 71 | 38 | 26 | 2.4 | 9 | 112 | 2.1 | 11 | 75 | 2.2 |
| 36 | 15 | 80 | 11 | 101 | 1.1 | 14 | 62 | 2.2 | 19 | 76 | 2.2 |
| 37 | 37 | 47 | 85 | 19 | 1.2 | 15 | 63 | 2.2 | 12 | 58 | 2.2 |
| 38 | 13 | 101 | 19 | 103 | 1.1 | 6 | 98 | 1.1 | | | |
| 39 | 17 | 41 | 14 | 28 | 2.2 | nr | nr | | 21 | 53 | 3.0 |
| 40 | 20 | 83 | 25 | 55 | 1.1 | 10 | 99 | 2.1 | 24 | 96 | 2.2 |
| 41 | 23 | 77 | 30 | 88 | 2.2 | 19 | 62 | 2.2 | 19 | 80 | 2.2 |
| 42 | 23 | 76 | 19 | 73 | 1.2 | 27 | 82 | 2.2 | 24 | 73 | 2.2 |
| 43 | 20 | 67 | 16 | 63 | 1.2 | nr | nr | | 24 | 71 | 3.0 |
| 44 | 24 | 79 | 36 | 90 | 2.2 | 12 | 63 | 2.2 | 24 | 83 | 2.2 |
| 45 | 30 | 71 | 22 | 72 | 2.1 | nr | nr | | 38 | 71 | 3.0 |
| 46 | 30 | 81 | 43 | 82 | 2.2 | 27 | 84 | 2.2 | 21 | 78 | 2.2 |
| 47 | 40 | 67 | 79 | 26 | 1.2 | 19 | 84 | 2.2 | 21 | 91 | 2.1 |
| 48 | 1 | 63 | 1 | 53 | 1.4 | 1 | 73 | 1.1 | | | |
| 49 | 25 | 48 | 50 | 27 | 1.2 | 1 | 70 | 1.1 | | | |
| 50 | 4 | 95 | 1 | 93 | 1.1 | 7 | 98 | 1.1 | | | |

Example 5

A Pilot Screen for Pin1 Inhibitors Identified an Anti-Proliferative Agent

A high-throughput screen for identifying Pin1 inhibitors was developed using a single-step fluorescence polarization-based displacement assay (FP-HTS). The FP-HTS detects molecules that compete for the substrate binding to the catalytic active site, measures ligand binding under equilibrium conditions, and does not suffer from product inhibition. The HF488 fluorescent probes for the FP assay contain only four residue core structure of Bth-L-phos.Thr-Pip-Nal (pTide), with a Kd of 258 nM for Pin1, was synthesized by Anaspec. We performed FP-HTS in a 384-well plate format with full length Pin1 and produced robust FP, resulting in a 6-7 fold increase in polarization degree values, using a Synergy II plate reader. This novel FP-HTS showed robust and reproducible performance. The assay can tolerate up to 10% DMSO. The Z' is around 0.70 and is consistent for day-to-day performance. The coefficient of variation is in the range of 4-5%. More importantly, we have shown that both pTide, the unlabeled Pin1 peptide as the positive control in this project, and juglone, the Pin1 small molecule inhibitor, displaced HF488 probe from Pin1. Although it is difficult to determine the Kd for the covalent and irreversible inhibitor juglone, the Kd for pTide was ~250 nM, similar to that derived from PPIase-based assays.

The FP-HTS with a 5 nM probe and 200 nM Pin1 was used to conduct a pilot screen on a selected set of chemical libraries. We obtained the resulting potential positive hits and grouped them into 3 classes according to the Z-score, which is folds of standard deviation below the mean. The top inhibitory chemical was the clinically used drug 13-cis-retinoic acid (cis-RA). Characteristics of cis-RA is include that 1) cis-RA is not listed in promiscuous inhibitor databases 2) the pairing compound of cis-RA, all-trans retinoic acid (trans-RA), is currently used as oral prescription for patients with acute promyelocytic leukemia (AML); 3) both cis-RA and trans-RAs are used as a medication in the phase 11/111 clinical trial for breast cancer, and more because of its ability to kill rapidly dividing cells; and 4) although it has been reported that RAs target on retinoic acid receptor (RAR), the exact mechanism of the anticancer action is unknown.

The anti-cancer effect of RAs was examined to determine whether it depends on RAR in the breast cancer cells. RARa knockdown can only partially rescue-cis-RA-mediated cell death, indicating that RAs may have unidentified "off-target effect." To confirm that RAs indeed target Pin1, we examined cis-RA and trans-RA in the FP assay, and, surprisingly, found that trans-RA displayed even more prominent Pin1 inhibition than cis-RA and that cis-RA would eventually catch up with trans-RA in the long-term incubation with Pin1, likely due to resonance-mediated cis-trans conversion. In the PPIase assay, Pin1 activity was blocked by either cis- or trans-RA in a dose-dependent manner. These data confirm that the interaction between RAs and Pin1 is specific and not due to aggregation. Furthermore, both trans and cis RA blocked the association between Pin1 and DAPK1 in a dose-dependent manner, with trans being more potent. These results indicate that RAs binds to Pin1 C-terminal catalytic domain because DAPK1 is known to bind this domain (Lee et al., 2011 Mol Cell in press). In determining which amino acid residues in the Pin1 catalytic domain are important for retinoic acid binding, point mutations of Pin1 including K63A, S67E, R68/69A, H59A or S71E completely or significantly abolished trans-RA binding to Pin1. Together, these data indicate that RAs inhibit Pin1 by occupying its catalytic PPIase pocket in the C-terminus and that phosphorylation of Ser67 or Ser71 inhibits RA binding to Pin1.

To further discern the causal relationship between the anti-proliferative effect of RAs on Pin1, cell viability of three breast cancer cell lines was tested with different dosages of cis- or trans-RA, of which SKBR3 and T47D exhibited preferential sensitivity to RAs with an IC50 in the nano-molar range, while the normal cell line MCF10A remained unaffected. This discrepancy between cell lines was correlated with the RAs' ability to suppress Pin1 expression. Pin1 level was decreased by treatment of RAs in drugs-responsive SKBR3 and T47D, but not in drugs-irresponsive normal cells, MCF10A, in which Pin1 target protein, cyclin D1, served as biomarker of in vivo Pin1 activity.

Moreover, RAs did not alter Pin1 mRNA level, but did reduce Pin1 protein stability, suggesting that RAs interact with Pin1, result in Pin1 degradation, and subsequently leads to anti-proliferation of breast cancer cells. To further confirm this premise, wild-type mouse embryonic fibroblast (WT MEF) and Pin1 knockout MEF (Pin1 KO MEF) were used to test trans-RA-mediated cell viability. As expected, Pin1 KO MEF was more resistant to trans-RA than WT MEF due to lack of drug target. In addition, Pin1 KO MEF stably expressing WT Pin1, but not W34 K63A Pin1 mutant, enabled cells to re-sensitize trans-RA. These results indicate that RAs-mediated cell death is at least in part dependent on Pin1.

We have further shown that combinations of therapeutic compounds including retinoic acid compounds are useful for treating cancer, e.g., cancer characterized by elevated Pin1 activity. Results obtained from the treatment of breast cancer cells overexpres sing Pin1 with ATRA or Doxorubicin or their combination, followed by counting cancer cell numbers show that ATRA and Doxorubicin combination dramatically increases anticancer potency and reduce the dose of each drug to inhibit cancer cell growth. Therefore, ATRA can drastically reduce dose and toxicity of Doxorubicin and other chemotherapeutic drugs.

We have also shown that Pin1 inhibition, using siRNA, dramatically reduces Neu/Erb2 overexpression and cell proliferation of human breast cancer cells that have Neu/Erb2 gene amplification. This provides a method to identify a Pin1 modulatory compound by applying a test compound to human-derived cancer cells that have Neu/Erb2 gene amplification, and determining the effect of the test compound on Neu/Erb2 overexpression and cell proliferation.

In addition, we have developed cell-based assays to screen and validate Pin1 inhibitor hits. We have shown 1) that Pin1 is highly expressed in HER2-positive human breast cancer tissues; 2) that Pin1 inhibition almost completely suppresses HER2 overexpression on cell surface in human HER2+ breast cancer cell lines such as AU565 and SKBR3 cells; 3) that Pin1 inhibition greatly increases the sensitivity of HER2+ breast cancer cells to the mTOR inhibitor, but not to the HER2 inhibitor, suggesting that Pin1 might act on Her2 to regulate cell growth; 4) that Pin1 acts on Neu and multiple substrates in Neu-mediated oncogenic pathway; and 5) that Pin 1 knockout in mice inhibits breast cancer development induced by activated Her2. Therefore, Pin1 is essential for maintaining HER2 overexpression and growth of human HER2+ breast cancer cells. Given that HER2 expression on cell surface and cell growth are readily assayed on 384-well format, we can test the ability of the hits to repress HER2 overexpression and cell growth of HER2_AU565 and SKBR3 cells, which will be treated with Pin1 prodrugs or hits, and then immunostained with Alexa 488-anti-HER2 monoclonal antibody (BioLegend), followed by automated microscopy.

OTHER EMBODIMENTS

All publications, patents, and patent applications mentioned in this specification are herein incorporated by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follows in the scope of the claims.

Other embodiments are within the claims.

What is claimed is:

1. A method of inhibiting Pin1 by contacting Pin1 with a compound having the structure selected from Compound 48 and Compound 49:

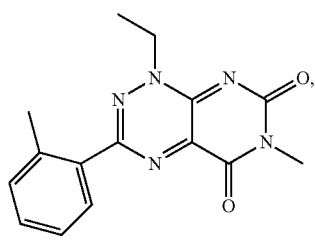

(48)

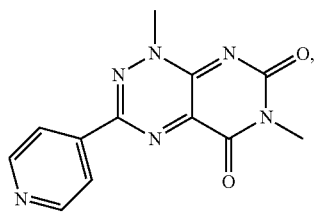

(49)

wherein said compound is a Pin1 inhibitor.

2. The method of claim 1, wherein said Pin1 is in a cell.

3. The method of claim 2, wherein said cell is a human cell.

\* \* \* \* \*

UNITED STATES PATENT AND TRADEMARK OFFICE
CERTIFICATE OF CORRECTION

PATENT NO. : 9,730,941 B2
APPLICATION NO. : 14/406401
DATED : August 15, 2017
INVENTOR(S) : Kun Ping Lu et al.

Page 1 of 3

It is certified that error appears in the above-identified patent and that said Letters Patent is hereby corrected as shown below:

On the Title Page

Page 3, in Liou et al, replace "99(3) 1 335-40" with --99(3):1335-40--.

In the Specification

Column 1, Lines 15-17, replace "This invention was made with government support under grants DA031663 and CA167677 awarded by NIH numbers NIH R03DA031663 and R01CA167677. The government has certain rights in the invention." with --This invention was made with government support under grants DA031663 and CA167677 awarded by NIH. The government has certain rights in the invention--.

Column 2, Line 4, replace "RARa" with --RARα--;
    Line 24, replace "in a subject maybe determined" with --in a subject may be determined--;
    Line 39, replace "of the Pin1 protein" with --of the Pin1 protein.--;
    Line 51, replace "adrenogenital ayndrome" with --adrenogenital syndrome--.

Column 3, Line 35, replace "leukemi" with --leukemia--;
    Line 35, replace "gentuzumab" with --gemtuzumab--.

Column 29, Lines 22-23, replace "benzoisoxazolyl" with --benzisoxazolyl--.

Column 30, Line 22, replace "heteralkynyl" with --heteroalkynl--;
    Lines 24-25, replace "as use herein" with --as used herein--.

Column 31, Line 57, replace "double bond at A4" with --double bond at Δ4--.

Column 32, Line 12, replace "flupredidene" with --fluprednidene--.

Signed and Sealed this
Twenty-eighth Day of August, 2018

Andrei Iancu
*Director of the United States Patent and Trademark Office*

CERTIFICATE OF CORRECTION (continued)

Column 34, Lines 49-50, replace "phosphoserinelthreonine" with
--phosphoserine-threonine-proline--;
    Line 56, replace "mount a type I IFN antiviral responses" with --mount a type I IFN antiviral response--.

Column 35, Line 9, replace "The WW domain acts a novel" with --The WW domain acts as a novel--;
    Lines 24-26 should start the next paragraph.

Column 37, Lines 38-39, replace "glycol ether).sub.n" with --glycol ether)$_n$--;
    Lines 40-41, replace "dimethylamminio" with --dimethylamino--.

Column 40, Lines 15-16, replace "Radioimmunoas say" with --Radioimmunoassay--;
    Lines 34-35, replace "genes that effect Pin1 marker levels" with --genes that affect Pin1 marker levels--.

Column 41, Line 23, replace "adrenogenital ayndrome" with --adrenogential syndrome--.

Column 42, Lines 32-33, replace "oligodenroglioma" with --oligodendroglioma--;
    Lines 60-61, replace "to treat a disorder Pin1-associated disorder)." with --to treat a Pin1-associated disorder).--.

Column 45, Line 48, replace "modified to insure that" with --modified to ensure that--.

Column 47, Line 4, replace "intraveneously" with --intravenously--;
    Line 26, replace "polyvinyl pyrolidone" with --polyvinyl pyrrolidone--;
    Line 45, replace "gallate, .alpha.tocopherol" with --gallate, α-tocopherol--.

Column 48, Lines 16-17, replace "such a talc" with --such as talc--.

Column 51, Lines 66-67, replace "inflixamab, adelimumab" with --infliximab, adalimumab--.

Column 52, Line 3, replace "pranalcasan" with --pralnacasan--;
    Line 16, replace "ceforanid" with --ceforanide--;
    Line 48, replace "gentuzumab" with --gemtuzumab--;
    Line 50, replace "melphalen" with --melphalan--.

Column 55, Lines 29-30, replace "treatment an individual" with --treatment of an individual--.

Column 56, Line 21, replace "3 s vacuum dry" with --3s vacuum dry--;
    Line 26, replace "3 s vacuum dry" with --3s vacuum dry--;
    Line 54, replace "Ox enzyme" with --0x enzyme--.

Column 58, Line 1, replace "is <80%" with --is ≤80%--;
    Line 5, replace "is <80%" with --is ≤80%--;
    Line 7, replace "is <80%" with --is ≤80%--.

Column 60, Lines 55-56, replace "Characteristics of cis-RA is include that" with --Characteristics of cis-RA include that--.

Column 61, Line 55, replace "cells overexpress sing" with --cells overexpressing--.